(12) United States Patent
Peterson et al.

(10) Patent No.: US 12,708,508 B2
(45) Date of Patent: Aug. 18, 2026

(54) PROSTHETIC VALVE WITH ENHANCED SEALING

(71) Applicant: EDWARDS LIFESCIENCES CORPORATION, Irvine, CA (US)

(72) Inventors: Matthew A. Peterson, Costa Mesa, CA (US); Siddharth Vad, Irvine, CA (US); Scott Louis Shary, Huntington Beach, CA (US); Taylor Jacob Scheinblum, Newport Beach, CA (US); Kevin M. Golemo, Mission Viejo, CA (US); Yevgeniy Davidovich Kaufman, Irvine, CA (US); David Robert Landon, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 714 days.

(21) Appl. No.: 18/111,278

(22) Filed: Feb. 17, 2023

(65) Prior Publication Data

US 2023/0200980 A1 Jun. 29, 2023

Related U.S. Application Data

(63) Continuation of application No. PCT/US2021/047000, filed on Aug. 20, 2021.

(Continued)

(51) Int. Cl.
*A61F 2/24* (2006.01)

(52) U.S. Cl.
CPC .......... *A61F 2/2409* (2013.01); *A61F 2/2418* (2013.01); *A61F 2220/0008* (2013.01);

(Continued)

(58) Field of Classification Search
CPC .................. A61F 2/2418; A61F 2/2409; A61F 2220/0008–0016; A61F 2250/0069–007
See application file for complete search history.

(56) References Cited

U.S. PATENT DOCUMENTS

| | | | |
|---|---|---|---|
| 3,409,013 | A | 11/1968 | Berry |
| 3,472,230 | A | 10/1969 | Fogarty |

(Continued)

FOREIGN PATENT DOCUMENTS

| | | | |
|---|---|---|---|
| CA | 2304325 | C | 5/2008 |
| DE | 2246526 | A1 | 3/1973 |

(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708

(Continued)

*Primary Examiner* — Rebecca S Preston
(74) *Attorney, Agent, or Firm* — Thomas C. Richardson

(57) ABSTRACT

Apparatuses, systems, and methods for prosthetic valves. Embodiments of prosthetic valves may include sealing bodies configured for an anchor to at least partially pass through. The pass through may allow for the sealing body to seal to a portion of a patient's heart in the event of a miscapture of a leaflet by the anchor. Embodiments may include modular valve systems and prosthetic valves including anchors for coupling to chordae, trabeculae, or papillary structures of a patient's heart. Embodiments may include prosthetic valves including anchors for engaging calcification of a patient's native valve.

21 Claims, 38 Drawing Sheets

Related U.S. Application Data

(60) Provisional application No. 63/199,267, filed on Dec. 16, 2020, provisional application No. 63/071,684, filed on Aug. 28, 2020.

(52) U.S. Cl.
CPC ................ *A61F 2250/0039* (2013.01); *A61F 2250/0069* (2013.01); *A61F 2250/007* (2013.01)

(56) References Cited

U.S. PATENT DOCUMENTS 3,548,417 A 12/1970 Kischer et al.
3,587,115 A 6/1971 Shiley
3,657,744 A 4/1972 Ersek
3,671,979 A 6/1972 Moulopoulos
3,714,671 A 2/1973 Edwards et al.
3,739,402 A 6/1973 Cooley et al.
3,755,823 A 9/1973 Hancock
4,011,947 A 3/1977 Sawyer
4,035,849 A 7/1977 Angell et al.
4,056,854 A 11/1977 Boretos et al.
4,079,468 A 3/1978 Liotta et al.
4,106,129 A 8/1978 Carpentier et al.
4,204,283 A 5/1980 Bellhouse et al.
4,222,126 A 9/1980 Boretos et al.
4,265,694 A 5/1981 Boretos et al.
4,297,749 A 11/1981 Davis et al.
4,339,831 A 7/1982 Johnson
4,340,977 A 7/1982 Brownlee et al.
4,343,048 A 8/1982 Ross et al.
4,345,340 A 8/1982 Rosen
4,373,216 A 2/1983 Klawitter
4,406,022 A 9/1983 Roy
4,470,157 A 9/1984 Love
4,477,930 A 10/1984 Totten et al.
4,490,859 A 1/1985 Black et al.
4,535,483 A 8/1985 Klawitter et al.
4,553,545 A 11/1985 Maass et al.
4,574,803 A 3/1986 Storz
4,592,340 A 6/1986 Boyles
4,605,407 A 8/1986 Black et al.
4,612,011 A 9/1986 Kautzky
4,643,732 A 2/1987 Pietsch et al.
4,655,771 A 4/1987 Wallsten
4,692,164 A 9/1987 Dzemeshkevich et al.
4,733,665 A 3/1988 Palmaz
4,759,758 A 7/1988 Gabbay
4,762,128 A 8/1988 Rosenbluth
4,777,951 A 10/1988 Cribier et al.
4,787,899 A 11/1988 Lazarus
4,787,901 A 11/1988 Baykut
4,796,629 A 1/1989 Grayzel
4,829,990 A 5/1989 Thuroff et al.
4,851,001 A 7/1989 Taheri
4,856,516 A 8/1989 Hillstead
4,865,600 A 9/1989 Carpentier et al.
4,878,495 A 11/1989 Grayzel
4,878,906 A 11/1989 Lindemann et al.
4,883,458 A 11/1989 Shiber
4,922,905 A 5/1990 Strecker
4,966,604 A 10/1990 Reiss
4,979,939 A 12/1990 Shiber
4,986,830 A 1/1991 Owens et al.
4,994,077 A 2/1991 Dobben
5,007,896 A 4/1991 Shiber
5,026,366 A 6/1991 Leckrone
5,032,128 A 7/1991 Alonso
5,037,434 A 8/1991 Lane
5,047,041 A 9/1991 Samuels
5,059,177 A 10/1991 Towne et al.
5,080,668 A 1/1992 Bolz et al.
5,085,635 A 2/1992 Cragg
5,089,015 A 2/1992 Ross
5,108,370 A 4/1992 Walinsky
5,152,771 A 10/1992 Sabbaghian et al.
5,163,953 A 11/1992 Vince
5,167,628 A 12/1992 Boyles
5,192,297 A 3/1993 Hull
5,232,446 A 8/1993 Arney
5,266,073 A 11/1993 Wall
5,282,847 A 2/1994 Trescony et al.
5,295,958 A 3/1994 Shturman
5,326,371 A 7/1994 Love et al.
5,332,402 A 7/1994 Teitelbaum
5,360,444 A 11/1994 Kusuhara
5,370,685 A 12/1994 Stevens
5,397,351 A 3/1995 Pavcnik et al.
5,411,055 A 5/1995 Kane
5,411,522 A 5/1995 Trott
5,411,552 A 5/1995 Andersen et al.
5,415,667 A 5/1995 Frater
5,443,446 A 8/1995 Shturman
5,480,424 A 1/1996 Cox
5,500,014 A 3/1996 Quijano et al.
5,545,209 A 8/1996 Roberts et al.
5,545,214 A 8/1996 Stevens
5,549,665 A 8/1996 Vesely et al.
5,554,185 A 9/1996 Block et al.
5,571,175 A 11/1996 Vanney et al.
5,591,185 A 1/1997 Kilmer et al.
5,599,305 A 2/1997 Hermann et al.
5,607,464 A 3/1997 Trescony et al.
5,609,626 A 3/1997 Quijano et al.
5,639,274 A 6/1997 Fischell et al.
5,665,115 A 9/1997 Cragg
5,697,382 A 12/1997 Love et al.
5,716,417 A 2/1998 Girard et al.
5,728,068 A 3/1998 Leone et al.
5,749,890 A 5/1998 Shaknovich
5,756,476 A 5/1998 Epstein et al.
5,769,812 A 6/1998 Stevens et al.
5,800,508 A 9/1998 Goicoechea et al.
5,840,081 A 11/1998 Andersen et al.
5,855,597 A 1/1999 Jayaraman
5,855,601 A 1/1999 Bessler et al.
5,855,602 A 1/1999 Angell
5,906,619 A 5/1999 Olson et al.
5,925,063 A 7/1999 Khosravi
5,957,949 A 9/1999 Leonhardt et al.
5,968,068 A 10/1999 Dehdashtian et al.
6,027,525 A 2/2000 Suh et al.
6,042,607 A 3/2000 Williamson et al.
6,086,612 A 7/2000 Jansen
6,113,631 A 9/2000 Jansen
6,132,473 A 10/2000 Williams et al.
6,168,614 B1 1/2001 Andersen et al.
6,171,335 B1 1/2001 Wheatley et al.
6,174,327 B1 1/2001 Mertens et al.
6,210,408 B1 4/2001 Chandrasekaran et al.
6,217,585 B1 4/2001 Houser et al.
6,221,091 B1 4/2001 Khosravi
6,231,602 B1 5/2001 Carpentier et al.
6,245,040 B1 6/2001 Inderbitzen et al.
6,245,102 B1 6/2001 Jayaraman
6,251,093 B1 6/2001 Valley et al.
6,287,339 B1 9/2001 Vazquez et al.
6,299,637 B1 10/2001 Shaolian et al.
6,302,906 B1 10/2001 Goicoechea et al.
6,306,141 B1 10/2001 Jervis
6,312,465 B1 11/2001 Griffin et al.
6,338,740 B1 1/2002 Carpentier
6,350,277 B1 2/2002 Kocur
6,358,277 B1 3/2002 Duran
6,379,372 B1 4/2002 Dehdashtian et al.
6,425,916 B1 7/2002 Garrison et al.
6,440,164 B1 8/2002 DiMatteo et al.
6,454,799 B1 9/2002 Schreck
6,458,153 B1 10/2002 Bailey et al.
6,461,382 B1 10/2002 Cao
6,468,660 B2 10/2002 Ogle et al.
6,482,228 B1 11/2002 Norred
6,488,704 B1 12/2002 Connelly et al.

(56) References Cited

U.S. PATENT DOCUMENTS 6,527,800 B1 3/2003 McGuckin et al.
6,527,979 B2 3/2003 Constantz et al.
6,540,782 B1 4/2003 Snyders
6,569,196 B1 5/2003 Vesely
6,575,959 B1 6/2003 Sarge et al.
6,582,462 B1 6/2003 Andersen et al.
6,605,112 B1 8/2003 Moll et al.
6,610,088 B1 8/2003 Gabbay
6,629,534 B1 10/2003 St. Goar et al.
6,676,698 B2 1/2004 McGuckin et al.
6,695,878 B2 2/2004 McGuckin et al.
6,712,836 B1 3/2004 Berg et al.
6,716,207 B2 4/2004 Farnholtz
6,729,356 B1 5/2004 Baker et al.
6,730,118 B2 5/2004 Spenser et al.
6,733,525 B2 5/2004 Yang et al.
6,746,422 B1 6/2004 Noriega et al.
6,749,560 B1 6/2004 Konstorum et al.
6,767,362 B2 7/2004 Schreck
6,780,200 B2 8/2004 Jansen
6,790,229 B1 9/2004 Berreklouw
6,790,230 B2 9/2004 Beyersdorf et al.
6,830,584 B1 12/2004 Seguin
6,875,231 B2 4/2005 Anduiza et al.
6,893,460 B2 5/2005 Spenser et al.
6,908,481 B2 6/2005 Cribier
6,974,476 B2 12/2005 McGuckin et al.
7,018,406 B2 3/2006 Seguin et al.
7,186,265 B2 3/2007 Sharkawy et al.
7,192,440 B2 3/2007 Andreas et al.
7,198,646 B2 4/2007 Figulla et al.
7,201,772 B2 4/2007 Schwammenthal et al.
7,276,078 B2 10/2007 Spenser et al.
7,276,084 B2 10/2007 Yang et al.
7,318,278 B2 1/2008 Zhang et al.
7,374,571 B2 5/2008 Pease et al.
7,381,210 B2 6/2008 Zarbatany et al.
7,381,219 B2 6/2008 Salahieh et al.
7,393,360 B2 7/2008 Spenser et al.
7,429,269 B2 9/2008 Schwammenthal et al.
7,442,204 B2 10/2008 Schwammenthal et al.
7,445,631 B2 11/2008 Salahieh et al.
7,462,191 B2 12/2008 Spenser et al.
7,510,575 B2 3/2009 Spenser et al.
7,524,330 B2 4/2009 Berreklouw
7,530,253 B2 5/2009 Spenser et al.
7,553,324 B2 6/2009 Andreas et al.
7,579,381 B2 8/2009 Dove
7,585,321 B2 9/2009 Cribier
7,618,446 B2 11/2009 Andersen et al.
7,621,948 B2 11/2009 Herrmann et al.
7,704,222 B2 4/2010 Wilk et al.
7,736,327 B2 6/2010 Wilk et al.
7,748,389 B2 7/2010 Salahieh et al.
7,753,949 B2 7/2010 Lamphere et al.
7,806,919 B2 10/2010 Bloom et al.
7,824,443 B2 11/2010 Salahieh et al.
7,837,727 B2 11/2010 Goetz et al.
7,892,281 B2 2/2011 Seguin et al.
7,914,569 B2 3/2011 Nguyen et al.
7,914,575 B2 3/2011 Guyenot et al.
7,959,672 B2 6/2011 Salahieh et al.
7,972,378 B2 7/2011 Tabor et al.
7,981,151 B2 7/2011 Rowe
7,993,392 B2 8/2011 Righini et al.
7,993,394 B2 8/2011 Hariton et al.
8,007,992 B2 8/2011 Tian et al.
8,016,877 B2 9/2011 Seguin et al.
8,029,556 B2 10/2011 Rowe
8,052,750 B2 11/2011 Tuval et al.
8,070,800 B2 12/2011 Lock et al.
8,070,802 B2 12/2011 Lamphere et al.
8,075,615 B2 12/2011 Eberhardt et al.
8,080,054 B2 12/2011 Rowe
8,092,520 B2 1/2012 Quadri
8,092,521 B2 1/2012 Figulla et al.
8,109,996 B2 2/2012 Stacchino et al.
8,118,866 B2 2/2012 Herrmann et al.
8,136,218 B2 3/2012 Millwee et al.
8,137,398 B2 3/2012 Tuval et al.
8,157,852 B2 4/2012 Bloom et al.
8,167,932 B2 5/2012 Bourang et al.
8,167,934 B2 5/2012 Styrc et al.
8,182,530 B2 5/2012 Huber
8,206,437 B2 6/2012 Bonhoeffer et al.
8,216,174 B2 7/2012 Wilk et al.
8,216,301 B2 7/2012 Bonhoeffer et al.
8,219,229 B2 7/2012 Cao et al.
8,220,121 B2 7/2012 Hendriksen et al.
8,236,045 B2 8/2012 Benichou et al.
8,246,675 B2 8/2012 Zegdi
8,246,678 B2 8/2012 Salahieh et al.
8,252,051 B2 8/2012 Chau et al.
8,252,052 B2 8/2012 Salahieh et al.
8,287,584 B2 10/2012 Salahieh et al.
8,313,525 B2 11/2012 Tuval et al.
8,317,858 B2 11/2012 Straubinger et al.
8,323,335 B2 12/2012 Rowe et al.
8,337,541 B2 12/2012 Quadri et al.
8,353,953 B2 1/2013 Giannetti et al.
8,398,704 B2 3/2013 Straubinger et al.
8,403,983 B2 3/2013 Quadri et al.
8,414,644 B2 4/2013 Quadri et al.
8,414,645 B2 4/2013 Dwork et al.
8,416,643 B2 4/2013 Magee
8,444,689 B2 5/2013 Zhang
8,449,599 B2 5/2013 Chau et al.
8,454,685 B2 6/2013 Hariton et al.
8,460,368 B2 6/2013 Taylor et al.
8,460,370 B2 6/2013 Zakay et al.
8,470,023 B2 6/2013 Eidenschink et al.
8,470,028 B2 6/2013 Thornton et al.
8,475,521 B2 7/2013 Suri et al.
8,475,523 B2 7/2013 Duffy
8,479,380 B2 7/2013 Malewicz et al.
8,491,650 B2 7/2013 Wiemeyer et al.
8,500,733 B2 8/2013 Watson
8,500,798 B2 8/2013 Rowe et al.
8,511,244 B2 8/2013 Holecek et al.
8,512,401 B2 8/2013 Murray et al.
8,518,096 B2 8/2013 Nelson
8,518,106 B2 8/2013 Duffy et al.
8,562,663 B2 10/2013 Mearns et al.
8,579,963 B2 11/2013 Tabor
8,579,964 B2 11/2013 Lane et al.
8,591,570 B2 11/2013 Revuelta et al.
8,617,236 B2 12/2013 Paul et al.
8,640,521 B2 2/2014 Righini et al.
8,647,381 B2 2/2014 Essinger et al.
8,652,145 B2 2/2014 Maimon et al.
8,652,201 B2 2/2014 Oberti et al.
8,652,202 B2 2/2014 Alon et al.
8,652,203 B2 2/2014 Quadri et al.
8,668,733 B2 3/2014 Haug et al.
8,679,174 B2 3/2014 Ottma et al.
8,679,404 B2 3/2014 Liburd et al.
8,685,086 B2 4/2014 Navia et al.
8,721,708 B2 5/2014 Sèguin et al.
8,721,714 B2 5/2014 Kelley
8,728,154 B2 5/2014 Alkhatib
8,728,155 B2 5/2014 Montorfano et al.
8,740,974 B2 6/2014 Lambrecht et al.
8,740,976 B2 6/2014 Tran et al.
8,747,458 B2 6/2014 Tuval et al.
8,747,459 B2 6/2014 Nguyen et al.
8,758,432 B2 6/2014 Solem
8,764,818 B2 7/2014 Gregg
8,771,344 B2 7/2014 Tran et al.
8,778,020 B2 7/2014 Gregg et al.
8,784,337 B2 7/2014 Voeller et al.
8,784,478 B2 7/2014 Tuval et al.
8,784,481 B2 7/2014 Alkhatib et al.
8,790,387 B2 7/2014 Nguyen et al.
8,795,357 B2 8/2014 Yohanan et al.

(56) References Cited

U.S. PATENT DOCUMENTS 8,808,356 B2 8/2014 Braido et al.
8,828,078 B2 9/2014 Salahieh et al.
8,828,079 B2 9/2014 Thielen et al.
8,834,564 B2 9/2014 Tuval et al.
8,858,620 B2 10/2014 Salahieh et al.
8,870,948 B1 10/2014 Erzberger et al.
8,870,950 B2 10/2014 Hacohen
8,876,893 B2 11/2014 Dwork et al.
8,911,455 B2 12/2014 Quadri et al.
8,926,693 B2 1/2015 Duffy et al.
8,926,694 B2 1/2015 Costello
8,939,960 B2 1/2015 Rosenman et al.
8,945,209 B2 2/2015 Bonyuet et al.
8,961,593 B2 2/2015 Bonhoeffer et al.
8,961,595 B2 2/2015 Alkhatib
8,974,524 B2 3/2015 Yeung et al.
8,979,922 B2 3/2015 Jayasinghe et al.
8,986,375 B2 3/2015 Garde et al.
8,998,980 B2 4/2015 Shipley et al.
9,005,273 B2 4/2015 Salahieh et al.
9,011,521 B2 4/2015 Haug et al.
9,011,523 B2 4/2015 Seguin
9,011,524 B2 4/2015 Eberhardt
9,028,545 B2 5/2015 Taylor
9,034,032 B2 5/2015 McLean et al.
9,055,937 B2 6/2015 Rowe et al.
9,066,801 B2 6/2015 Kovalsky et al.
9,078,749 B2 7/2015 Lutter et al.
9,078,751 B2 7/2015 Naor
9,125,738 B2 9/2015 Figulla et al.
9,173,737 B2 11/2015 Hill et al.
9,180,004 B2 11/2015 Alkhatib
9,186,249 B2 11/2015 Rolando et al.
9,277,990 B2 3/2016 Klima et al.
9,277,993 B2 3/2016 Gamarra et al.
9,289,291 B2 3/2016 Gorman et al.
9,295,551 B2 3/2016 Straubinger et al.
9,445,897 B2 9/2016 Bishop et al.
9,456,877 B2 10/2016 Weitzner et al.
9,681,968 B2 6/2017 Goetz et al.
9,687,345 B2 6/2017 Rabito et al.
9,700,329 B2 7/2017 Metzger et al.
9,700,411 B2 7/2017 Klima et al.
9,724,083 B2 8/2017 Quadri et al.
9,730,790 B2 8/2017 Quadri et al.
9,730,791 B2 8/2017 Ratz et al.
9,795,479 B2 10/2017 Lim et al.
9,833,313 B2 12/2017 Board et al.
9,861,473 B2 1/2018 Lafontaine
9,861,476 B2 1/2018 Salahieh et al.
9,861,477 B2 1/2018 Backus et al.
9,867,698 B2 1/2018 Kovalsky et al.
9,877,830 B2 1/2018 Lim et al.
9,889,029 B2 2/2018 Li et al.
9,895,225 B2 2/2018 Rolando et al.
9,925,045 B2 3/2018 Creaven et al.
10,004,599 B2 6/2018 Rabito et al.
10,117,744 B2 11/2018 Ratz et al.
10,179,044 B2 1/2019 Ratz et al.
10,219,897 B2 3/2019 Essinger et al.
10,350,065 B2 7/2019 Quadri
10,350,066 B2 7/2019 Cooper et al.
10,376,363 B2 8/2019 Quadri et al.
10,555,809 B2 2/2020 Hastings et al.
10,575,951 B2 3/2020 Johnson et al.
10,583,000 B2 3/2020 Ratz et al.
10,639,146 B2 5/2020 Quadri et al.
10,695,177 B2 6/2020 Hariton et al.
10,758,344 B2 9/2020 Hariton et al.
11,406,499 B2 8/2022 Zhang et al.
11,452,598 B2 9/2022 Essinger et al.
11,672,658 B2 6/2023 Hariton et al.
11,701,225 B2 7/2023 Hammer et al.
11,903,829 B1 2/2024 Ma et al.
2001/0021872 A1 9/2001 Bailey et al.
2002/0032481 A1 3/2002 Gabbay
2002/0045929 A1 4/2002 Diaz
2002/0052644 A1 5/2002 Shaolian et al.
2002/0107565 A1 8/2002 Greenhalgh
2002/0123802 A1 9/2002 Snyders
2002/0173842 A1 11/2002 Buchanan
2003/0050694 A1 3/2003 Yang et al.
2003/0100939 A1 5/2003 Yodfat et al.
2003/0105517 A1 6/2003 White et al.
2003/0114913 A1 6/2003 Spenser et al.
2003/0120333 A1 6/2003 Ouriel et al.
2003/0130729 A1 7/2003 Paniagua et al.
2003/0149477 A1 8/2003 Gabbay
2003/0149478 A1 8/2003 Figulla et al.
2003/0158597 A1 8/2003 Quiachon et al.
2003/0176914 A1 9/2003 Rabkin et al.
2003/0199971 A1 10/2003 Tower et al.
2003/0212454 A1 11/2003 Scott et al.
2003/0220683 A1 11/2003 Minasian et al.
2004/0039436 A1 2/2004 Spenser et al.
2004/0092858 A1 5/2004 Wilson et al.
2004/0093075 A1 5/2004 Kuehne
2004/0117009 A1 6/2004 Cali et al.
2004/0133263 A1 7/2004 Dusbabek et al.
2004/0133273 A1 7/2004 Cox
2004/0186563 A1 9/2004 Lobbi
2004/0186565 A1 9/2004 Schreck
2004/0210307 A1 10/2004 Khairkhahan
2004/0215325 A1 10/2004 Penn et al.
2004/0225353 A1 11/2004 McGuckin et al.
2004/0236411 A1 11/2004 Sarac et al.
2004/0260389 A1 12/2004 Case et al.
2005/0033398 A1 2/2005 Seguin
2005/0075727 A1 4/2005 Wheatley
2005/0090887 A1 4/2005 Pryor
2005/0096738 A1 5/2005 Cali et al.
2005/0107872 A1 5/2005 Mensah et al.
2005/0137682 A1 6/2005 Justino
2005/0137686 A1 6/2005 Salahieh et al.
2005/0137687 A1 6/2005 Salahieh et al.
2005/0137688 A1 6/2005 Salahieh et al.
2005/0137691 A1 6/2005 Salahieh et al.
2005/0137698 A1 6/2005 Salahieh et al.
2005/0159811 A1 7/2005 Lane
2005/0182486 A1 8/2005 Gabbay
2005/0203614 A1 9/2005 Forster et al.
2005/0203617 A1 9/2005 Forster et al.
2005/0216079 A1 9/2005 MaCoviak
2005/0234546 A1 10/2005 Nugent et al.
2005/0288766 A1 12/2005 Plain et al.
2006/0020327 A1 1/2006 Lashinski et al.
2006/0025857 A1 2/2006 Bergheim et al.
2006/0058872 A1 3/2006 Salahieh et al.
2006/0095115 A1 5/2006 Bladillah et al.
2006/0142837 A1 6/2006 Haverkost et al.
2006/0149350 A1 7/2006 Patel et al.
2006/0161249 A1 7/2006 Realyvasquez et al.
2006/0173537 A1 8/2006 Yang et al.
2006/0195134 A1 8/2006 Crittenden
2006/0195183 A1 8/2006 Navia et al.
2006/0212110 A1 9/2006 Osborne et al.
2006/0229719 A1 10/2006 Marquez et al.
2006/0241745 A1 10/2006 Solem
2006/0259135 A1 11/2006 Navia et al.
2006/0259137 A1 11/2006 Artof et al.
2006/0276874 A1 12/2006 Wilson et al.
2006/0293745 A1 12/2006 Carpentier et al.
2007/0005131 A1 1/2007 Taylor
2007/0010877 A1 1/2007 Salahieh et al.
2007/0027534 A1 2/2007 Bergheim et al.
2007/0043435 A1 2/2007 Seguin et al.
2007/0050021 A1 3/2007 Johnson
2007/0066863 A1 3/2007 Rafiee et al.
2007/0088431 A1 4/2007 Bourang et al.
2007/0100432 A1 5/2007 Case et al.
2007/0100439 A1 5/2007 Cangialosi et al.
2007/0112422 A1 5/2007 Dehdashtian
2007/0129794 A1 6/2007 Realyvasquez
2007/0142906 A1 6/2007 Figulla et al.

(56) References Cited

U.S. PATENT DOCUMENTS

| | | | |
|---|---|---|---|
| 2007/0156224 | A1 | 7/2007 | Cioanta et al. |
| 2007/0203503 | A1 | 8/2007 | Salahieh et al. |
| 2007/0203575 | A1 | 8/2007 | Forster et al. |
| 2007/0213813 | A1 | 9/2007 | Von Segesser et al. |
| 2007/0244552 | A1 | 10/2007 | Salahieh et al. |
| 2007/0255394 | A1 | 11/2007 | Ryan |
| 2007/0270943 | A1 | 11/2007 | Solem et al. |
| 2008/0021546 | A1 | 1/2008 | Patz et al. |
| 2008/0065011 | A1 | 3/2008 | Marchand et al. |
| 2008/0071361 | A1 | 3/2008 | Tuval et al. |
| 2008/0071362 | A1 | 3/2008 | Tuval et al. |
| 2008/0071363 | A1 | 3/2008 | Tuval et al. |
| 2008/0071366 | A1 | 3/2008 | Tuval et al. |
| 2008/0071368 | A1 | 3/2008 | Tuval et al. |
| 2008/0071369 | A1 | 3/2008 | Tuval et al. |
| 2008/0082164 | A1 | 4/2008 | Friedman |
| 2008/0082165 | A1 | 4/2008 | Wilson et al. |
| 2008/0082166 | A1 | 4/2008 | Styrc et al. |
| 2008/0097581 | A1 | 4/2008 | Shanley |
| 2008/0114442 | A1 | 5/2008 | Mitchell et al. |
| 2008/0125853 | A1 | 5/2008 | Bailey et al. |
| 2008/0147179 | A1 | 6/2008 | Cai et al. |
| 2008/0147183 | A1 | 6/2008 | Styrc |
| 2008/0154355 | A1 | 6/2008 | Benichou et al. |
| 2008/0161910 | A1 | 7/2008 | Revuelta et al. |
| 2008/0177381 | A1 | 7/2008 | Navia et al. |
| 2008/0183273 | A1 | 7/2008 | Mesana et al. |
| 2008/0208328 | A1 | 8/2008 | Antocci et al. |
| 2008/0208332 | A1 | 8/2008 | Lamphere et al. |
| 2008/0221672 | A1 | 9/2008 | Lamphere et al. |
| 2008/0228254 | A1 | 9/2008 | Ryan |
| 2008/0255660 | A1 | 10/2008 | Guyenot et al. |
| 2008/0255661 | A1 | 10/2008 | Straubinger et al. |
| 2008/0281411 | A1 | 11/2008 | Berreklouw |
| 2009/0005863 | A1 | 1/2009 | Goetz et al. |
| 2009/0054968 | A1 | 2/2009 | Bonhoeffer et al. |
| 2009/0054974 | A1 | 2/2009 | McGuckin et al. |
| 2009/0076598 | A1 | 3/2009 | Salahieh et al. |
| 2009/0112309 | A1 | 4/2009 | Jaramillo et al. |
| 2009/0138079 | A1 | 5/2009 | Tuval et al. |
| 2009/0157175 | A1 | 6/2009 | Benichou |
| 2009/0164005 | A1 | 6/2009 | Dove et al. |
| 2009/0171432 | A1 | 7/2009 | Von Segesser et al. |
| 2009/0171447 | A1 | 7/2009 | Von Segesser et al. |
| 2009/0171456 | A1 | 7/2009 | Kveen et al. |
| 2009/0182413 | A1 | 7/2009 | Burkart et al. |
| 2009/0188964 | A1 | 7/2009 | Orlov |
| 2009/0216310 | A1 | 8/2009 | Straubinger et al. |
| 2009/0216313 | A1 | 8/2009 | Straubinger et al. |
| 2009/0216322 | A1 | 8/2009 | Le et al. |
| 2009/0222076 | A1 | 9/2009 | Figulla et al. |
| 2009/0234443 | A1 | 9/2009 | Ottma et al. |
| 2009/0240320 | A1 | 9/2009 | Tuval et al. |
| 2009/0270972 | A1 | 10/2009 | Lane |
| 2009/0276027 | A1 | 11/2009 | Glynn |
| 2009/0276040 | A1 | 11/2009 | Rowe et al. |
| 2009/0281618 | A1 | 11/2009 | Hill et al. |
| 2009/0281619 | A1 | 11/2009 | Le et al. |
| 2009/0287296 | A1 | 11/2009 | Manasse |
| 2009/0287299 | A1 | 11/2009 | Tabor et al. |
| 2009/0292350 | A1 | 11/2009 | Eberhardt et al. |
| 2009/0306768 | A1 | 12/2009 | Quadri |
| 2009/0319037 | A1 | 12/2009 | Rowe et al. |
| 2010/0016958 | A1 | 1/2010 | St. Goar et al. |
| 2010/0024818 | A1 | 2/2010 | Stenzler et al. |
| 2010/0049313 | A1 | 2/2010 | Alon et al. |
| 2010/0069852 | A1 | 3/2010 | Kelley |
| 2010/0114305 | A1 | 5/2010 | Kang et al. |
| 2010/0131054 | A1 | 5/2010 | Tuval et al. |
| 2010/0137979 | A1 | 6/2010 | Tuval et al. |
| 2010/0145438 | A1 | 6/2010 | Barone |
| 2010/0174362 | A1 | 7/2010 | Straubinger et al. |
| 2010/0191326 | A1 | 7/2010 | Alkhatib |
| 2010/0204781 | A1 | 8/2010 | Alkhatib |
| 2010/0217382 | A1 | 8/2010 | Chau et al. |
| 2010/0249894 | A1 | 9/2010 | Oba et al. |
| 2010/0249911 | A1 | 9/2010 | Alkhatib |
| 2010/0256723 | A1 | 10/2010 | Murray |
| 2010/0262231 | A1 | 10/2010 | Tuval et al. |
| 2010/0305685 | A1 | 12/2010 | Millwee et al. |
| 2010/0312333 | A1 | 12/2010 | Navia et al. |
| 2011/0015616 | A1 | 1/2011 | Straubinger et al. |
| 2011/0015729 | A1 | 1/2011 | Jimenez et al. |
| 2011/0029072 | A1 | 2/2011 | Gabbay |
| 2011/0137397 | A1 | 6/2011 | Chau et al. |
| 2011/0178597 | A9 | 7/2011 | Navia et al. |
| 2011/0208290 | A1 | 8/2011 | Straubinger et al. |
| 2011/0208297 | A1 | 8/2011 | Tuval et al. |
| 2011/0208298 | A1 | 8/2011 | Tuval et al. |
| 2011/0224785 | A1 | 9/2011 | Hacohen |
| 2011/0238159 | A1 | 9/2011 | Guyenot et al. |
| 2011/0264196 | A1 | 10/2011 | Savage et al. |
| 2011/0264198 | A1 | 10/2011 | Murray et al. |
| 2011/0288634 | A1 | 11/2011 | Tuval et al. |
| 2011/0313515 | A1 | 12/2011 | Quadri et al. |
| 2011/0319989 | A1 | 12/2011 | Lane et al. |
| 2012/0022639 | A1 | 1/2012 | Hacohen et al. |
| 2012/0035722 | A1 | 2/2012 | Tuval |
| 2012/0041550 | A1 | 2/2012 | Salahieh et al. |
| 2012/0046741 | A1 | 2/2012 | Tuval et al. |
| 2012/0046742 | A1 | 2/2012 | Tuval et al. |
| 2012/0078360 | A1 | 3/2012 | Rafiee |
| 2012/0101570 | A1 | 4/2012 | Tuval et al. |
| 2012/0101571 | A1 | 4/2012 | Thambar et al. |
| 2012/0101572 | A1 | 4/2012 | Kovalsky et al. |
| 2012/0123529 | A1 | 5/2012 | Levi et al. |
| 2012/0185039 | A1 | 7/2012 | Tuval et al. |
| 2012/0197386 | A1 | 8/2012 | Von Segesser et al. |
| 2012/0209374 | A1 | 8/2012 | Bonhoeffer et al. |
| 2012/0215303 | A1 | 8/2012 | Quadri et al. |
| 2012/0239142 | A1 | 9/2012 | Liu et al. |
| 2012/0271398 | A1 | 10/2012 | Essinger et al. |
| 2012/0283823 | A1 | 11/2012 | Bonhoeffer et al. |
| 2012/0290062 | A1 | 11/2012 | McNamara et al. |
| 2012/0296418 | A1 | 11/2012 | Bonyuet et al. |
| 2012/0310328 | A1 | 12/2012 | Olson et al. |
| 2012/0310336 | A1 | 12/2012 | Figulla et al. |
| 2013/0006294 | A1 | 1/2013 | Kashkarov et al. |
| 2013/0035759 | A1 | 2/2013 | Gross et al. |
| 2013/0073035 | A1 | 3/2013 | Tuval et al. |
| 2013/0079869 | A1 | 3/2013 | Straubinger et al. |
| 2013/0172992 | A1 | 7/2013 | Gross et al. |
| 2013/0190861 | A1 | 7/2013 | Chau et al. |
| 2013/0190862 | A1 | 7/2013 | Pintor et al. |
| 2013/0197622 | A1 | 8/2013 | Mitra et al. |
| 2013/0211508 | A1 | 8/2013 | Lane et al. |
| 2013/0253635 | A1 | 9/2013 | Straubinger et al. |
| 2013/0253642 | A1 | 9/2013 | Brecker |
| 2013/0310928 | A1 | 11/2013 | Morriss et al. |
| 2013/0331929 | A1 | 12/2013 | Mitra et al. |
| 2013/0338766 | A1 | 12/2013 | Hastings et al. |
| 2013/0345786 | A1 | 12/2013 | Behan |
| 2014/0018912 | A1 | 1/2014 | Delaloye et al. |
| 2014/0025163 | A1 | 1/2014 | Padala et al. |
| 2014/0039611 | A1 | 2/2014 | Lane et al. |
| 2014/0052237 | A1 | 2/2014 | Lane et al. |
| 2014/0100651 | A1 | 4/2014 | Kheradvar et al. |
| 2014/0163668 | A1 | 6/2014 | Rafiee |
| 2014/0172077 | A1 | 6/2014 | Bruchman et al. |
| 2014/0172083 | A1 | 6/2014 | Bruchman et al. |
| 2014/0194981 | A1 | 7/2014 | Menk et al. |
| 2014/0207231 | A1 | 7/2014 | Hacohen et al. |
| 2014/0214157 | A1 | 7/2014 | Börtlein et al. |
| 2014/0222136 | A1 | 8/2014 | Geist et al. |
| 2014/0222139 | A1 | 8/2014 | Nguyen et al. |
| 2014/0222142 | A1 | 8/2014 | Kovalsky et al. |
| 2014/0222144 | A1 | 8/2014 | Eberhardt et al. |
| 2014/0243966 | A1 | 8/2014 | Garde et al. |
| 2014/0257467 | A1 | 9/2014 | Lane et al. |
| 2014/0277390 | A1 | 9/2014 | Ratz et al. |
| 2014/0277403 | A1 | 9/2014 | Peter |
| 2014/0277412 | A1 | 9/2014 | Börtlein et al. |
| 2014/0277422 | A1 | 9/2014 | Ratz et al. |
| 2014/0277426 | A1 | 9/2014 | Dakin et al. |

(56) References Cited

U.S. PATENT DOCUMENTS

2014/0277427 A1 9/2014 Ratz et al.
2014/0296973 A1 10/2014 Bergheim et al.
2014/0296975 A1 10/2014 Tegels et al.
2014/0303719 A1 10/2014 Cox et al.
2014/0309728 A1 10/2014 Dehdashtian et al.
2014/0324160 A1 10/2014 Benichou et al.
2014/0324164 A1 10/2014 Gross et al.
2014/0330368 A1 11/2014 Gloss et al.
2014/0330371 A1 11/2014 Gloss et al.
2014/0330372 A1 11/2014 Weston et al.
2014/0336754 A1 11/2014 Gurskis et al.
2014/0343669 A1 11/2014 Lane et al.
2014/0343670 A1 11/2014 Bakis et al.
2014/0350666 A1 11/2014 Righini
2014/0350668 A1 11/2014 Delaloye et al.
2014/0358223 A1 12/2014 Rafiee et al.
2014/0364939 A1 12/2014 Deshmukh et al.
2014/0364943 A1 12/2014 Conklin
2014/0371842 A1 12/2014 Marquez et al.
2014/0371844 A1 12/2014 Dale et al.
2014/0371847 A1 12/2014 Madrid et al.
2014/0371848 A1 12/2014 Murray et al.
2015/0005863 A1 1/2015 Para
2015/0018944 A1 1/2015 O'Connell et al.
2015/0039083 A1 2/2015 Rafiee
2015/0142100 A1 5/2015 Morriss et al.
2015/0142103 A1 5/2015 Vidlund
2015/0148731 A1 5/2015 Mcnamara et al.
2015/0173897 A1 6/2015 Raanani et al.
2015/0196390 A1 7/2015 Ma et al.
2015/0209141 A1 7/2015 Braido et al.
2015/0272737 A1 10/2015 Dale et al.
2015/0297346 A1 10/2015 Duffy et al.
2015/0335429 A1 11/2015 Morriss et al.
2015/0351903 A1 12/2015 Morriss et al.
2015/0359629 A1 12/2015 Ganesan et al.
2016/0000591 A1 1/2016 Lei et al.
2016/0030169 A1 2/2016 Shahriari
2016/0030170 A1 2/2016 Alkhatib et al.
2016/0030171 A1 2/2016 Quijano et al.
2016/0038280 A1 2/2016 Morriss et al.
2016/0038281 A1 2/2016 Delaloye et al.
2016/0074160 A1 3/2016 Christianson et al.
2016/0106537 A1 4/2016 Christianson et al.
2016/0113765 A1 4/2016 Ganesan et al.
2016/0113768 A1 4/2016 Ganesan et al.
2016/0143732 A1 5/2016 Glimsdale
2016/0158010 A1 6/2016 Lim et al.
2016/0166383 A1 6/2016 Lim et al.
2016/0184097 A1 6/2016 Lim et al.
2016/0199206 A1 7/2016 Lim et al.
2016/0213473 A1 7/2016 Hacohen et al.
2016/0235529 A1 8/2016 Ma et al.
2016/0278923 A1 9/2016 Krans et al.
2016/0279386 A1 9/2016 Dale et al.
2016/0310267 A1 10/2016 Zeng et al.
2017/0042678 A1 2/2017 Ganesan et al.
2017/0079785 A1 3/2017 Li
2017/0128209 A1 5/2017 Morriss et al.
2017/0216023 A1 8/2017 Lane et al.
2017/0216575 A1 8/2017 Asleson et al.
2017/0257902 A1 9/2017 Xing et al.
2017/0258614 A1 9/2017 Griffin
2017/0325945 A1 11/2017 Dale et al.
2017/0325954 A1 11/2017 Perszyk
2017/0333186 A1 11/2017 Spargias
2017/0348096 A1 12/2017 Anderson
2017/0367821 A1 12/2017 Landon et al.
2017/0367823 A1 12/2017 Hariton et al.
2018/0014931 A1 1/2018 Morriss et al.
2018/0021129 A1 1/2018 Peterson et al.
2018/0055629 A1 3/2018 Oba et al.
2018/0055636 A1 3/2018 Valencia et al.
2018/0085218 A1 3/2018 Eidenschink
2018/0110534 A1 4/2018 Gavala et al.
2018/0110622 A1 4/2018 Gregg et al.
2018/0116790 A1 5/2018 Ratz et al.
2018/0126119 A1 5/2018 McNiven et al.
2018/0147061 A1 5/2018 Drasler et al.
2018/0296341 A1 10/2018 Noe et al.
2018/0344457 A1 12/2018 Gross et al.
2018/0344490 A1 12/2018 Fox et al.
2019/0008639 A1 1/2019 Landon et al.
2019/0008640 A1 1/2019 Cooper et al.
2019/0060072 A1 2/2019 Zeng
2019/0262129 A1 8/2019 Cooper et al.
2020/0000579 A1 1/2020 Manash et al.
2020/0038180 A1 2/2020 Oba et al.
2020/0108225 A1 4/2020 Jamal et al.
2020/0138572 A1 5/2020 Zhao et al.
2020/0163761 A1 5/2020 Hariton et al.
2020/0323668 A1 10/2020 Diedering et al.
2020/0345494 A1 11/2020 Srinimukesh et al.
2020/0352718 A1 11/2020 Rowe et al.
2021/0015615 A1 1/2021 Groothuis et al.
2021/0145576 A1 5/2021 Becerra et al.
2021/0228354 A1 7/2021 Rafiee et al.
2021/0259835 A1 8/2021 Tyler, II et al.
2021/0307900 A1 10/2021 Hacohen
2021/0378817 A1 12/2021 Nia et al.
2021/0386544 A1 12/2021 Cooper et al.
2022/0142777 A1 5/2022 Scheinblum et al.
2022/0287836 A1 9/2022 Landon et al.
2022/0346993 A1 11/2022 Srinimukesh et al.
2023/0000624 A1 1/2023 Okabe et al.
2023/0200980 A1 6/2023 Peterson et al.
2023/0218391 A1 7/2023 Dass et al.
2023/0380963 A1 11/2023 Kaufman et al.
2023/0390052 A1 12/2023 Okafor et al.
2023/0404753 A1 12/2023 Luong et al.
2024/0008978 A1 1/2024 Nawalakhe et al.
2024/0091000 A1 3/2024 King et al.

FOREIGN PATENT DOCUMENTS

DE 19532846 A1 3/1997
DE 19546692 A1 6/1997
DE 19857887 A1 7/2000
DE 19907646 A1 8/2000
DE 10049812 A1 4/2002
DE 10049813 C1 4/2002
DE 10049814 A1 4/2002
DE 10049815 A1 4/2002
DE 10010074 B4 4/2005
DE 102006052564 B3 12/2007
EP 0144167 A2 6/1985
EP 0103546 B1 5/1988
EP 0592410 B1 10/1995
EP 0850607 A1 7/1998
EP 0597967 B1 12/1999
EP 1057460 A1 12/2000
EP 1088529 A2 4/2001
EP 1469797 A1 10/2004
EP 1259194 B1 2/2005
EP 1171059 B1 11/2005
EP 1255510 B1 4/2007
EP 1239901 B1 10/2007
EP 1849440 A1 10/2007
EP 1570809 B1 1/2009
EP 1472996 B1 9/2009
EP 1653888 B1 9/2009
EP 1935377 B1 3/2010
EP 1369098 B1 4/2014
EP 2124826 B1 7/2014
EP 2745805 B1 6/2015
EP 2749254 B1 6/2015
EP 2918249 A2 9/2015
EP 2168536 B1 4/2016
EP 2413842 B1 8/2017
EP 2446915 B1 1/2018
EP 3057541 B1 1/2018
EP 3037064 B1 3/2018
EP 3046511 B1 3/2018
EP 3142603 B1 3/2018

(56) References Cited

FOREIGN PATENT DOCUMENTS

| | | | |
|---|---|---|---|
| EP | 3075354 | B1 | 11/2018 |
| EP | 3184083 | B1 | 2/2019 |
| EP | 2918249 | B1 | 4/2020 |
| EP | 3417813 | B1 | 5/2020 |
| EP | 2777616 | B1 | 8/2020 |
| EP | 3139864 | B1 | 11/2020 |
| EP | 2750630 | B1 | 6/2021 |
| EP | 2777617 | B1 | 9/2022 |
| EP | 2948103 | B1 | 12/2022 |
| EP | 2967858 | B1 | 1/2023 |
| EP | 3570779 | B1 | 2/2023 |
| EP | 3294220 | B1 | 12/2023 |
| FR | 2788217 | A1 | 7/2000 |
| GB | 1264471 | A | 2/1972 |
| GB | 1315844 | A | 5/1973 |
| GB | 2056023 | A | 3/1981 |
| GB | 2398245 | A | 8/2004 |
| SU | 1271508 | A1 | 11/1986 |
| WO | 1991016041 | A1 | 10/1991 |
| WO | 1991017720 | A1 | 11/1991 |
| WO | 1992017118 | A1 | 10/1992 |
| WO | 1993001768 | A1 | 2/1993 |
| WO | 1997024080 | A1 | 7/1997 |
| WO | 1998029057 | A1 | 7/1998 |
| WO | 1999033414 | A1 | 7/1999 |
| WO | 1999040964 | A1 | 8/1999 |
| WO | 1999047075 | A1 | 9/1999 |
| WO | 2000018333 | A1 | 4/2000 |
| WO | 2000041652 | A1 | 7/2000 |
| WO | 2000047139 | A1 | 8/2000 |
| WO | 2000061034 | A1 | 10/2000 |
| WO | 2001028459 | A1 | 4/2001 |
| WO | 2001035878 | A2 | 5/2001 |
| WO | 2001049213 | A2 | 7/2001 |
| WO | 2001054624 | A1 | 8/2001 |
| WO | 2001054625 | A1 | 8/2001 |
| WO | 2001062189 | A1 | 8/2001 |
| WO | 2001064137 | A1 | 9/2001 |
| WO | 2001076510 | A2 | 10/2001 |
| WO | 2002036048 | A1 | 5/2002 |
| WO | WO-2002041789 | A2 | 5/2002 |
| WO | 2003047468 | A1 | 6/2003 |
| WO | 2003092554 | A1 | 11/2003 |
| WO | 2004030569 | A2 | 4/2004 |
| WO | 2005011534 | A1 | 2/2005 |
| WO | 2005034812 | A1 | 4/2005 |
| WO | WO-2005062980 | A2 | 7/2005 |
| WO | 2005087140 | A1 | 9/2005 |
| WO | 2005102015 | A2 | 11/2005 |
| WO | 2006014233 | A2 | 2/2006 |
| WO | 2006034008 | A2 | 3/2006 |
| WO | 2006085225 | A1 | 8/2006 |
| WO | 2006108090 | A2 | 10/2006 |
| WO | 2006111391 | A1 | 10/2006 |
| WO | 2006138173 | A2 | 12/2006 |
| WO | 2007025028 | A1 | 3/2007 |
| WO | 2008005405 | A2 | 1/2008 |
| WO | 2008035337 | A2 | 3/2008 |
| WO | 2008125153 | A1 | 10/2008 |
| WO | 2008147964 | A1 | 12/2008 |
| WO | 2008150529 | A1 | 12/2008 |
| WO | 2009024859 | A2 | 2/2009 |
| WO | 2009026563 | A2 | 2/2009 |
| WO | 2009042196 | A2 | 4/2009 |
| WO | 2009091509 | A1 | 7/2009 |
| WO | 2009094500 | A1 | 7/2009 |
| WO | 2010005524 | A2 | 1/2010 |
| WO | 2010008549 | A1 | 1/2010 |
| WO | 2010121076 | A2 | 10/2010 |
| WO | 2011002996 | A2 | 1/2011 |
| WO | 2011081997 | A1 | 7/2011 |
| WO | 2012032187 | A1 | 3/2012 |
| WO | 2012095455 | A2 | 7/2012 |
| WO | 2013028387 | A2 | 2/2013 |
| WO | 2013106585 | A1 | 7/2013 |
| WO | 2014018432 | A2 | 1/2014 |
| WO | 2014079291 | A1 | 5/2014 |
| WO | 2014145338 | A1 | 9/2014 |
| WO | 2014149865 | A1 | 9/2014 |
| WO | 2014163706 | A1 | 10/2014 |
| WO | 2014194178 | A1 | 12/2014 |
| WO | 2015057407 | A1 | 4/2015 |
| WO | 2015077274 | A1 | 5/2015 |
| WO | 2016016899 | A1 | 2/2016 |
| WO | 2017035487 | A1 | 3/2017 |
| WO | 2018213209 | A1 | 11/2018 |
| WO | 2022002054 | A1 | 1/2022 |
| WO | 2023006048 | A1 | 2/2023 |
| WO | 2023076103 | A1 | 5/2023 |
| WO | 2023081236 | A1 | 5/2023 |
| WO | 2023091769 | A1 | 5/2023 |
| WO | 2023096804 | A1 | 6/2023 |
| WO | 2023154250 | A1 | 8/2023 |
| WO | 2023196150 | A1 | 10/2023 |
| WO | 2023244454 | A1 | 12/2023 |
| WO | 2023244767 | A1 | 12/2023 |
| WO | 2023250114 | A1 | 12/2023 |
| WO | 2024001789 | A1 | 1/2024 |
| WO | 2024003620 | A1 | 1/2024 |
| WO | 2024007575 | A1 | 1/2024 |
| WO | 2024009540 | A1 | 1/2024 |
| WO | 2024010739 | A1 | 1/2024 |
| WO | 2024030520 | A1 | 2/2024 |

OTHER PUBLICATIONS

Andersen, Henning Rud, "History of Percutaneous Aortic Valve Prosthesis," Herz 34 2009 Nr. 5, Urban&Vogel, pp. 343-346, Skejby University Hospital Department of Cardiology, Aarhus, Denmark.

Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.

Inoue, M.D., Kanji, et al., "Clinical Application of Transvenous Mitral Commissurotomy by a New Balloon Catheter," The Journal of Thoracic and Cardiovascular Surgery 87:394-402, 1984.

Pavcnik, M.D., Ph.D., Dusan, et al. "Development and Initial Experimental Evaluation of a Prosthetic Aortic Valve for Transcatheter Placement," Cardiovascular Radiology 1992; 183:151-154.

Rashkind, M.D., William J., "Historical Aspects of Interventional Cardiology: Past, Present, Future," Texas Heart Institute Journal, Interventional Cardiology, pp. 363-367.

Rösch, M.D., Josef, "The Birth, Early Years and Future of Interventional Radiology," J Vasc Interv Radiol 2003; 14:841-853.

Ross, F.R.C.S., D.N., "Aortic Valve Surgery," Guy's Hospital, London, pp. 192-197, approximately 1968.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Wheatley, M.D., David J., "Valve Prostheses," Rob&Smith's Operative Surgery, Fourth Edition, pp. 415-424, Butterworths 1986.

Bavaria, Joseph E. M.D et al.: "Transcatheter Mitral Valve Implantation: The Future Gold Standard for MR?".

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409.

Bavaria, Joseph E. M.D.: "CardiAQ Valve Technologies: Transcatheter Mitral Valve Implantation," Sep. 21, 2009.

Berreklouw, Eric, PhD, et al., "Sutureless Mitral Valve Replacement With Bioprostheses and Nitinol Attachment Rings: Feasibility in Acute Pig Experiments," The Journal of Thoracic and Cardiovascular Surgery, vol. 142, No. 2, Aug. 2011 in 7 pages.

Boudjemline, Younes, et al., "Steps Toward the Percutaneous Replacement of Atrioventricular Valves," JACC, vol. 46, No. 2, Jul. 19, 2005:360-5.

CardiAQ Valve Technologies, "Innovations in Heart Valve Therapy," In3 San Francisco, Jun. 18, 2008, PowerPoint presentation in 19 slides.

(56) References Cited

OTHER PUBLICATIONS

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.
Condado, Jose Antonio, et al., "Percutaneous Treatment of Heart Valves," Rev Esp Cardio. 2006;59(12):1225-31.
Feldman, Ted, MD. "Prospects for Percutaneous Valve Therapies," Circulation 2007;116:2866-2877.
Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA.
Fornell, Dave, "Transcatheter Mitral Valve replacement Devices in Development," Diagnostic and Interventional Cardiology, Dec. 30, 2014, p. 3, <http://www.dicardiology.com/article/transcatheter-mitral-valve-replacement-devices-development>.
Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.
Karimi, Houshang, et al., "Percutaneous Valve Therapies," SIS 2007 Yearbook, Chapter 11, pp. 1-11.
Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.
Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages.
Lutter, Georg, et al., "Off-Pump Transapical Mitral Valve Replacement," European Journal of Cardio-thoracic Surgery 36 (2009) 124-128.
Ma, Liang, et al., "'Double-Crowned Valved Stents for Off-Pump Mitral Valve Replacement," European Journal of Cardio-thoracic Surgery 28 (2005) 194-199.
Mack, Michael, M.D., "Antegrade Transcatheter Mitral valve Implantation: A Short-term Experience in Swine Model,".
Mack, Michael, M.D., "Antegrade Transcatheter Mitral valve Implantation: On-Going Experience in Swine Model,".
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Preston-Maher, Georgia L., et al., "A Technical Review of Minimally Invasive Mitral Valve Replacements," Cardiovascular Engineering and Technology, vol. 6, No. 2, Jun. 2015, pp. 174-184.
Quadri, Arshad M.D., "Transcatheter Mitral Valve Implantation (TMVI) (An Acute in Vivo Study),".
Ratz, J. Brent, "LSI EMT Spotlight," May 15, 2009.
Ratz, J. Brent et al., "Any experiences making an expandable stent frame?" Arch-Pub.com, Architecture Forums: Modeling, Multiple forum postings from Feb. 3, 2009 to Feb. 4, 2009, http://www.arch-pub.com.
Ratz, J. Brent, "In3 Company Overview," Jun. 24, 2009.
Ruiz, Carlos E., "Overview of Novel Transcatheter Valve Technologies,".
Spillner, J. et al., "New Sutureless 'Atrial-Mitral-Valve Prosthesis' for Minimally Invasive Mitral Valve Therapy," Textile Research Journal, 2010, in 7 pages.
Sondergaard, Lars, et al., "Transcatheter Mitral Valve Implantation: CardiAQ™," TCT 2013.
Sondergaard, Lars, et al., "Transcatheter Mitral Valve Implantation: CardiAQ™," EuroPCR 2013.
Sondergaard, Lars, "CardiAQ TMVR FIH—Generation 2," TVT symposium.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Webb, John G., et al., "Transcatheter Aortic Valve Implantation: The Evolution of Prostheses, Delivery Systems and Approaches," Archives of Cardiovascular Disease (2012) 105, 153-159.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
"CardiAQ Valve Technologies, Percutaneous Mitral Valve Replacement, Company Overview," at TVT on Jun. 25, 2009.
BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first- in/382370.
BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.
Neovasc corporate presentation, Oct. 2009, available at http://www.neovasc.com/investors/documents/Neovasc-Corporate-Presentation-October-2009.pdf.
Herrmann, Howard C., M.D., "Advances in Transseptal Transcatheter Mitral Valve Replacement," Cardiovascular Research Foundation, tct, Sep. 21-25, 2018, 10 Pages, San Diego, California.
Neale, Todd, "Flushing TAVI Valves With Carbon Dioxide May Protect Against Brain Injury", News Conference News, EuroPCR 2023, TCTMD, May 16, 2023, Paris France.
Transcatheter Aortic Valve Delivery Catheter System Compression Loading System, Medtronic CoreValveSystem, Medtronic Inc, 2014, 61 pages, Santa Ana, California.

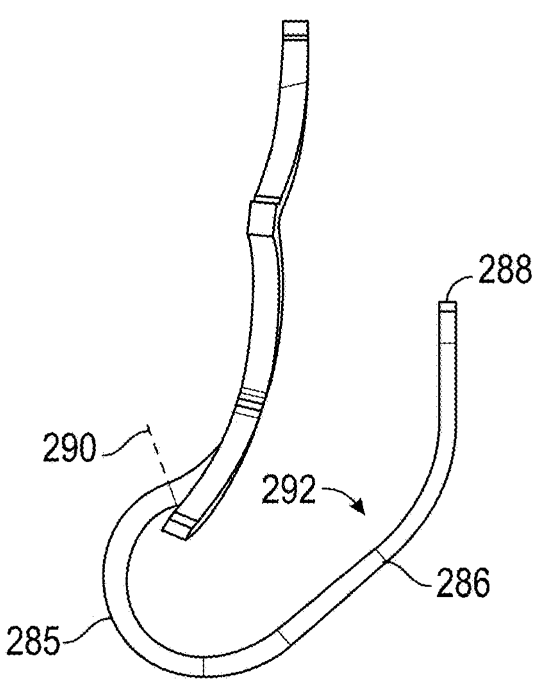
FIG. 55A
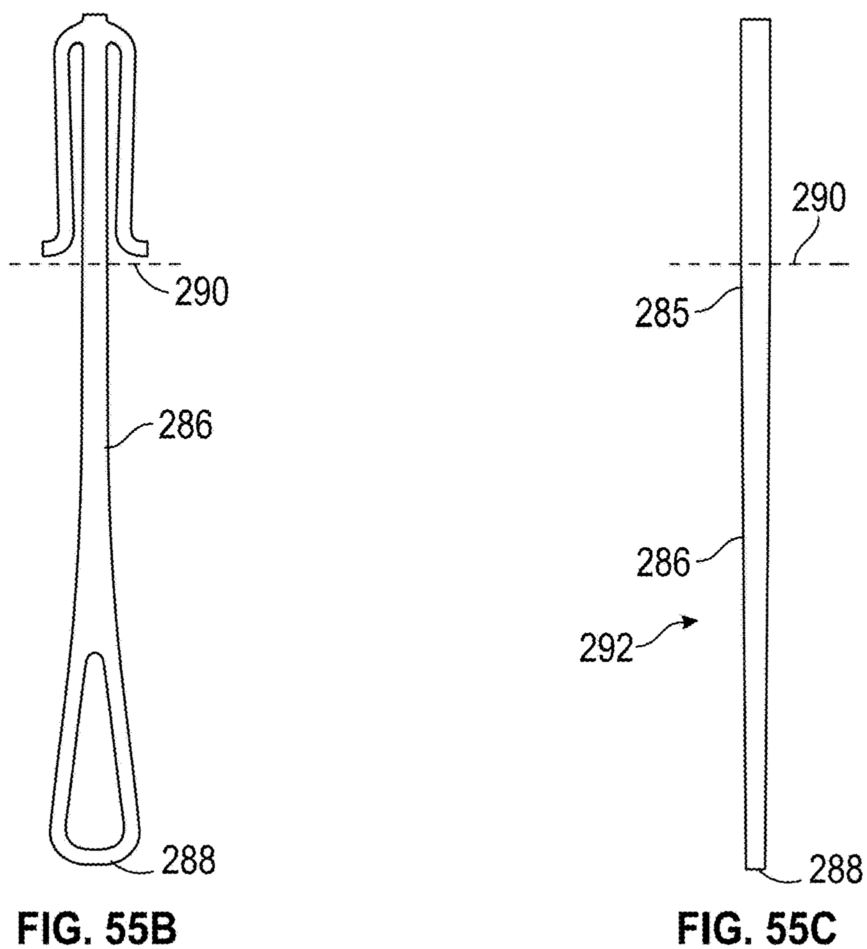
FIG. 55B
FIG. 55C

PROSTHETIC VALVE WITH ENHANCED SEALING

CROSS REFERENCE TO RELATED APPLICATIONS

This application is a continuation of International Application No. PCT/US2021/047000, filed Aug. 20, 2021, which designates the United States and was published in English by the International Bureau on Mar. 3, 2022 as WO2022/046568, which claims priority to U.S. Provisional Application No. 63/199,267, filed Dec. 16, 2020, and U.S. Provisional Application No. 63/071,684, filed Aug. 28, 2020, the entire contents of each of which are hereby incorporated by reference.

BACKGROUND

Field

Certain embodiments disclosed herein relate generally to implants, including prosthetic valves for implantation. In particular, implants relate in some embodiments to prosthetic valves that may reduce the possibility of paravalvular leakage (PVL), among other features.

Background

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

These replacement valves are often intended to at least partially block blood flow. However, a problem occurs when blood flows around the valve on the outside of the prosthesis. For example, in the context of replacement heart valves, paravalvular leakage (PVL) has proven particularly challenging. An additional challenge relates to the ability of such prostheses to be secured relative to intralumenal tissue, e.g., tissue within any body lumen or cavity, in an atraumatic manner.

SUMMARY

Embodiments of prosthetic valves may include sealing bodies configured for an anchor to at least partially pass through. The ability of the anchor to pass through the sealing body may allow the sealing body to seal to a portion of a patient's heart in the event of a missed capture of a leaflet by the anchor. As such, reduced possibility of paravalvular leakage (PVL) may result. The sealing body may comprise an adaptive sealing body configured to adapt locally to a missed capture of a leaflet by the anchor.

Embodiments herein may further include modular valve systems. Such modular valve systems may enhance the variability of the configuration of a prosthetic valve and improve the ability to fabricate such prosthetic valves.

Embodiments herein may further include prosthetic valves including anchors for coupling to chordae, trabeculae, or papillary structures of a patient's heart.

Embodiments herein may further include prosthetic valves including anchors for engaging calcification of the native valve to anchor the prosthetic valve to the native valve.

Embodiments herein may include other features of prosthetic valves.

Embodiments as disclosed herein may include a prosthetic valve configured to be deployed to a native valve. The prosthetic valve may include a plurality of prosthetic valve leaflets. One or more anchors may be coupled to the plurality of prosthetic valve leaflets and each configured to anchor to a portion of a patient's heart. A sealing body may be positioned radially outward of the plurality of prosthetic valve leaflets and configured to abut a portion of the patient's heart to reduce fluid flow, the sealing body configured for the one or more anchors to at least partially pass through in a radially inward direction.

A method may include deploying a prosthetic valve to a native valve of a patient's body. The prosthetic valve may include a plurality of prosthetic valve leaflets. One or more anchors may be coupled to the plurality of prosthetic valve leaflets and each configured to anchor to a portion of a patient's heart. A sealing body may be positioned radially outward of the plurality of prosthetic valve leaflets and configured to abut a portion of the patient's heart to reduce fluid flow, the sealing body configured for the one or more anchors to at least partially pass through in a radially inward direction.

Embodiments as disclosed herein may include a modular prosthetic valve system. The system may comprise a plurality of different configurations of distal anchors. The system may comprise a plurality of different configurations of proximal anchors. The system may comprise a valve body including a plurality of prosthetic valve leaflets and configured to be coupled to one of the configurations of distal anchors selected from the plurality of different configurations of distal anchors, and configured to be coupled to one of the configurations of proximal anchors selected from the plurality of different configurations of proximal anchors.

Embodiments as disclosed herein may include a method of forming a prosthetic valve. The method may include selecting a configuration of distal anchors from a plurality of different configurations of distal anchors. The method may include selecting a configuration of proximal anchors from a plurality of different configurations of proximal anchors. The method may include coupling the selected configuration of distal anchors and the selected configuration of proximal anchors to a valve body including a plurality of prosthetic valve leaflets.

Embodiments as disclosed herein may include a prosthetic valve configured to be deployed to a native valve. The valve may include a plurality of prosthetic valve leaflets. The valve may include a frame supporting the prosthetic valve leaflets. The valve may include one or more anchors coupled to the frame and including ensnaring features configured to couple to one or more of chordae, trabeculae, or papillary structures to anchor the prosthetic valve within the native valve.

Embodiments as disclosed herein may include a method comprising deploying a prosthetic valve to a native valve of a patient's body. The valve may include a plurality of prosthetic valve leaflets. The valve may include a frame supporting the prosthetic valve leaflets. The valve may include one or more anchors coupled to the frame and including ensnaring features configured to couple to one or more of chordae, trabeculae, or papillary structures to anchor the prosthetic valve within the native valve. The method may include coupling the ensnaring features to one or more of the chordae or trabeculae.

Embodiments as disclosed herein may include a prosthetic valve configured to be deployed to a native valve. The valve may include a plurality of prosthetic valve leaflets. The valve may include a frame supporting the prosthetic valve leaflets. The valve may include one or more anchors coupled to the frame and configured to engage calcification of the native valve to anchor the prosthetic valve to the native valve.

Embodiments as disclosed herein may include a method comprising deploying a prosthetic valve to a native valve of a patient's body. The valve may include a plurality of prosthetic valve leaflets. The valve may include a frame supporting the prosthetic valve leaflets. The valve may include one or more anchors coupled to the frame and configured to engage calcification of the native valve to anchor the prosthetic valve to the native valve. The method may include engaging the calcification with the one or more anchors.

Embodiments as disclosed herein may include a prosthetic valve configured to be deployed to a native valve. The valve may include a plurality of prosthetic valve leaflets. The valve may include a frame supporting the prosthetic valve leaflets. The valve may include one or more anchors coupled to the frame and each having a tip and configured to extend radially outward from the frame, each of the one or more anchors having a portion with a thickness tapering downward in a direction towards the tip of the anchor.

Embodiments as disclosed herein may include a method comprising deploying a prosthetic valve to a native valve of a patient's body. The valve may include a plurality of prosthetic valve leaflets. The valve may include a frame supporting the prosthetic valve leaflets. The valve may include one or more anchors coupled to the frame and each having a tip and configured to extend radially outward from the frame, each of the one or more anchors having a portion with a thickness tapering downward in a direction towards the tip of the anchor.

Embodiments as disclosed herein may include a prosthetic valve configured to be deployed to a native valve. The valve may include a plurality of prosthetic valve leaflets. The valve may include an inner frame supporting the prosthetic valve leaflets and including a proximal portion and a distal portion. The valve may include a sealing body positioned radially outward of the inner frame and including an outer frame having a proximal portion coupled to the proximal portion of the inner frame and a distal portion including a plurality of strut cells forming a ring about the inner frame, the outer frame including a plurality of elongate strut arms extending from the proximal portion of the outer frame to the plurality of strut cells and at least one of the elongate strut arms including a deflection feature configured to allow the plurality of strut cells to deflect relative to the proximal portion of the outer frame.

Embodiments as disclosed herein may include a method comprising deploying a prosthetic valve to a native valve of a patient's body. The valve may include a plurality of prosthetic valve leaflets. The valve may include an inner frame supporting the prosthetic valve leaflets and including a proximal portion and a distal portion. The valve may include a sealing body positioned radially outward of the inner frame and including an outer frame having a proximal portion coupled to the proximal portion of the inner frame and a distal portion including a plurality of strut cells forming a ring about the inner frame, the outer frame including a plurality of elongate strut arms extending from the proximal portion of the outer frame to the plurality of strut cells and at least one of the elongate strut arms including a deflection feature configured to allow the plurality of strut cells to deflect relative to the proximal portion of the outer frame.

Embodiments as disclosed herein may include a prosthetic valve configured to be deployed to a native valve. The valve may include a plurality of prosthetic valve leaflets. The valve may include an inner frame supporting the prosthetic valve leaflets and including a proximal portion and a distal portion. The valve may include an outer frame positioned radially outward of the inner frame and including a plurality of struts, at least one of the plurality of struts having an undulation or an opening configured to increase a flexibility of the outer frame.

Embodiments as disclosed herein may include a method comprising deploying a prosthetic valve to a native valve of a patient's body. The valve may include a plurality of prosthetic valve leaflets. The valve may include an inner frame supporting the prosthetic valve leaflets and including a proximal portion and a distal portion. The valve may include an outer frame positioned radially outward of the inner frame and including a plurality of struts, at least one of the plurality of struts having an undulation or an opening configured to increase a flexibility of the outer frame.

Embodiments as disclosed herein may include a prosthetic valve configured to be deployed to a native valve. The valve may include a plurality of prosthetic valve leaflets. The valve may include a frame coupled to the prosthetic valve leaflets, the frame including a proximal end and a distal end and a plurality of struts joined at junctures, at least one of the plurality of struts extending in a direction from the proximal end towards the distal end and including a first segment extending along a first axis, a second segment, and a third segment extending along a second axis, and a first kink joining the first segment to the second segment at an angle, and a second kink joining the second segment to the third segment at an angle, with the second axis being offset from the first axis.

Embodiments as disclosed herein may include a method comprising deploying a prosthetic valve to a native valve of a patient's body. The valve may include a plurality of prosthetic valve leaflets. The valve may include a frame coupled to the prosthetic valve leaflets, the frame including a proximal end and a distal end and a plurality of struts joined at junctures, at least one of the plurality of struts extending in a direction from the proximal end towards the distal end and including a first segment extending along a first axis, a second segment, and a third segment extending along a second axis, and a first kink joining the first segment to the second segment at an angle, and a second kink joining the second segment to the third segment at an angle, with the second axis being offset from the first axis.

Embodiments as disclosed herein may include a prosthetic valve configured to be deployed to a native valve. The valve may include a plurality of prosthetic valve leaflets. The valve may include an inner frame supporting the prosthetic valve leaflets. The valve may include a sealing body positioned radially outward of the inner frame and including an outer frame having a proximal portion extending radially outward from the inner frame and a distal portion curving axially from the proximal portion and extending axially to a distal end of the outer frame. The valve may include a plurality of anchors extending radially outward from the distal portion of the outer frame and configured to impede distal movement of the outer frame.

Embodiments as disclosed herein may include a method comprising deploying a prosthetic valve to a native valve of a patient's body. The valve may include a plurality of prosthetic valve leaflets. The valve may include an inner frame supporting the prosthetic valve leaflets. The valve may include a sealing body positioned radially outward of the inner frame and including an outer frame having a proximal portion extending radially outward from the inner frame and a distal portion curving axially from the proximal portion and extending axially to a distal end of the outer frame. The valve may include a plurality of anchors extending radially outward from the distal portion of the outer frame and configured to impede distal movement of the outer frame.

BRIEF DESCRIPTION OF THE DRAWINGS

Features and advantages of the systems, apparatuses, and methods as disclosed herein will become appreciated as the same become better understood with reference to the specification, claims, and appended drawings wherein:

FIG. 55A illustrates a side view of a portion of a prosthetic valve according to an embodiment of the present disclosure.

FIG. 55B illustrates a top view of an anchor shown in FIG. 55A.

FIG. 55C illustrates a side view of the anchor shown in FIG. 55A.

DETAILED DESCRIPTION

Figure 1:
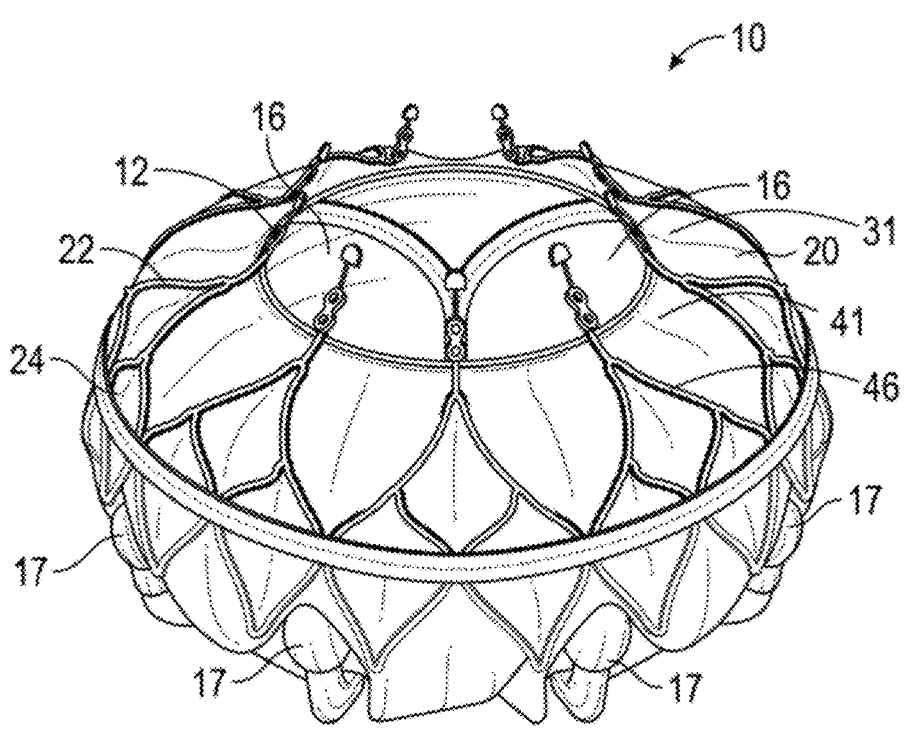
FIG. 1 illustrates a side perspective view of a prosthetic valve according to an embodiment of the present disclosure.

FIG. 1 illustrates a perspective view of a prosthetic valve 10 in the form of a replacement heart valve. The prosthetic valve 10 may be configured to be deployed within a portion of a patient's body. The prosthetic valve 10, for example, may be deployed within a native heart valve annulus, which may comprise a native mitral valve or a native tricuspid valve. In embodiments other implantation locations may be utilized such as within an aortic or pulmonary valve, or in other valve or locations within a patient's body as desired.

The prosthetic valve 10 may include a proximal end 12 and a distal end 14 (marked in FIG. 2), and a length therebetween. The prosthetic valve 10 may further include a plurality of prosthetic valve leaflets 16 configured to surround a flow channel for controlling flow through the valve 10. The prosthetic valve leaflets 16 may be configured to move between opened and closed states to mimic and replace the operation of native valve leaflets.

Figure 2:
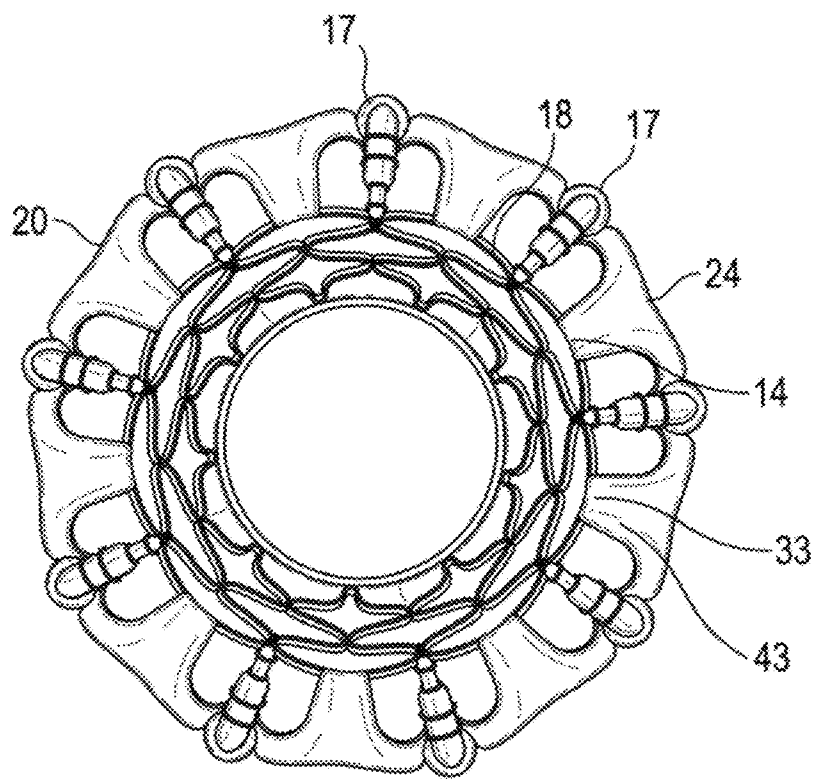
FIG. 2 illustrates a bottom view of the prosthetic valve shown in FIG. 1 with the leaflets excluded from view.
Figure 3:
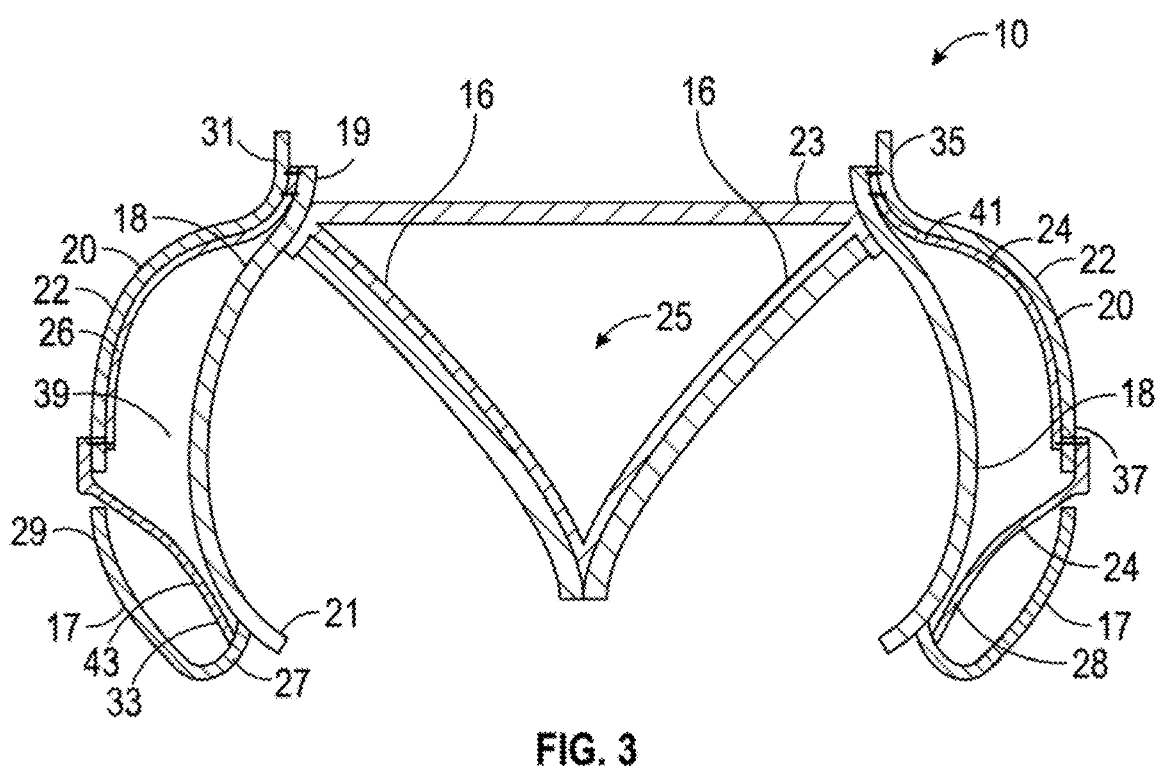
FIG. 3 illustrates a cross sectional schematic view of the prosthetic valve shown in FIG. 1.

In embodiments, the prosthetic valve leaflets 16 may be coupled to a valve frame 18 as shown in a cross sectional view in FIG. 3 and as shown in the bottom view of FIG. 2. As marked in FIG. 3, the valve frame 18 may include a proximal portion including a proximal end 19 and a distal portion including a distal end 21. The valve frame 18 may have a curved configuration, comprising a curved body that curves radially outward between the proximal end 19 and the distal end 21, or may have another configuration in embodiments as desired.

The proximal portion of the valve frame 18 may be coupled to a proximal portion of the prosthetic valve leaflets 16. The prosthetic valve leaflets 16 may be coupled to the valve frame 18 and may extend radially inward from the valve frame 18. The prosthetic valve leaflets 16 may couple to the valve frame 18 via an intermediate body 23 that may support the prosthetic valve leaflets 16 and may couple the leaflets 16 to the valve frame 18 via sutures or another method as desired.

The prosthetic valve leaflets 16 may surround a flow channel 25 as marked in FIG. 3, and may move between open and closed states to control flow through the flow channel 25. As shown in FIG. 3, the proximal end of the prosthetic valve 10 may comprise an inflow end of the valve 10, and the distal end of the prosthetic valve 10 may comprise an outflow end, although other configurations may be utilized as desired.

FIG. 2 illustrates a bottom view of the valve 10. The leaflets are excluded from view in FIG. 2. As shown in the bottom view of FIG. 2, the valve frame 18 may include a plurality of struts spaced from each other with spaces. Such a configuration may allow the valve frame 18 to move between an undeployed, unexpanded, or linearized configuration to a deployed or expanded configuration. For example, the valve frame 18 may expand radially outward to move to the deployed or expanded configuration, with the length of the valve frame 18 decreasing due to the increased diameter of the valve frame 18. Other configurations of valve frames 18 may be utilized as desired.

Referring to FIG. 1, the valve 10 may include one or more anchors 17 that may be coupled to the plurality of prosthetic valve leaflets 16 and each may be configured to anchor to a portion of a patient's heart. The anchors 17 may particularly be configured to anchor to the native valve leaflets of the patient's heart. The anchors 17 may extend around the leaflets to anchor to the native valve leaflets. The anchors 17 may comprise distal anchors positioned at the distal end 14 of the valve 10, or in embodiments may be positioned in another position as desired.

The anchors 17 may each extend radially outward from the flow channel 25 and radially outward from the prosthetic valve leaflets 16 of the valve 10. FIG. 3, for example, illustrates that the anchors 17 may be coupled to the valve frame 18 comprising an interior frame of the valve 10. The anchors 17 may be coupled to the distal portion of the valve frame 18. The anchors 17 may each include a proximal portion 27 and a distal portion 29, with the proximal portion 27 coupled to the valve frame 18 and the distal portion 29 comprising a tip of the respective anchor 17.

FIG. 3 illustrates a cross sectional schematic view of the valve 10. As shown in FIG. 3, each anchor 17 is configured to extend distally and then curve in a proximal direction to the tip of the respective one of the anchors 17. Such a configuration may allow the anchor 17 to extend around a native leaflet and hook around the distal portion of the leaflet. The anchor 17 may thus resist a force applied in the proximal direction to the valve 10 and may anchor the valve 10 within the native valve annulus. Other configurations of anchors 17 may be utilized in embodiments as desired.

The anchors 17 are shown in FIGS. 1-3 in a deployed or expanded configuration, in which the tips of the anchors 17 extend proximally. In embodiments, the anchors may be configured to be in undeployed, unexpanded, or linearized configuration in which the tips of the anchors 17 extend distally. Upon deployment, the anchors 17 may be configured to move from the undeployed configuration radially outward to the deployed configuration, with the tips flipped towards the proximal direction. Such an operation may allow the anchors 17 to flip over the native valve leaflets to anchor to the native valve leaflets during deployment. Other deployment methods for the anchors 17 may be utilized in embodiments as desired.

Referring to FIG. 1, the valve 10 may include a sealing body 20. The sealing body 20 may be positioned radially outward from the leaflets 16 and may comprise the outer surface of the valve 10. The sealing body 20 may define the outer diameter of the valve 10 and may comprise the outer periphery of the valve 10. The sealing body 20 may include a proximal portion having a proximal end 31, and may include a distal portion having a distal end 33 (marked in FIG. 2).

The sealing body 20 may include a frame 22 and a skirt 24 as shown in FIG. 1, or in embodiments may comprise only a frame or only a skirt as desired. The frame 22 may comprise an outer frame that is positioned radially outward from the valve frame 18. The skirt 24 may be coupled to the frame 22.

Referring to FIG. 3, the frame 22 may have a proximal portion 35 that couples to the proximal end 19 of the valve frame 18. The proximal portion 35 may extend radially outward from the proximal end 19 of the valve frame 18 and from the prosthetic valve leaflets 16. A distal portion 37 of the frame 22 may be spaced from the prosthetic valve leaflets 16 and the valve frame 18 with a gap 39. The gap may be positioned between the frame 22 of the sealing body 20 and a distal portion of the valve frame 18. The valve frame 18 accordingly may comprise an inner frame and the frame of the sealing body 20 may comprise an outer frame surrounding the inner frame. The sealing body 20 may surround the inner valve frame 18 and the prosthetic valve leaflets 16.

As shown in FIG. 3, the frame 22 of the sealing body 20 may have a length that extends distally to a lesser distance than the distal end of the valve frame 18. As such, the frame 22 of the sealing body 20 may be shorter than the valve frame 18. The frame 22 of the sealing body 20 may further have a curved configuration that curves outward from the valve frame 18, with a greatest diameter of the frame 22 being at the distal portion of the frame 22.

Referring to FIG. 1, the frame 22 of the sealing body 20 may include a plurality of struts 46 forming the frame 22, with the struts separated by spaces. Such a configuration may allow the frame 22 to move between an undeployed, unexpanded, or linearized configuration to a deployed or expanded configuration as shown in FIG. 1, in which the frame 22 and sealing body 20 have a curved bulbous shape. As with the valve frame 18, the length of the frame 22 of the sealing body 20 may decrease as the diameter of the frame 22 of the sealing body 20 increases during deployment. The diameter of the frame 22 of the sealing body 20 may radially expand outward from the inner valve frame 18 simultaneously, or at a different time or rate of expansion as the inner valve frame 18 in embodiments.

Figure 12:
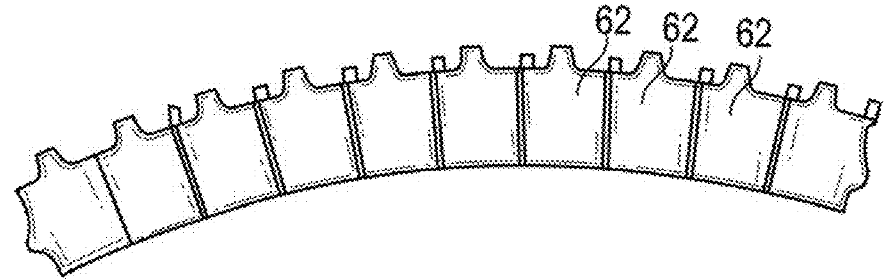
FIG. 12 illustrates a plurality of segments of the sealing body shown in FIG. 1 coupled together.

The sealing body 20 may include a skirt 24 that may extend around the inner valve frame 18 and the prosthetic valve leaflets 16. The skirt 24 may be coupled to the frame 22 of the sealing body or may be free from the frame 22 in embodiments. The skirt 24 may have a proximal portion 41 that is coupled to the proximal portion of the frame 22 of the sealing body 20, and may be coupled to the proximal portion of the valve frame 18. The skirt 24 may have a distal portion 43 (marked in FIG. 2) that may be coupled to the distal end of the inner valve frame 18, and may be coupled to one or more of the anchors 17. The distal portion 43 may include a portion for coupling to the inner valve frame 18 and may include a portion for coupling to one or more of the anchors 17 that may alternate in position circumferentially about the valve frame 18. The portions may comprise tabs as shown in FIG. 12, or may have another configuration as desired.

Referring to FIG. 3, the skirt 24 may extend along the frame 22 of the sealing body 20. The skirt 24 may include multiple portions that may be coupled together. For example, a first proximal portion 26 of the skirt 24 may be positioned radially inward of the frame 22 of the sealing body 20, and may be coupled to a second distal portion 28 of the skirt 24 that is positioned at least partially radially outward of the distal end of the frame 22, and then extends radially inward of the frame 22 to the distal portion 43 of the skirt 24. The second distal portion 28 may comprise the portion that couples to the anchors 17 and to the inner valve frame 18. The first proximal portion 26 and the second distal portion 28 of the skirt 24 may be coupled together via sutures or another form of coupling as desired to form a continuous surface in embodiments.

The second distal portion 28 of the skirt may extend further distal than the tips of the anchors 17, and may couple to the anchors 17 and the valve frame 18 at a position that is distal of the tips of the anchors 17. As shown in FIG. 3, the anchors 17 may be configured to extend radially outward from the inner valve frame 18 and across the gap 39 to the tip of the respective anchor 17.

The skirt 24, and particularly the second distal portion 28 of the skirt 24, may be configured to be flexible to allow the skirt 24 to move as desired, and particularly to move to conform to the position of the anchors 17. The skirt 24 may be made of a material that resists fluid flow therethrough, such as a cloth material, woven material, or other material such as a polymer or other material that resists fluid flow therethrough. A variety of materials may be utilized for the skirt 24 as desired.

The sealing body 20 may be configured to abut a portion of the patient's heart to reduce fluid flow. For example, the sealing body 20 may abut a surface of a patient's native valve leaflet to reduce fluid flow between the sealing body 20 and the native leaflet. The sealing body 20 may be configured to abut other portions of the patient's heart to reduce fluid flow as desired.

The second distal portion 28 of the skirt 24 may extend radially inward to allow the anchors 17 to pass through the sealing body 20 at least partially in a radially inward direction. The sealing body 20 may be configured for the anchors 17 to at least partially pass through in a radially inward direction, as shown in FIG. 3 for example. The anchors 17 may each at least partially pass through the sealing body 20 such that the outer diameter of the sealing body 20 is at or greater than the diameter of the anchors 17. As such, the outer periphery of the sealing body 20 may be positioned at or greater than the outer periphery of the anchors 17. In embodiments, a portion of an anchor 17 may protrude from the sealing body 20, such as a tip of the anchor 17, yet at least partially pass through the sealing body 20.

In embodiments, the sealing body 20 may be biased to extend radially outward. For example, the sealing body 20 may be shape set to extend radially outward further than the outer diameter of the anchors 17 in embodiments. Such a configuration may allow the sealing body 20 to extend radially outward at or further than the outer diameter of the anchors 17. The sealing body 20 may be configured to be deflected to move radially inward to allow one or more of the anchors 17 to properly capture a native leaflet in embodiments. In embodiments, a flexibility of the sealing body 20 may be tuned to allow the sealing body 20 to be moved during capture of a leaflet. In embodiments, the movement of the sealing body 20, including the frame 22 of the sealing body 20, may be imaged during a deployment procedure. The imaging may be fluoroscopy or other forms of imaging such as echocardiography. The movement of the sealing body may be imaged to determine if one or more of the anchors 17 have properly captured a native leaflet. For example, an inward deflection of the frame 22 may be imaged to determine if one or more of the anchors 17 have properly captured a native leaflet. In embodiments, fluoroscopy may be utilized to image a deflection of the frame 22 upon capture of one or more native valve leaflets.

The sealing body 20 may be configured to move relative to the anchors 17 to allow the one or more anchors 17 to at least partially pass through the sealing body 20 in a radially inward direction if there is a miscapture of a native leaflet. The relative movement of the sealing body 20 may be radially outward relative to the anchors 17. A relative movement of the anchors 17 may thus be radially inward relative to the sealing body 20.

In embodiments, one or more of the anchors 17 may be biased to deflect radially inward relative to the sealing body 20. As such, if there is a miscapture of a native leaflet, the anchor that missed capture of the native leaflet may deflect radially inward to at least partially pass through the sealing body 20. In embodiments, a combination of a sealing body 20 biased to extend radially outward, and one or more anchors 17 configured to deflect radially inward relative to the sealing body 20 may be utilized to allow the anchors 17 to pass at least partially through the sealing body 20.

Figure 4:
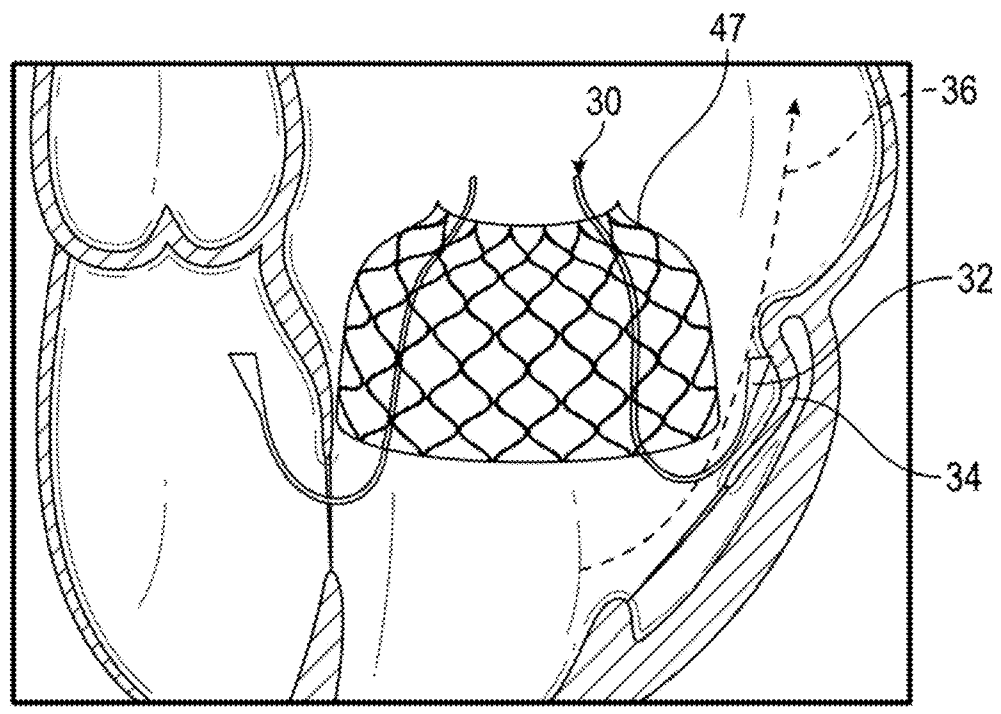
FIG. 4 illustrates a schematic view of a prosthetic valve implanted within a native heart valve.

The sealing body 20 may provide a function to reduce fluid flow outside of the sealing body 20 at the position of an anchor 17 that misses capture of a leaflet. Such a feature of the sealing body is reflected by example in FIG. 4, in which a sealing body is not configured for an anchor to pass at least partially through. FIG. 4 illustrates a prosthetic valve 30 that has been deployed with an anchor 32 missing capture of the leaflet 34. The anchor 32 in such a situation may remain positioned between the native valve leaflet and the remainder of the valve 30. The anchor 32 remains intra-annular and thus props open the space between the valve 30 and the leaflet 34. As such, no fluid seal is formed at the position of the anchor 32 by the sealing skirt 47. Paravalvular leakage (as marked by flow line 36) between the anchor 32 and the leaflet 34 may result, which may reduce the functionality of the valve 30.

Figure 5:
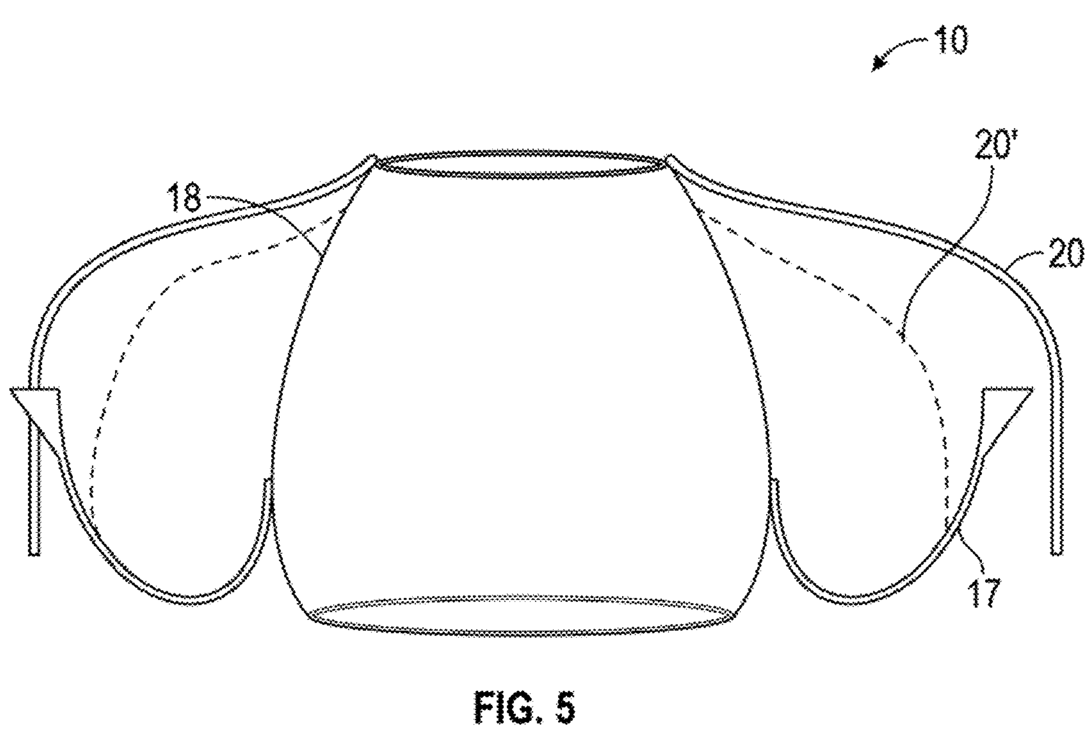
FIG. 5 illustrates a schematic view of a prosthetic valve according to an embodiment of the present disclosure.

A valve 10 according to embodiments herein, however, may be configured to address a missed capture of a leaflet. FIG. 5, for example, illustrates that the sealing body 20 of the valve 10 may be configured to move relative to the anchor 17 such that the sealing body 20 may be positioned with an outer diameter radially inward of the anchor 17 in a circumstance of capture of the native leaflet. Such a configuration is marked in dashed lines in FIG. 5 by reference number 20'. The sealing body 20' may be configured to overcome a bias to move radially inward during capture of a leaflet and/or the anchor 17 may be held radially outward from the sealing body 20'. In such a configuration of a captured leaflet, the native leaflet may be positioned between the anchor 17 and the sealing body 20', with the sealing body 20' abutting the native leaflet to reduce fluid flow at that position. The sealing body 20' may be flexible such that damage to the native leaflet does not occur.

The sealing body 20, as marked in solid lines in FIG. 5, however, may be configured to allow an anchor 17 that fails to capture the leaflet to pass through at least a portion of the sealing body 20. The sealing body 20 may have an outer diameter as shown in FIG. 5 that is greater than the outer radial extent of the anchor 17 or may be the same as the outer radial extent of the anchor 17. As such, the sealing body 20 may be positioned to continue to abut the native leaflet to reduce fluid flow, unlike the situation shown in FIG. 4 with the anchor 32.

Figure 6:
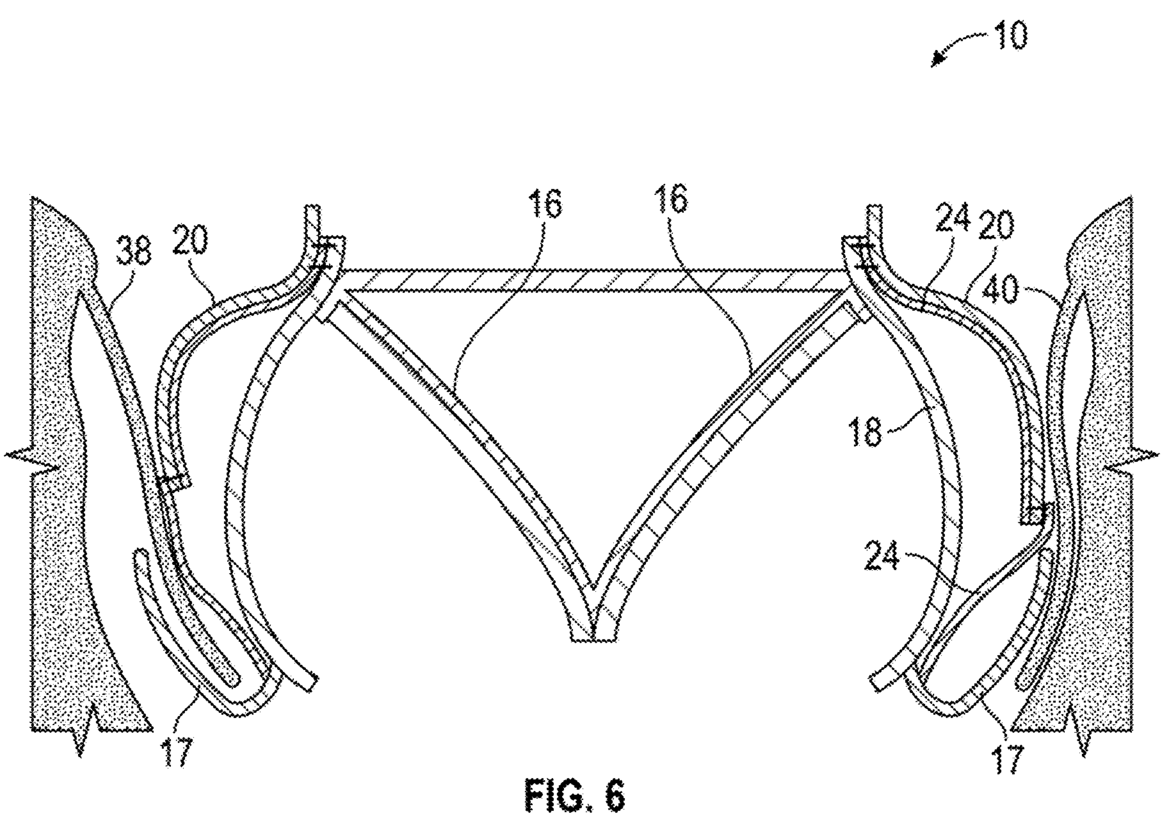
FIG. 6 illustrates a cross sectional schematic view of the prosthetic valve shown in FIG. 1 implanted within a native heart valve.

FIG. 6, for example, illustrates a configuration of a captured native leaflet 38 shown on the left side of FIG. 6, with the native leaflet 38 positioned between the anchor 17 and the sealing body 20 at that leaflet 38. The sealing body 20 abuts the native leaflet 38 to reduce fluid flow between the sealing body 20 and the native leaflet 38.

The right side of FIG. 6, however, illustrates a miscaptured native leaflet 40, in which the anchor 17 at that leaflet 40 failed to extend around the leaflet 40 at deployment. The anchor 17 at that leaflet 40, however, at least partially passes through the sealing body 20 to allow the sealing body 20 to abut and seal against the miscaptured native leaflet 40 at that position. As such, reduced paravalvular leakage (PVL) and improved operation of the valve 10 may result.

The sealing body 20, and particularly the skirt 24 of the sealing body 20 may be configured to surround an anchor 17 that has failed to capture a native leaflet. These portions of the sealing body 20 may press against the native leaflet to reduce fluid flow at the position of the anchor 17 that missed capture of the native leaflet.

Figure 7:
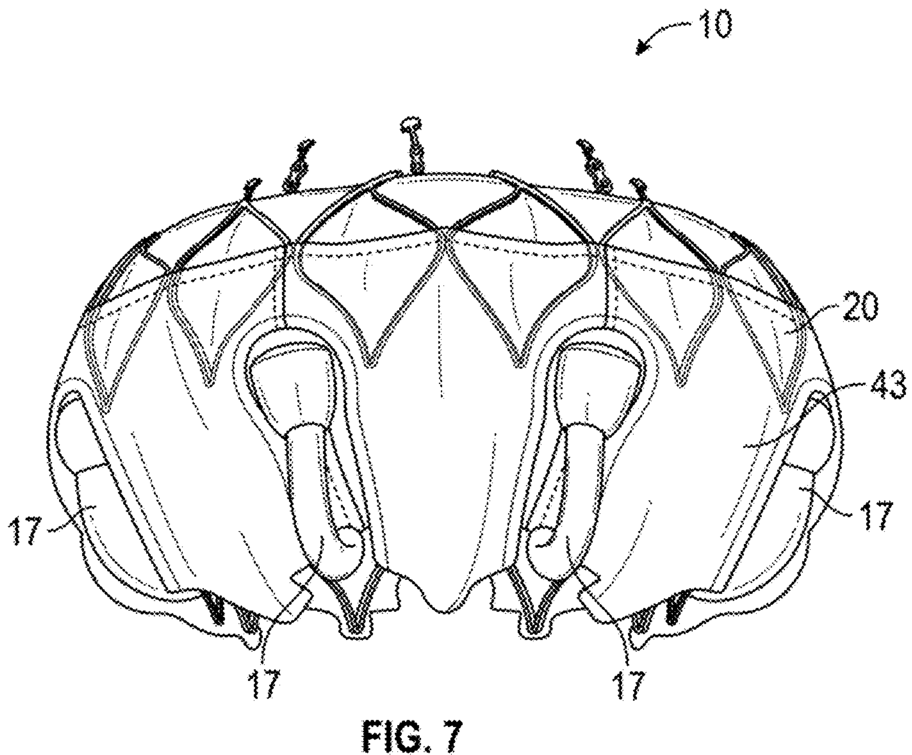
FIG. 7 illustrates a bottom side perspective view of the prosthetic valve shown in FIG. 1.

FIG. 7, for example, illustrates a side perspective view of the valve 10, illustrating the anchors 17 at least partially passing through the sealing body 20. Portions of the sealing body 20 are positioned at or radially outward from the anchor 17, for contact with a local surface of the patient's body. The tips of the anchors 17 may at least partially pass through the sealing body 20 in a radially inward direction, with a part of the tips being positioned radially outward of the sealing body 20.

Figure 8:
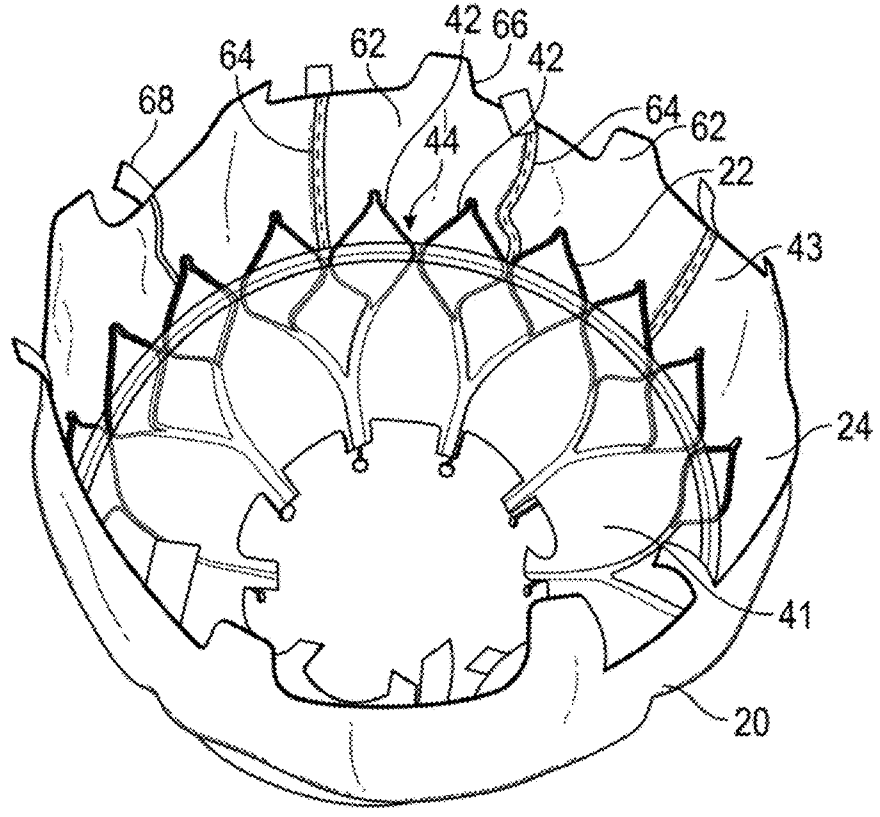
FIG. 8 illustrates a bottom perspective view of the sealing body shown in FIG. 1, with the valve body removed from view.
Figure 9:
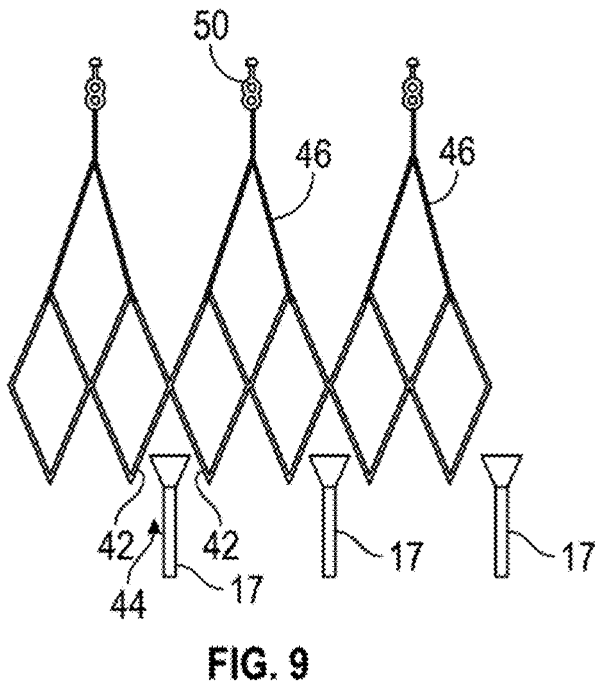
FIG. 9 illustrates a plan view of the frame of the sealing body shown in FIG. 1 and a relative position of anchor tips.

FIG. 8 illustrates a bottom perspective view of the sealing body 20 separate from the remainder of the valve 10. The frame 22 is shown to include a plurality of struts separated by spaces. Certain struts may be configured for the anchors 17 to at least partially pass through the spaces between the struts. For example, distal struts 42 at a distal end of the frame 22 may have a space 44 between the struts 42 that allows the anchors 17 to pass through. FIG. 9, for example, illustrates the distal struts 42 having spaces 44 therebetween, to allow the anchors 17 to pass through. The portions of the distal struts 42 on either side of the anchors 17 may provide additional support for the sealing body 20 around the anchors 17 when the anchors at least partially pass through the sealing body 20.

Figure 10:
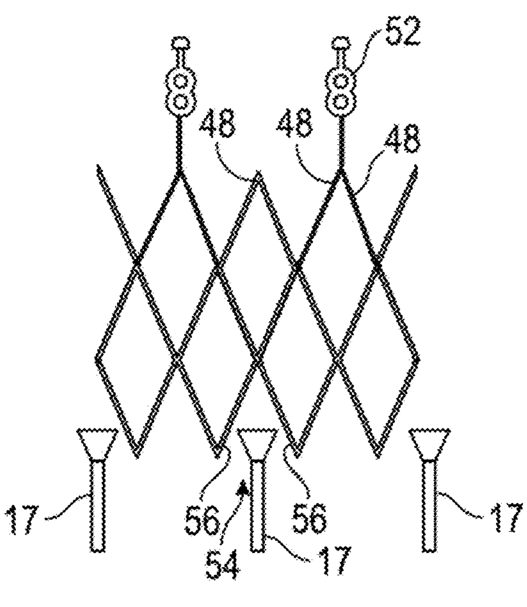
FIG. 10 illustrates a plan view of a frame of a sealing body and a relative position of anchor tips, according to an embodiment of the present disclosure.

The struts as shown in FIG. 9 may include proximal struts 46 that each couple to a securing device 50 for securing to a delivery apparatus for the valve 10, and for securing to the skirt 24 of the sealing body 20. An alternative configuration is shown in FIG. 10, in which proximal struts 48 may couple to a securing device 52 or may terminate at the proximal portion of the frame. The configuration shown in FIG. 10 may include spaces 54 between distal struts 56 of the frame for the anchors 17 to pass through.

Referring back to FIG. 8, the skirt 24 may be coupled to the frame 22 via sutures or other form of coupling. The skirt 24 may include the proximal portion 41 and the distal portion 43. The proximal portion 41 may be positioned radially interior of the frame 22, and the distal portion 43 may be at least partially positioned radially outward of the frame 22. The skirt 24 may be made of a material that has low or no permeability to fluid, particularly blood, to allow the skirt 24 to seal against a portion of a patient's heart and reduce fluid flow.

The distal portion 43 may include a plurality of segments 62 that may be coupled together to form an annular shaped distal portion 43. The plurality of segments 62 may be coupled together at seams 64, with the seams 64 configured to receive a respective anchor 17. Each seam 64 may correspond to a receiving portion for receiving one of the anchors 17. Each segment 62 may include a coupling tab 66 for coupling the skirt 24 to the valve frame 18 and may include a coupling tab 68 for coupling the skirt 24 to an anchor 17.

Figure 11:
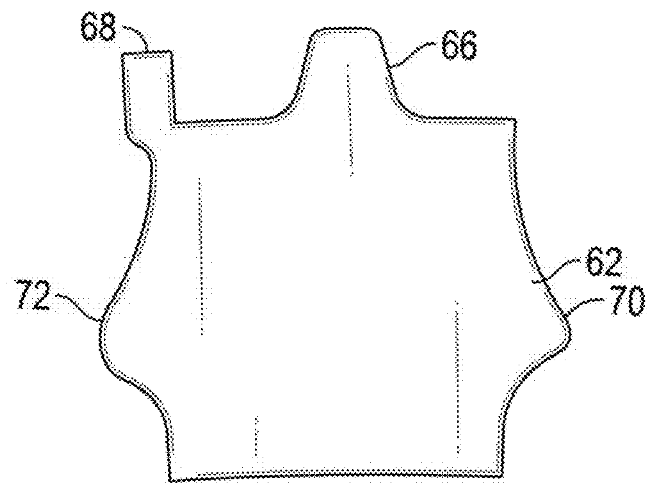
FIG. 11 illustrates a plan view of a segment of a sealing body shown in FIG. 1.

FIG. 11, for example, illustrates a segment 62 showing side seam portions 70, 72 for coupling to an adjacent segment. FIG. 12 illustrates the segments 62 coupled to each other to form the distal portion 43 of the skirt 24.

Referring back to FIG. 7, the distal portion 43 of the skirt 24 may be configured to receive the anchors 17 and at least partially envelope the anchors 17 to reduce fluid flow around an anchor 17 that miscaptures a native valve leaflet.

Other configurations of skirts may be utilized.

Figure 13:
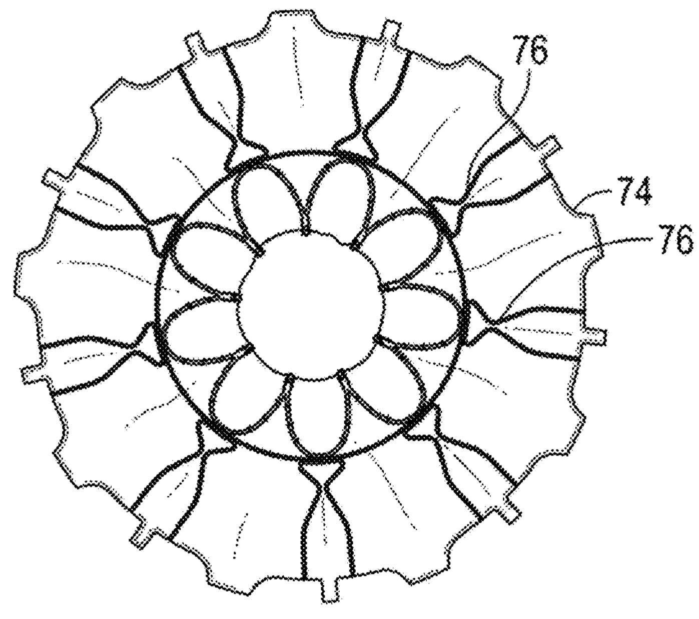
FIG. 13 illustrates a top view of a sealing body according to an embodiment of the present disclosure.
Figure 14:
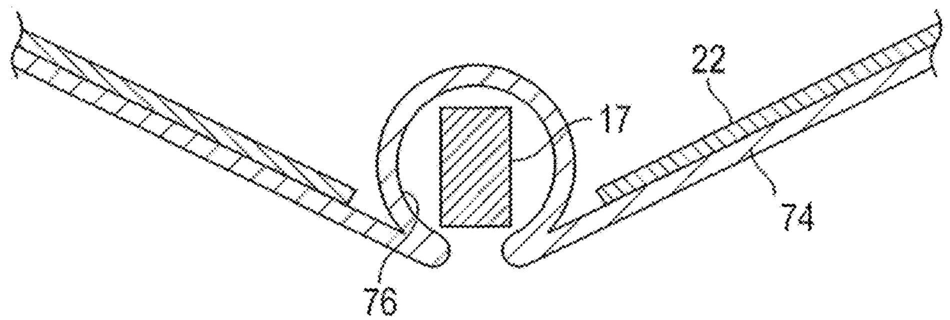
FIG. 14 illustrates a top cross sectional schematic view of an anchor within the sealing body shown in FIG. 13.

FIG. 13, for example, illustrates a top view of an embodiment of a skirt 74 including a receiving portion in the form of pockets 76 formed in the skirt 74 for receiving an anchor 17. FIG. 14, for example, illustrates the operation of such a skirt 74, with the anchor 17 within the formed pocket 76 of the skirt 74, and the material of the skirt 74 enveloping the anchor 17 such that the skirt 74 forms the outer surface of the valve 10 at the position of the anchor 17. The pockets 76 may be contoured to the shape of the anchor 17. The shape of the contour may be formed via stitching used to form the material comprising the pockets 76.

Figure 15:
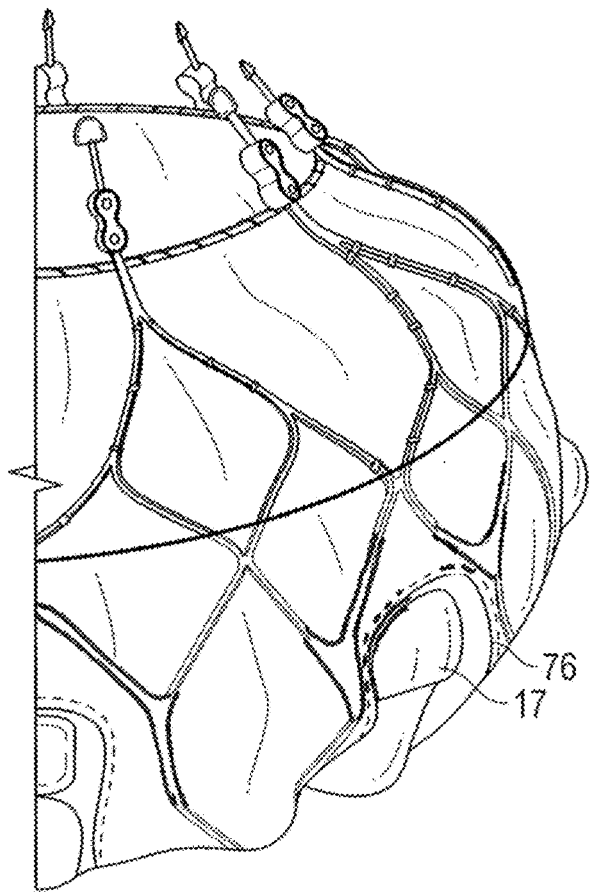
FIG. 15 illustrates a side perspective view of an anchor within the sealing body shown in FIG. 13.

FIG. 15 illustrates a side perspective view of the anchor 17 positioned within the formed pocket 76 of the skirt 74.

Figure 16:
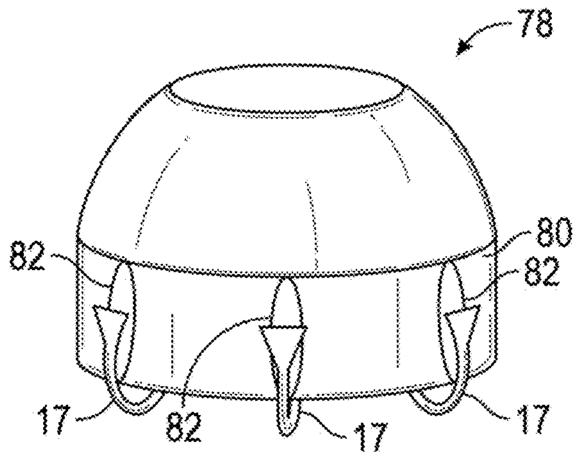
FIG. 16 illustrates a side schematic view of a prosthetic valve according to an embodiment of the present disclosure.
Figure 17:
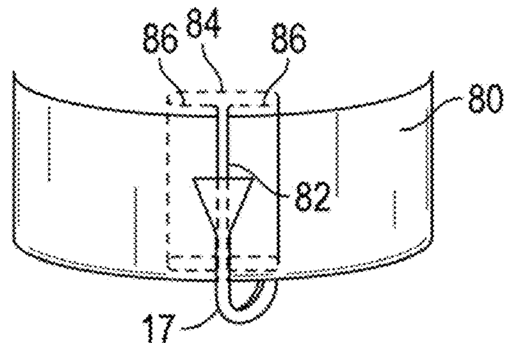
FIG. 17 illustrates a close up perspective view of a slit of a sealing body shown in FIG. 16.

FIG. 16 illustrates another embodiment of a valve 78, including a skirt 80 having receiving portions in the form of slits 82 that serve as openings for the anchors 17 to at least partially pass through. In embodiments, the anchors 17 may pass through the slits 82 with no skirt material forming a pocket for the anchor 17, or, in embodiments a pocket may be formed for the anchor 17. FIG. 17, for example, illustrates an embodiment including a pocket 84, which may comprise skirt material that is folded over itself to form one or more pleats 86. The anchor 17 may be configured to at least partially pass through the skirt 80 to be positioned within the pocket 84.

Figure 18:
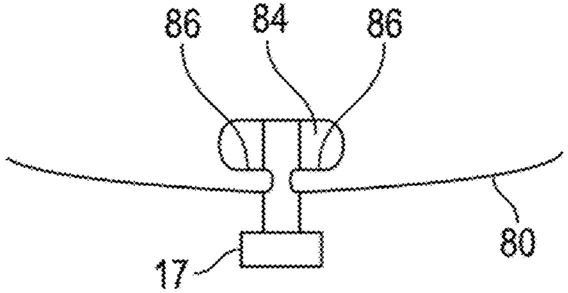
FIG. 18 illustrates a top cross sectional schematic view of an anchor positioned radially outward of a sealing body shown in FIG. 16.
Figure 19:
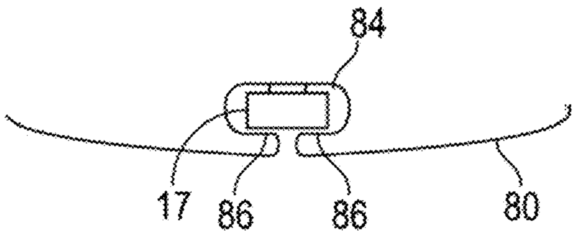
FIG. 19 illustrates a top cross sectional schematic view of the anchor shown in FIG. 18 positioned within the sealing body shown in FIG. 18.

FIG. 18 illustrates the anchor 17 positioned outside of the pocket 84, and FIG. 19 illustrates the anchor 17 positioned within the pocket 84.

Figure 20:
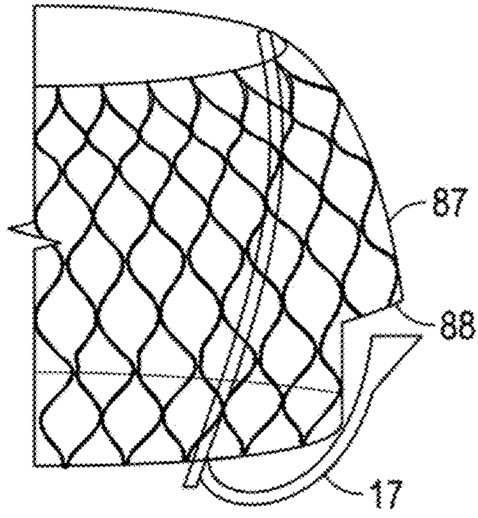
FIG. 20 illustrates a side perspective view of a prosthetic valve according to an embodiment of the present disclosure.
Figure 21:
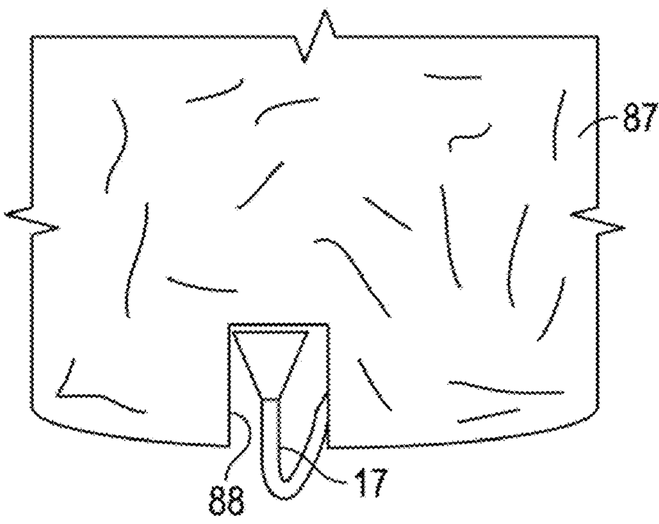
FIG. 21 illustrates a side view of a portion of the prosthetic valve shown in FIG. 20.

FIG. 20 illustrates an embodiment in which the skirt 87 may include a receiving portion in the form of an aperture 88 for an anchor 17 to at least partially pass through. The skirt 87 may lack material positioned radially inward of the anchor 17. The anchor 17 as such may be passed through the aperture 88 without being positioned within a pocket. FIG. 21 illustrates a front view of the embodiment shown in FIG. 20 with a cloth material of the skirt shown surrounding the anchor 17.

Figure 22:
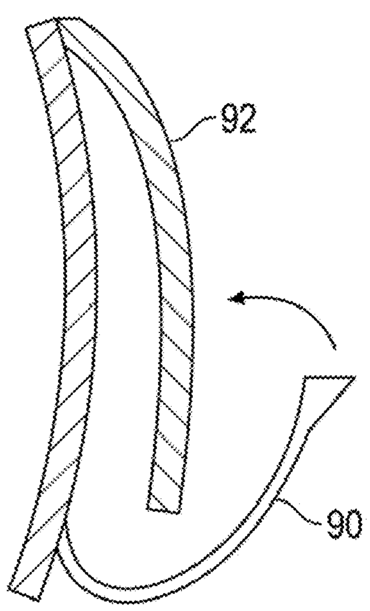
FIG. 22 illustrates a side cross sectional schematic view of a portion of a prosthetic valve according to an embodiment of the present disclosure.

In embodiments, the anchors may be configured to deflect radially inward to pass at least partially through the sealing body. FIG. 22, for example, illustrates an embodiment in which the anchor 90 is made of a flexible material and is biased to flex to deflect radially inward towards the sealing body 92. The anchors 90, for example, may be made of a shape memory material such as Nitinol that biases the anchor 90 to deflect radially inward toward the sealing body 92 and pass at least partially through the sealing body 92. The anchors 90, for example, may be coupled to an anchor frame that is formed separate from the valve frame, and may be made of a material that is more flexible than the valve frame to allow for flex inward towards the sealing body 92.

Figure 23:
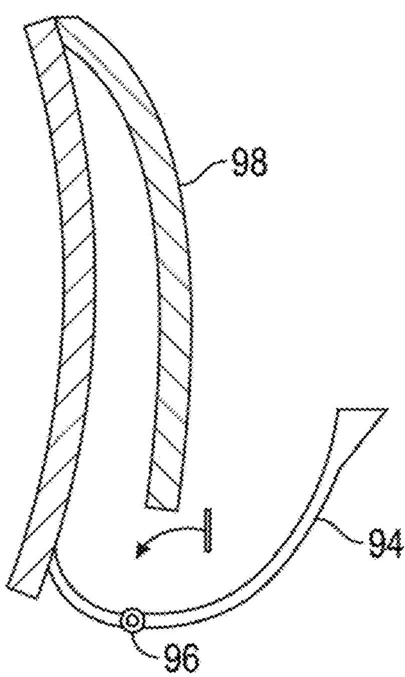
FIG. 23 illustrates a side cross sectional schematic view of a portion of a prosthetic valve according to an embodiment of the present disclosure.

FIG. 23 illustrates an embodiment in which an anchor 94 may include a hinge 96 for the anchor 94 to deflect about in the radially inward direction. The anchor 94 may deflect radially inward to pass at least partially through the sealing body 98. The anchor 94 may be biased to deflect radially inward via a shape memory material such as Nitinol, or via another method.

A combination of a sealing body 20 that is configured to extend radially outward, and one or more anchors configured to deflect radially inward, may be utilized in embodiments.

FIGS. 24-28 illustrate an exemplary method of deploying a valve that includes a sealing body as disclosed herein. In embodiments, the method may be modified as desired, including removing steps, adding steps, or utilizing steps, systems, or apparatuses from various other embodiments as desired.

Figure 24:
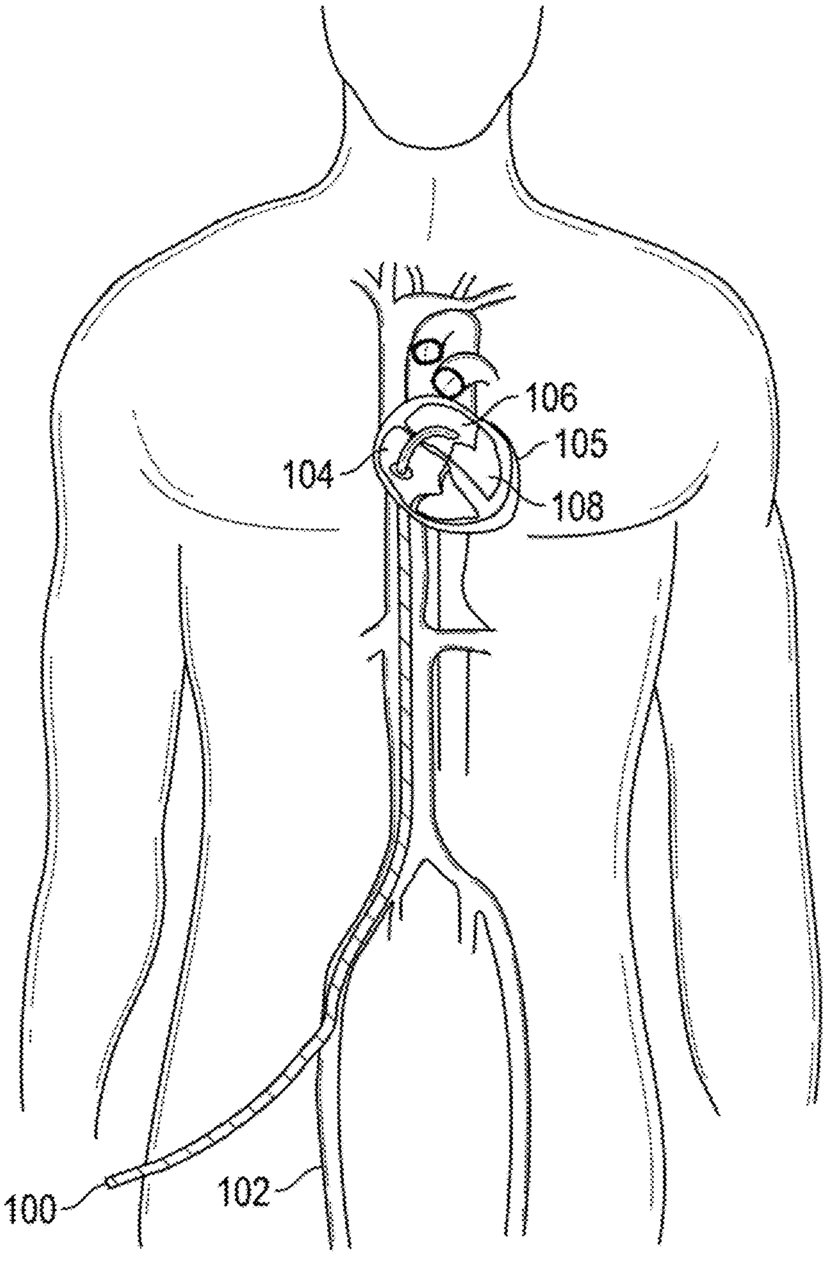
FIG. 24 illustrates a schematic view of a delivery apparatus extending within a patient's body.

The method may include deploying a prosthetic valve to a native valve of a patient's body. Referring to FIG. 24, a delivery apparatus 100 may be passed percutaneously into a patient's body in a minimally invasive manner. In other embodiments, more invasive means may be utilized as desired.

The delivery apparatus 100 may be utilized for transcatheter delivery of the valve. The delivery apparatus 100 and may pass transvenous through the femoral artery 102 or another portion of the patient's vasculature. For example, transjugular entry or other methods of entry may be utilized as desired. The delivery apparatus 100 may pass to the patient's heart 105.

The delivery apparatus 100 may be used to deliver the valve to the tricuspid valve, and as such, may be positioned within the right atrium 104 of the patient's heart for delivery to the tricuspid valve. In an embodiment in which delivery is to the mitral valve, the delivery apparatus 100 may pass transseptal to the left atrium 106 for delivery to the mitral valve. The delivery apparatus 100 may advance towards the left ventricle 108 of the patient's heart for mitral delivery.

Figure 25:
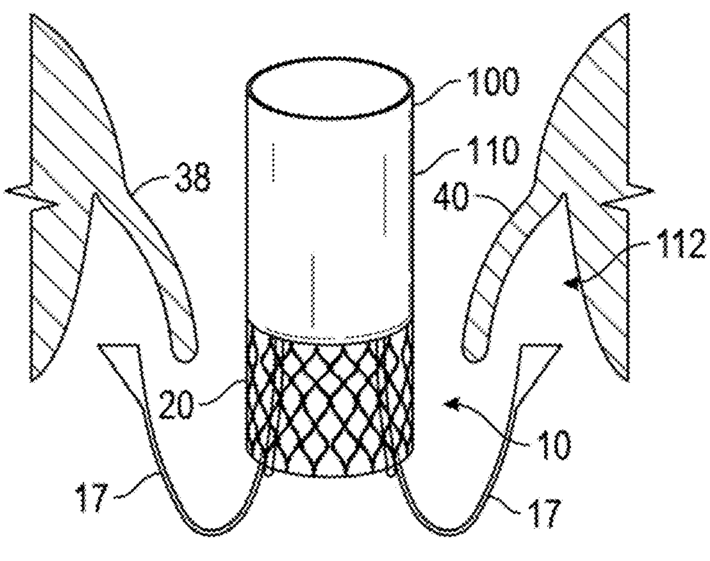
FIG. 25 illustrates a side schematic view of a prosthetic valve being deployed according to an embodiment of the present disclosure.

FIG. 25 illustrates that the valve, for example valve 10 shown in FIG. 1, may be passed out of a capsule 110 of the delivery apparatus 100 to be deployed to a native valve such as a native mitral valve 112. The anchors 17 of the prosthetic valve 10 may deploy and extend radially outward for capture of native valve leaflets 38, 40. The sealing body 20 may be partially or fully restrained from radially expanding outward by the constrictive force of the capsule 110.

Figure 26:
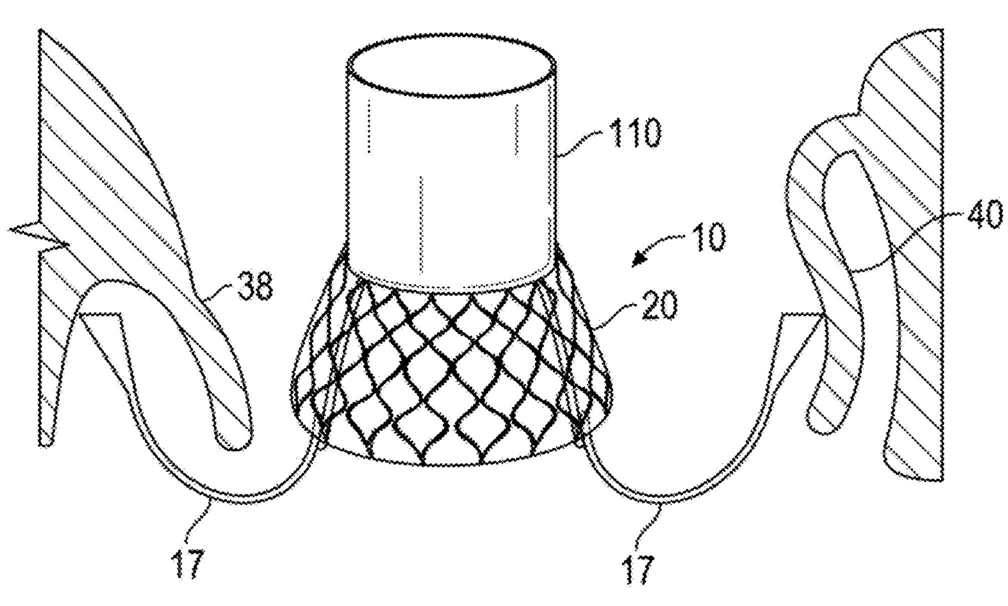
FIG. 26 illustrates a side schematic view of the prosthetic valve shown in FIG. 25 being deployed.

FIG. 26 illustrates the valve 10 continuing to be deployed, with an anchor 17 capturing a leaflet 38 and an anchor 17 missing capture of the leaflet 40. The anchor 17 that captures the leaflet 38 may extend around the leaflet 38. The anchor 17 missing capture of the leaflet 40 may be positioned between the sealing body 20 and the missed leaflet 40 in this configuration.

As shown in FIG. 26, the sealing body 20 may yet be partially or fully restrained from radially expanding outward by the constrictive force of the capsule 110. As such, the sealing body 20 has not yet expanded outward to allow the anchor 17 that missed capture of the leaflet 40 to pass through the sealing body 20, and has not yet expanded outward to abut against and seal against the leaflet 38 that has been captured by the anchor 17.

Figure 27:
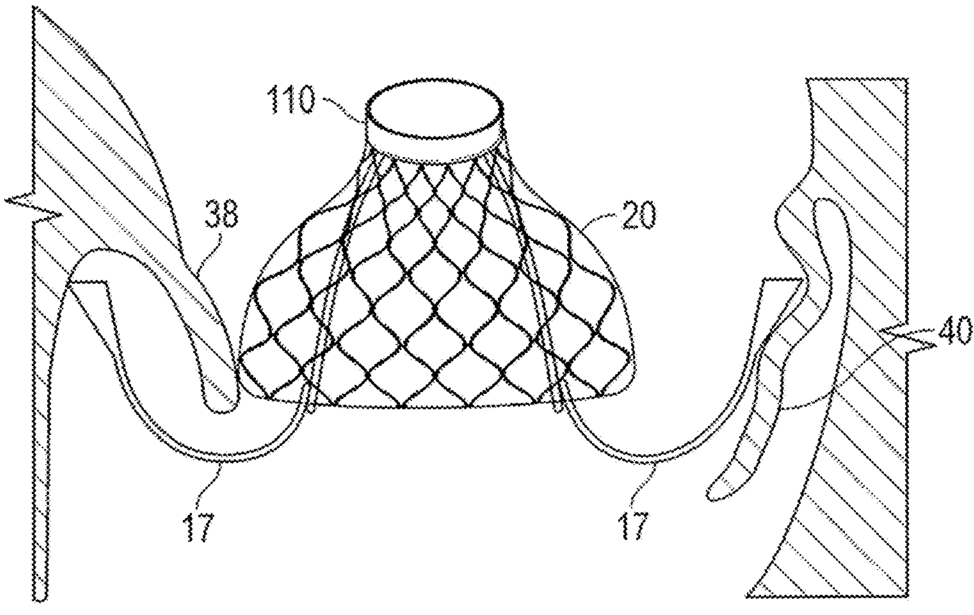
FIG. 27 illustrates a side schematic view of the prosthetic valve shown in FIG. 25 being deployed.
Figure 28:
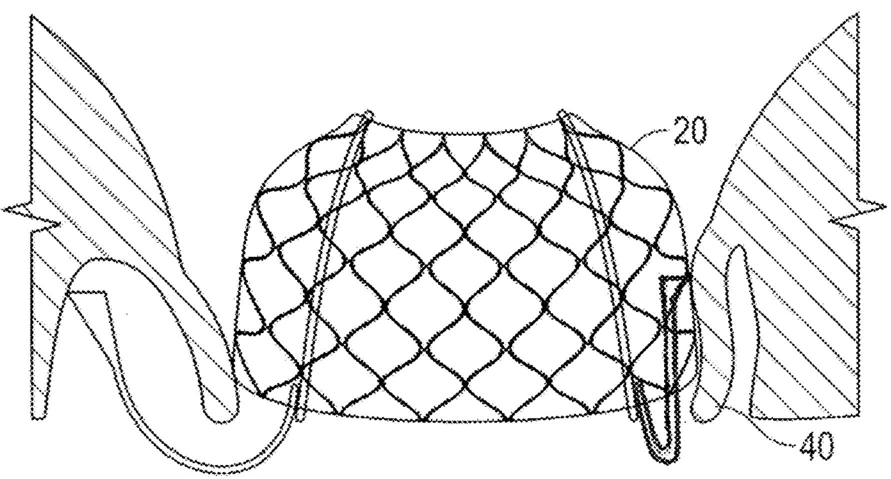
FIG. 28 illustrates a side schematic view of the prosthetic valve shown in FIG. 25 being deployed.

FIG. 27 illustrates the continued expansion of the sealing body 20. The expansion may allow the sealing body 20 to abut against and seal against the captured leaflet 38. FIG. 28 illustrates the continued expansion of the sealing body 20 as the valve 10 is released from the capsule 110. The anchor 17 at the miscaptured leaflet 40 at least partially passes through the sealing body 20 in a radially inward direction to allow the sealing body 20 to seal against the leaflet 40 around the anchor 17 and reduce fluid flow therethrough. The sealing body 20 at the anchor that missed capture of the leaflet 40 may envelop the anchor 17 and may abut the leaflet 40.

In embodiments, the anchor 17 that missed capture of the leaflet may be configured to deflect inward to pass at least partially through the sealing body 20.

One or more of the anchors 17 may miscapture a leaflet to allow the valve 10 to remain anchored within the native valve. The sealing body 20 may be configured to allow one or more of the anchors that miscaptures a leaflet to at least partially pass through.

Variations in the method of FIGS. 24-28 may be provided as desired and other configurations of components may be utilized as desired. The configurations of the sealing body 20 and the prosthetic valve 10 may be varied in embodiments, and may be utilized separately from each other, or in combination with other components disclosed herein.

Figure 29:
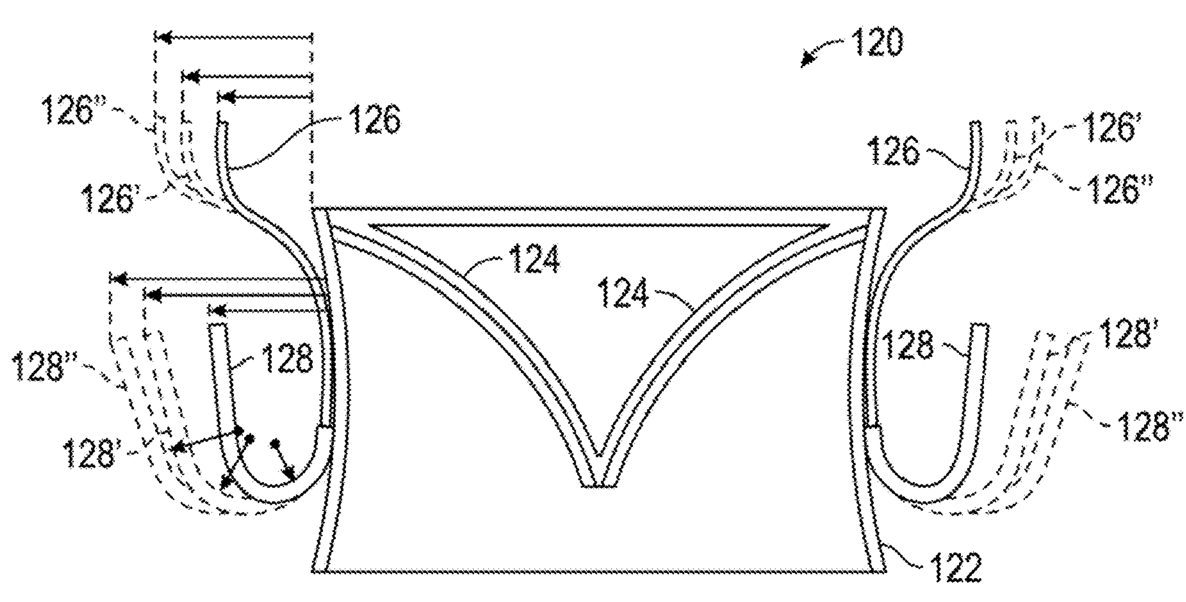
FIG. 29 illustrates a cross sectional schematic view of a modular prosthetic valve according to an embodiment of the present disclosure.

FIG. 29 illustrates an embodiment of a prosthetic valve 120 that is modular, in which components may be separately formed and coupled to each other. For example, as shown in FIG. 29, the valve 120 may include a valve body 122 having a plurality of prosthetic valve leaflets 124, and may have a proximal anchor 126 and a distal anchor 128. The valve body 122 may include a frame that supports the leaflets 124. The valve body 122 may be sized such that the leaflets 124 engage in proper coaptation with each other.

The proximal anchor 126 and/or the distal anchor 128 may be formed separately from the valve body 122 and may be coupled to the valve body 122 and to each other in embodiments. The prosthetic valve 120 may be formed of a modular system, in which components may be selected based on a desired configuration of the respective component, and then coupled to form the valve 120.

For example, the configurations of proximal anchors 126 and distal anchors 128 may each be selected from a plurality of different configurations of proximal anchors and distal anchors, respectively. The different configurations may correspond to different sizes of the valve 120, or may include other features. For example, different stiffness or method of anchoring may be selected. Different wall thickness tubing may be utilized. Each proximal anchor 126 selected may have a different configuration than other proximal anchors that are not selected, and each distal anchor 128 may have a different configuration than other distal anchors that are not selected.

The proximal anchors 126 may be selected from an inventory including each of the different configurations of proximal anchors, and the distal anchors 128 may be selected from an inventory including each of the different configurations of distal anchors. As such, during formation of the valve 120, a user such as a manufacturer, technician, or medical professional, may select the desired configuration of proximal anchor 126 from a plurality of different configuration of proximal anchors, and may select the desired configuration of distal anchor 128 from a plurality of different configurations of distal anchors. The selection may be based on the desired configuration of the anchors 126, 128. For example, the different configurations of proximal anchors and distal anchors may each be for anchoring to a different size native valve. The selection may be based on the size of the native valve that the anchor is configured to couple to, among other features.

FIG. 29 shows that the anchors 126, 128 may be selected from other configurations of anchors shown in dashed lines in FIG. 29. A proximal anchor 126' shown in dashed lines for example, may be configured to couple to a native valve having a larger size than the anchor 126 is configured to couple to. Similarly, a proximal anchor 126" may be configured to couple to a native valve having an even larger size. The respective distances that the anchors 126, 126', 126" extend from the valve body 122 may be at a different extent than each other, as marked in FIG. 29. The lengths of each of the proximal anchors 126, 126', 126" may vary from each other.

Similarly, a distal anchor 128' shown in dashed lines for example, may be configured to couple to a native valve having a larger size than the distal anchor 128 is configured to couple to. Similarly, a distal anchor 128" may be configured to couple to a native valve having an even larger size. The respective distances that the anchors 128, 128', 128" extend from the valve body 122 may be at a different extent than each other, as marked in FIG. 29. The lengths and radii of curvature of each of the distal anchors 128, 128', 128" may vary from each other.

As such, a user may determine a size of a native valve that the prosthetic valve 120 is to be implanted to, and may select a configuration of proximal anchor and distal anchor that corresponds to that size. The user may then assemble the prosthetic valve 120 accordingly and may couple the selected configuration of distal anchors (e.g., anchors 128) and the selected configuration of proximal anchors (e.g., anchors 126) to the valve body 122. The valve body 122 may be configured to be coupled to one of the configurations of distal anchors 128 selected from a plurality of different configurations of distal anchors (e.g., 128, 128', and 128"), and the valve body 122 may be configured to couple to one of the configurations of proximal anchors 126 selected from a plurality of different configurations of proximal anchors (e.g., 126, 126', and 126"). The valve body 122 may remain a single size or configuration. As such, improvements in the manufacture of the prosthetic valve 120 may result, as a single configuration of valve body 122 may be utilized to couple to a variety of sizes of native valves by selecting a desired configuration of proximal anchor and distal anchor. A single valve frame for the valve body 122 may be utilized that is configured to be coupled to the plurality of different configurations of distal anchors 128, 128', 128" and the different configurations of the proximal anchors 126, 126', 126".

In embodiments, the configuration of the valve body 122 may be selected from a variety of different configurations of valve bodies as well.

In embodiments, the proximal anchors may comprise atrial anchors configured to be positioned on an atrial side of a native valve, and the distal anchors may comprise ventricular anchors configured to extend around a native valve leaflet. Other configurations of anchors may be utilized as desired. The prosthetic valve may be configured to be implanted in a native mitral valve or a native tricuspid valve, although the prosthetic valve and modular system for the valve may be utilized for other locations of implantation as desired.

Figure 30:
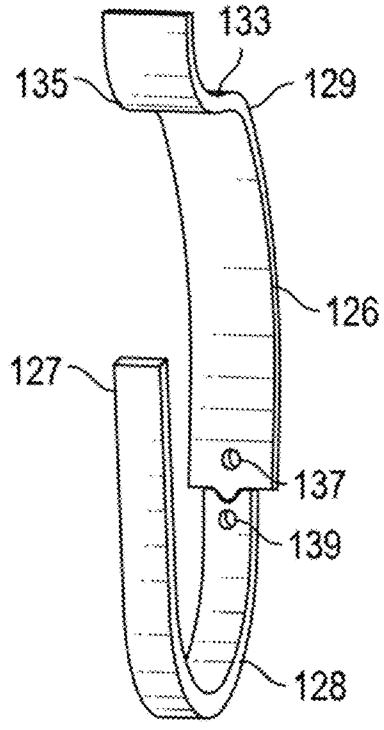
FIG. 30 illustrates a perspective view of a proximal anchor coupled to a distal anchor according to an embodiment of the present disclosure.

FIG. 30 illustrates a manner of coupling the proximal anchor 126 to the distal anchor 128. A distal end of the proximal anchor 126 may couple to a proximal end of the distal anchor 128 and may couple to the valve body 122. The coupling may include a pin that may extend through an aperture 137 in the proximal anchor 126. The distal anchor 128 may couple to the valve body 122 in a similar manner, via an aperture 139 in the distal anchor 128. The anchors 126, 128 may each couple to an outer surface of the valve frame of the valve body 122 via a pin extending through a respective aperture, or in another manner.

The anchors 126, 128 may each curve radially outward from the valve body 122, with the distal anchor 128 having a single curve positioning a tip 127 of the anchor 128 proximally. The proximal anchor 126 may have an initial curve 129 extending radially outward and may lead to a curve 135 extending the tip of the anchor 126 proximally. The anchor 126 may be shaped to support a skirt on an intermediate portion 133 between the curves 129, 135 according to embodiments. The anchor 126 may hold the skirt taut.

Figure 31:
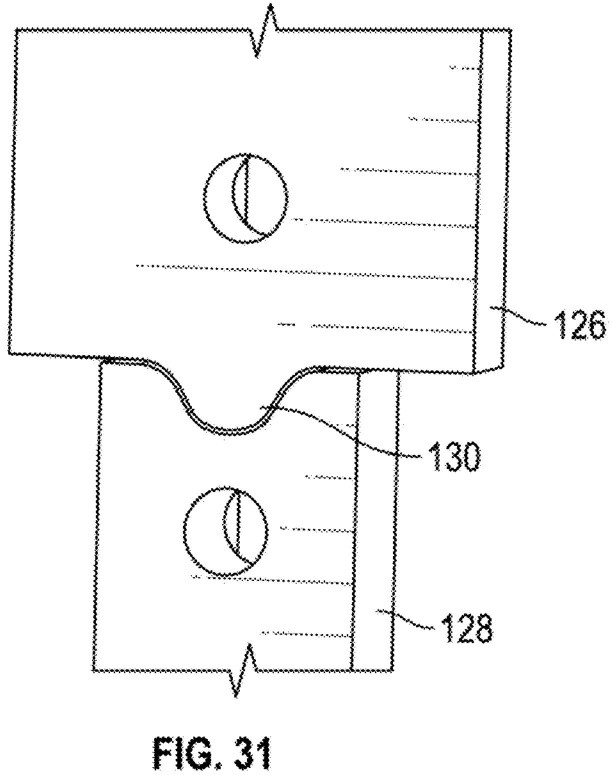
FIG. 31 illustrates a close up view of a portion of the coupling between the proximal anchor and the distal anchor according to an embodiment of the present disclosure.

Notably, as shown in FIG. 31, a lock 130 may be provided that may couple the proximal anchor 126 to the distal anchor 128. The lock 130 may be configured to prevent rotation of the proximal anchor 126 relative to the distal anchor 128 when the anchors 126, 128 are coupled to the valve body 122. A user may lock the end of the anchors to each other to prevent rotation of the selected configuration of anchors. The lock 130, for example, may comprise an insert entering a recess, which may be positioned on the proximal end of the distal anchor 128 as shown in FIG. 31 or in embodiments may be positioned on the distal end of the proximal anchor 126. The presence of the lock 130 may reduce the number of pins and apertures required to secure the anchors 126, 128 to each other and to the valve body 122.

Figure 32:
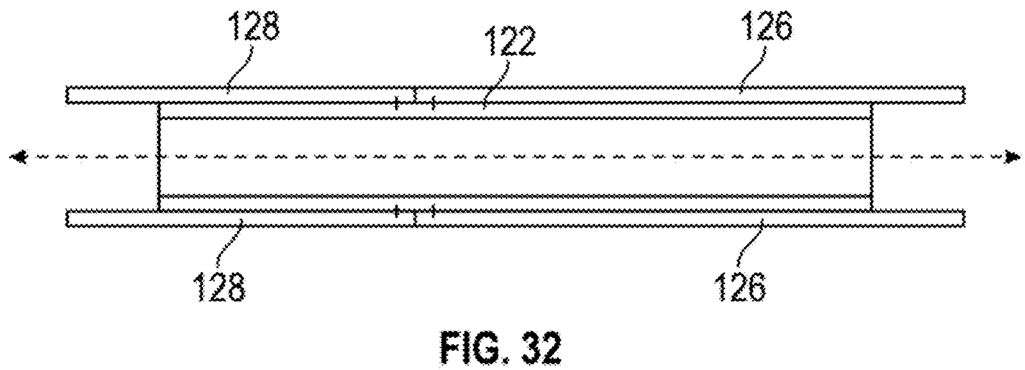
FIG. 32 illustrates a side schematic view of the prosthetic valve shown in FIG. 29 in a linearized configuration.

The proximal anchors and distal anchors may be coupled to each other and to the valve body 122 such that the anchors 126, 128 and the valve body 122 only form two circumferential layers while in a linearized configuration. Such a configuration is shown in FIG. 32. The reduced number of circumferential layers may reduce the overall profile of the valve when in a linearized configuration for deployment.

Figure 33:
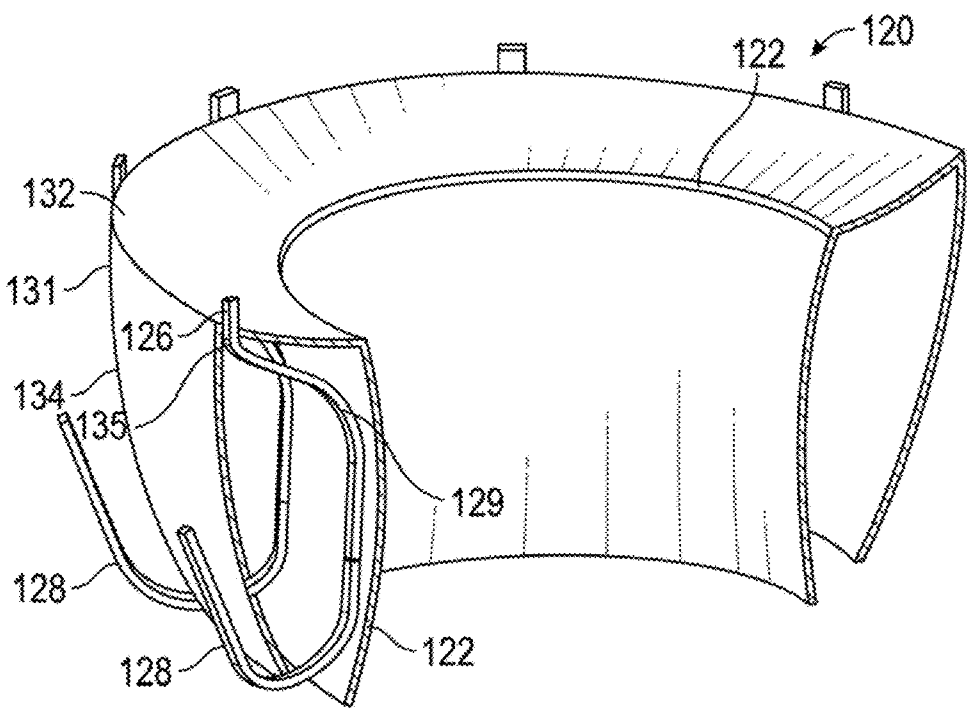
FIG. 33 illustrates a side cross sectional perspective view of the prosthetic valve shown in FIG. 29 including a skirt coupled thereto.

FIG. 33 illustrates a side perspective cross sectional view of the valve 120. A skirt 131 including an upper portion 132 and a side portion 134 may be provided to form a seal against a portion of the patient's body when the prosthetic valve 120 is implanted.

In embodiments, the skirt 131 may be held at a desired diameter by the proximal anchors 126, or "inflow anchors," and thus may achieve an expanded diameter that may operate in a similar manner as the sealing bodies as disclosed herein. The skirt 131 may be tensioned upward at an angle via the proximal anchors 126, which may make the tension in the skirt 131 provided by the proximal anchors 126 the primary sealing mechanism. The lower end of the skirt 131 proximate the distal anchors 128 or "outflow anchors" may be an open end in embodiments.

The skirt 131 may be configured to be positioned radially outward of the valve body 122 and coupled to one of more of the distal anchors, proximal anchors, and/or valve body. The configuration of the skirt 131 may be configured to be selected from a plurality of different configurations of skirts each configured to be positioned radially outward of the valve body 122. The configuration of the skirt 131 may be selected in a similar manner as the selection of the anchors, namely based on a size or other desired property of the skirt 131.

Similarly, a sealing body, for example, as disclosed herein may be utilized with the prosthetic valve. The configuration of the sealing body may be selected from a plurality of different configurations of sealing bodies, including properties such as size or another configuration of the sealing body. The sealing body may be positioned radially outward of the prosthetic valve leaflets of the valve body 122. The sealing bodies may operate in a similar manner as disclosed herein, and may seal fluid flow due to a missed capture of a leaflet by the anchors, for example, the distal anchors 128.

Variations in the prosthetic valve 120 and the modular prosthetic valve system may be provided as desired. The prosthetic valve 120 and the modular prosthetic valve system may be utilized in combination with other embodiments disclosed herein or solely. The prosthetic valve 120 may be implanted using similar methods as with the prosthetic valve 10 discussed herein, although other methods may be utilized as desired.

FIGS. 34-42 illustrate embodiments of prosthetic valves in which the distal anchors or ventricular anchors are configured with ensnaring features that are configured to couple to the chordae, trabeculae, or papillary structures of the patient's heart to anchor the prosthetic valve within the native valve.

Figure 34:
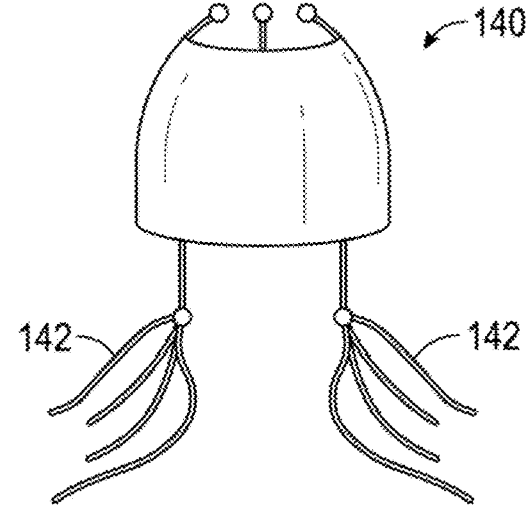
FIG. 34 illustrates a side schematic view of a prosthetic valve according to an embodiment of the present disclosure.
Figure 35:
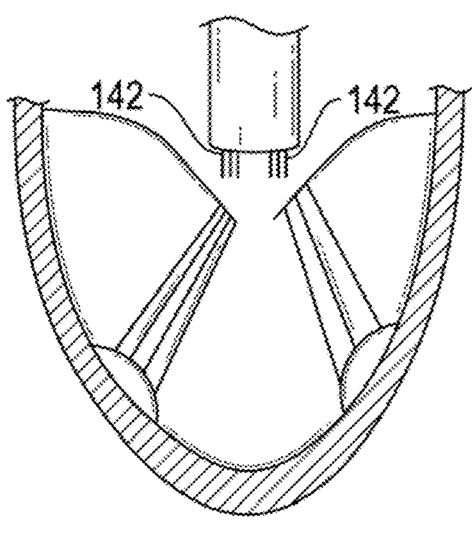
FIG. 35 illustrates a side schematic view of the prosthetic valve shown in FIG. 34 being deployed.
Figure 36:
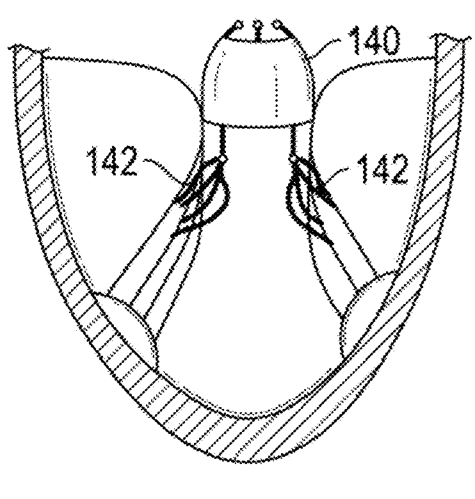
FIG. 36 illustrates a side schematic view of the prosthetic valve shown in FIG. 34 deployed.

In the embodiment shown in FIGS. 34-36, the prosthetic valve 140 may include ensnaring features that may comprise wires 142 that may be spaced from each other in an array. The wires 142 may be configured to extend between and entangle within the chordae, trabeculae, or papillary structures of the patient's heart. The wires 142 may be configured to be in a undeployed or linearized configuration prior to deployment, and then may deploy to couple to the chordae, trabeculae, or papillary structures.

FIG. 35, for example, illustrates the prosthetic valve 140 being deployed from a capsule of a delivery apparatus, with the wires 142 in a linearized configuration. Upon deployment, as shown in FIG. 36, the wires 142 may extend outward and extend between and entangle with the chordae, trabeculae, or papillary structures of the patient's heart. The wires 142 may serve to anchor the valve 140 within the patient's native valve. The anchors accordingly may not anchor to the leaflets, but rather to the chordae, trabeculae, or papillary structures of the patient's heart.

In embodiments, the wires 142 may be made of a shape memory material, such as Nitinol or another form of shape memory material, and are biased to move to the deployed configuration shown in FIG. 36 from an undeployed configuration. The wires 142 may be biased to the configuration in which the ensnaring features couple to the chordae, trabeculae, or papillary structures.

Figure 37:
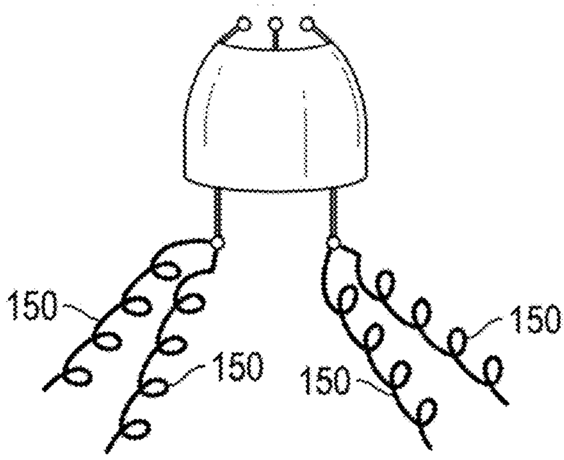
FIG. 37 illustrates a side schematic view of a prosthetic valve according to an embodiment of the present disclosure.
Figure 38:
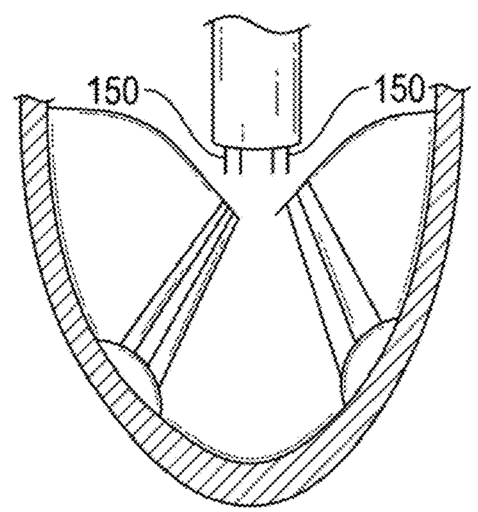
FIG. 38 illustrates a side schematic view of the prosthetic valve shown in FIG. 37 being deployed.
Figure 39:
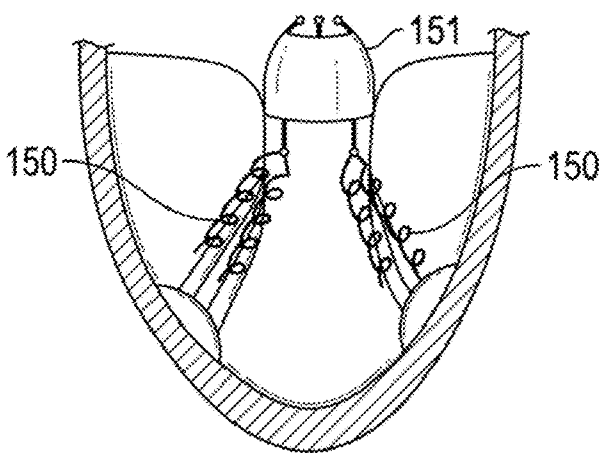
FIG. 39 illustrates a side schematic view of the prosthetic valve shown in FIG. 37 deployed.

In the embodiment shown in FIGS. 37-39, the ensnaring features may comprise wires 150 that may comprise coils configured to wrap around and entangle within the chordae, trabeculae, or papillary structures of the patient's heart. The wires 150 may be configured to be in a undeployed or linearized configuration prior to deployment, and then may deploy to couple to the chordae, trabeculae, or papillary structures by forming a spiral.

FIG. 38, for example, illustrates the prosthetic valve 151 being deployed from a capsule of a delivery apparatus, with the wires 150 in a linearized configuration. Upon deployment, as shown in FIG. 39, the wires 150 may then wrap around and entangle within the chordae, trabeculae, or papillary structures of the patient's heart. The wires 150 may serve to anchor the valve within the patient's native valve. The anchors accordingly may not anchor to the leaflets, but rather to the chordae, trabeculae, or papillary structures of the patient's heart.

In embodiments, the wires 150 may be made of a shape memory material, such as Nitinol or another form of shape memory material, to move to the configuration shown in FIG. 39 upon deployment. The wires 150 for example, may be straightened in an undeployed or linearized configuration and may then move to the deployed or coiled configuration shown in FIG. 39 upon deployment.

Figure 40:
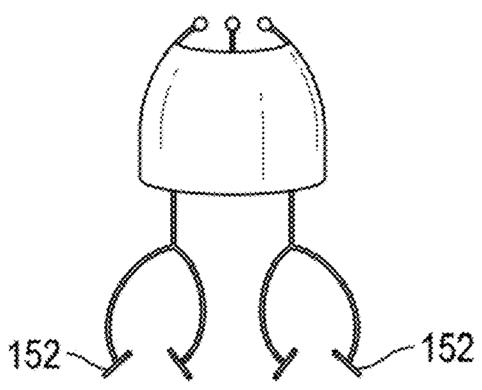
FIG. 40 illustrates a side schematic view of a prosthetic valve according to an embodiment of the present disclosure.
Figure 41:
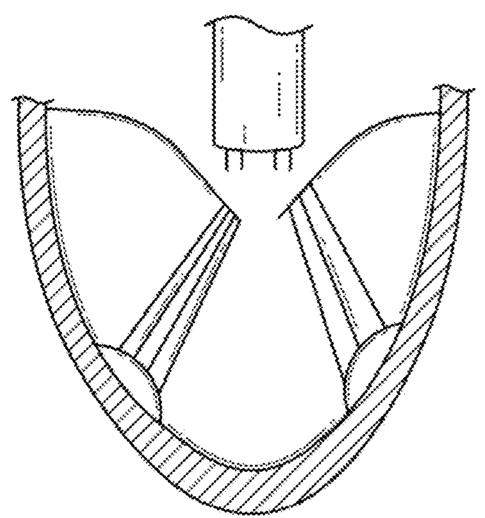
FIG. 41 illustrates a side schematic view of the prosthetic valve shown in FIG. 40 being deployed.
Figure 42:
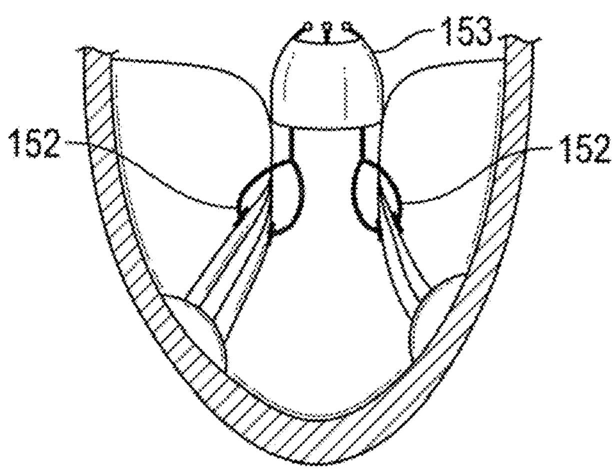
FIG. 42 illustrates a side schematic view of the prosthetic valve shown in FIG. 40 deployed.

In the embodiment shown in FIGS. 40-42, the ensnaring features may comprise one or more clamps 152 that may be configured to couple to the chordae, trabeculae, or papillary structures of the patient's heart. The clamps 152 may be configured to be in a undeployed or linearized configuration prior to deployment, and then may deploy to couple to the chordae, trabeculae, or papillary structures.

FIG. 41, for example, illustrates the prosthetic valve 153 being deployed from a capsule of a delivery apparatus, with the clamps 152 in a linearized configuration. Upon deployment, as shown in FIG. 42, the clamps 152 may then extend to press against and clamp the chordae, trabeculae, or papillary structures of the patient's heart to couple to the chordae, trabeculae, or papillary structures. The clamps 152 may serve to anchor the valve within the patient's native valve. The anchors accordingly may not anchor to the leaflets, but rather to the chordae, trabeculae, or papillary structures of the patient's heart.

In embodiments, the clamps 152 may be made of a shape memory material, such as Nitinol or another form of shape memory material, to move to the deployed configuration shown in FIG. 42 upon deployment. The clamps 152 for example, may be straightened in the undeployed or linearized configuration and may then move to the deployed or clamped configuration shown in FIG. 42 upon deployment. In embodiments, a separate mechanism may be utilized to deploy and clamp the clamps 152. The force of the clamps 152 upon the chordae, trabeculae, or papillary structures accordingly may be controlled by the mechanism.

The prosthetic valves may be utilized for deployment with mitral or tricuspid valves, or in embodiments may be utilized in other implantation locations as desired. The features of the ensnaring features may be utilized with other embodiments herein, or may be utilized solely. The prosthetic valves may be implanted with similar methods as with the prosthetic valve 10 discussed herein, although other methods may be utilized as desired.

FIGS. 43-51 illustrate embodiments of prosthetic valves in which one or more anchors are configured to engage calcification of a native valve to anchor a prosthetic valve to a native valve.

Figure 43:
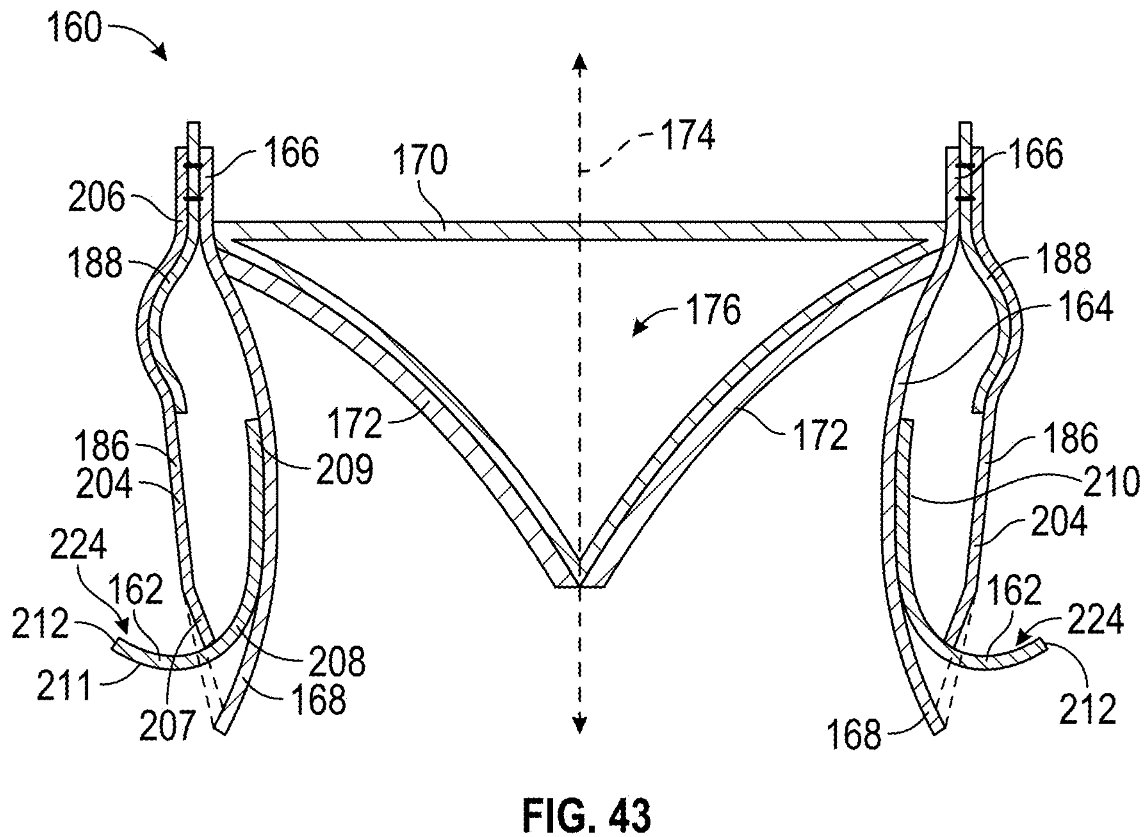
FIG. 43 illustrates a cross sectional schematic view of a prosthetic valve according to an embodiment of the present disclosure.

FIG. 43, for example, illustrates an embodiment of a prosthetic valve 160 including anchors 162 that are configured to engage calcification of a native valve to anchor the prosthetic valve 160 to a native valve. The prosthetic valve 160, as shown in FIG. 43, may be configured to be deployed to a native valve and may include a valve frame 164, having a proximal portion 166 including a proximal end of the valve frame 164 and a distal portion 168 including a distal end of the valve frame 164. The valve frame 164 may have a shape from the proximal portion 166 to the distal portion 168 that bows inward in embodiments. In other embodiments, other shapes of valve frames 164 may be utilized as desired.

The valve frame 164 may be coupled to an intermediate body 170 that may be configured similarly as the intermediate body 23 shown in FIG. 3. The intermediate body 170 may couple to a plurality of prosthetic valve leaflets 172 that may be configured similarly as the prosthetic valve leaflets 16 shown in FIG. 1. The valve frame 164 may be configured to support the prosthetic valve leaflets 172 within the patient's native valve when the prosthetic valve 160 is implanted.

The prosthetic valve 160 and the prosthetic valve leaflets 172 may be configured to extend around a central axis 174 of the prosthetic valve 160. The central axis 174 may extend through a flow channel 176 of the prosthetic valve 160 that is similar to the flow channel 25 shown in FIG. 3.

The valve frame 164 may have a variety of forms, and may include a plurality of struts that join at junctures to form the valve frame 164. The configuration of the valve frame 164 may be similar to the configurations of other embodiments of valve frames disclosed herein, as desired.

The prosthetic valve 160 may include atrial or proximal anchors 188 that may extend radially outward from the valve frame 164. The atrial or proximal anchors 188 may be positioned at the proximal portion 166 of the valve frame 164 in embodiments, and may extend radially outward from the proximal portion 166 to anchor to the atrial side of the native valve, and particularly the atrial side of the native valve annulus. The atrial or proximal anchors 188 may be configured as arms that extend radially outward from the valve frame 164, or may have another configuration in embodiments as desired.

A sealing body 204 may be coupled to the valve frame 164 and may be positioned radially outward from the valve frame 164. The sealing body 204 may comprise a skirt, and may have a proximal portion 206 that may be positioned at the proximal portion 166 of the valve frame 190 and may have a distal portion 207 that may be coupled to the distal anchors 162. In embodiments, the coupling point of the distal portion 207 of the sealing body 204 may vary, and may be coupled to the distal portion 168 of the valve frame 164 as shown in dashed lines in FIG. 43. Other coupling points may be utilized in embodiments as desired.

The sealing body 204 may be positioned radially outward of the atrial or proximal anchors 188 as shown in FIG. 43, or in embodiments may be positioned radially inward of the atrial or proximal anchors 188. The sealing body 204 may extend around the entirety of the valve frame 164 and in embodiments may be configured to press against the interior surface of the native valve to seal at the interior surface of the native valve.

The anchors 162 may comprise distal anchors and may be positioned at a distal portion of the prosthetic valve 160 and the distal portion 168 of the valve frame 164. The anchors 162 may be configured to extend radially outward from the valve frame 164 and may be in the form of arms or other forms of anchors that extend radially outward from the valve frame 164. The anchors 162 may each include a proximal portion 208 and a distal portion 211. The proximal portion 208 of the anchors 162 may be coupled to the valve frame 164 and the distal portion 211 of the anchors 162 may extend radially outward from the valve frame 164.

Figure 44:
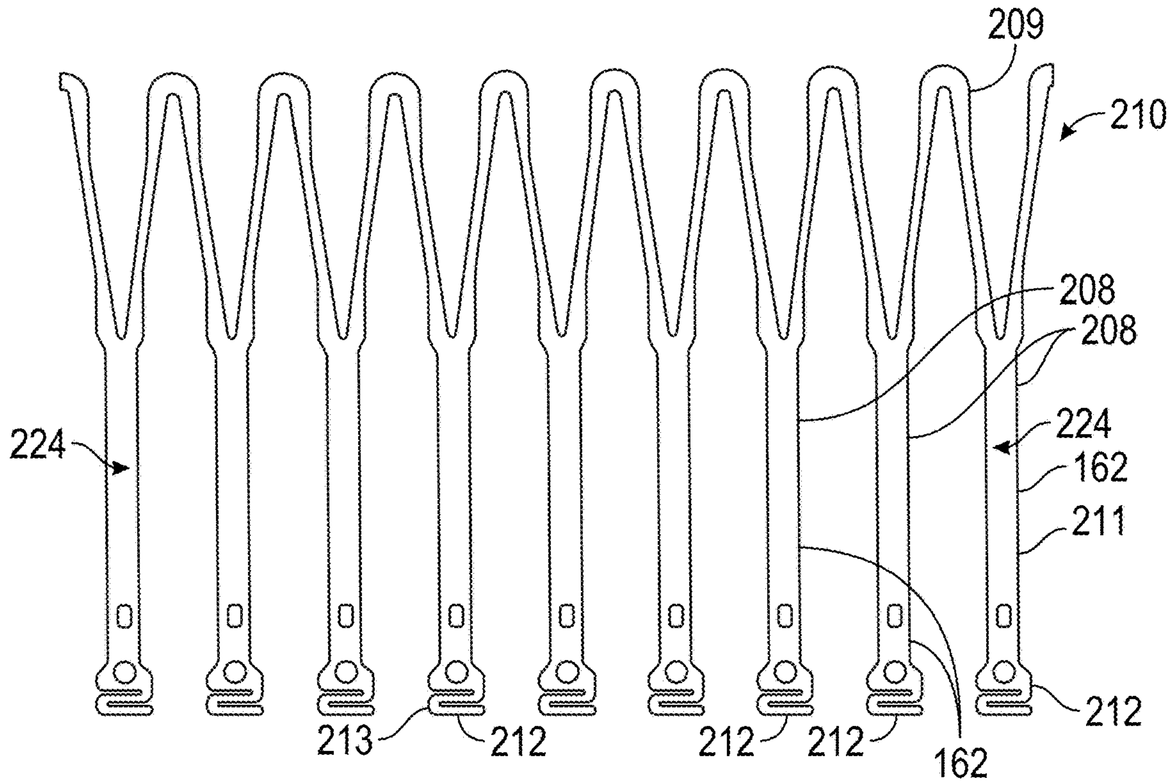
FIG. 44 illustrates a plan view of distal or ventricular anchors shown in FIG. 43.

FIG. 44, for example, illustrates a plan view of a pattern of the anchors 162. The anchors 162 may be coupled to a frame 210, and may be positioned at a distal portion of the frame 210. The plan view is a representation of a flattened pattern of the anchors 162 and the frame 210, with the frame 210 in use being wrapped around the valve frame 164 to have a cylindrical shape, with the anchors 162 bent radially outward and extending radially outward from the frame 210. The frame 210 may include a proximal portion 209 that extends around the valve frame 164 and couples to the valve frame 164. The anchors 162 may extend radially outward from the frame 210. Each anchor may be configured as an elongate arm as shown in FIG. 44, or may have another configuration as desired.

Figure 45:
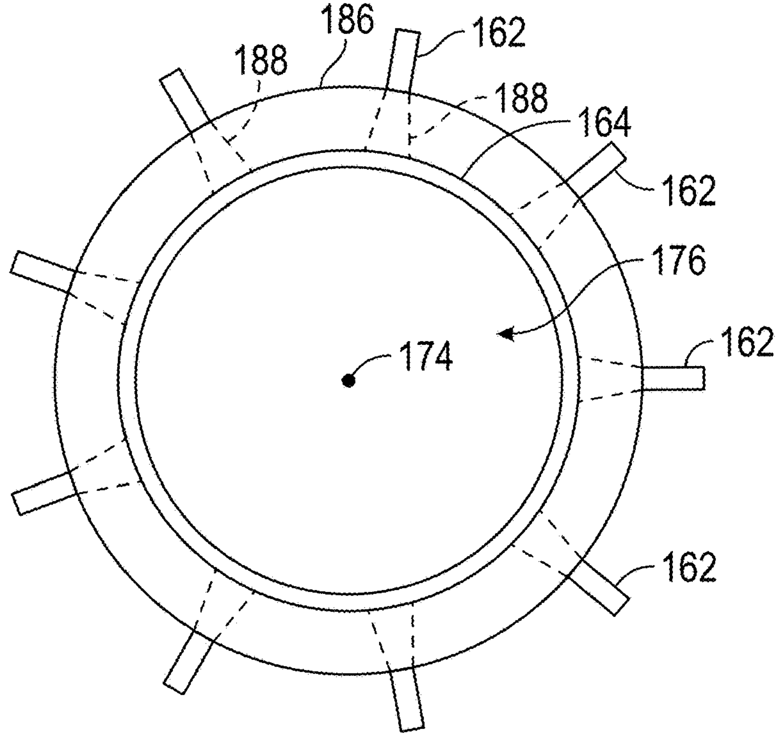
FIG. 45 illustrates a top schematic view of the prosthetic valve shown in FIG. 43.

FIG. 45, for example, illustrates the radial extension of the anchors 162 relative to the valve frame 164. The proximal anchors 188 are further marked in dashed lines within the sealing body 186. The anchors 162, 188 may comprise nine anchors as shown in FIG. 45, or a greater or lesser number may be utilized as desired. The spacing of the distal anchors 162 may be equal to each other, or may differ in embodiments. The spacing of the proximal anchors 188 may be equal to each other, or may differ in embodiments. The proximal anchors 188 and distal anchors 162 may be aligned at the same circumferential position as shown in FIG. 45 or may have a different position relative to each other as desired.

Referring back to FIG. 44, a distal tip 212 of each anchor 162 may be flexible in embodiments. The tip 212, for example, may include an undulating feature 213 such as a rachis feature that may provide flexibility for the distal tips 212. In embodiments, other configurations of the tips 212 may provide flexibility as desired. For example, the tips 212 may be made of a flexible material or may have another structure that provides flexibility. In embodiments, the tips 212 may be covered with a material that provides flexibility for the tip of the respective anchor 162.

In embodiments, the tips 212 may be wider than the proximal portions 208 of the anchors 162. Such a feature may enhance the surface area of the tips 212 to reduce the possibility of the distal tips 212 puncturing a portion of the patient's heart wall undesirably in embodiments.

Referring to FIG. 43, the anchors 162 may be bent radially outward from the frame 164 such that the anchors 162 extend horizontally relative to the central axis 174 to a tip 212 of the respective anchor 162. Such a configuration may differ from a configuration as shown in FIG. 3 for example, in which the distal anchors 17 extend vertically with respect to a central axis of the prosthetic valve 10 to hook around the native leaflets as shown in the leftmost side of FIG. 6. The horizontal extension of the anchors 162 as shown in FIG. 43 may account for the presence of calcification positioned radially outward of the native valve leaflets, which may block the hooking of the leaflet shown on the leftmost side of FIG. 6. In embodiments, the anchors 162 may be configured to extend perpendicular with respect to the central axis 174, or may extend at another angle as desired. The anchors 162 may be straight or may have a curvature as shown in FIG. 43. The curvature may be configured to contour to a shape of the calcification in embodiments.

The anchors 162 may be configured to extend over a distal tip of a native leaflet and horizontally from the distal tip of the native leaflet to the tip 212 of the respective distal anchor 162. Such a configuration may allow the anchors 162 to engage the calcification to anchor the prosthetic valve 160 to the native valve.

Figure 46:
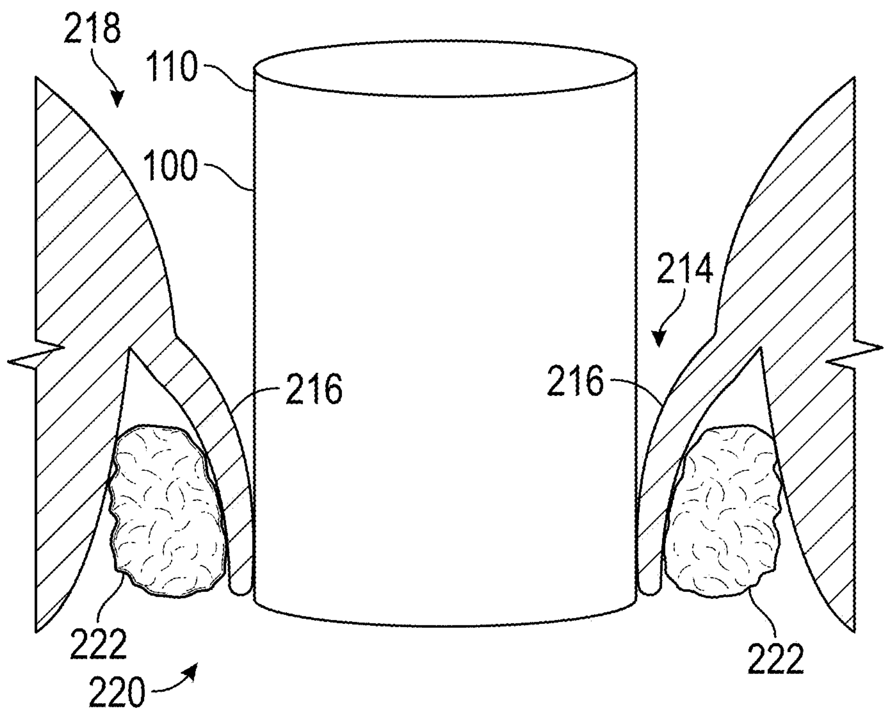
FIG. 46 illustrates a schematic view of a delivery apparatus extending to a patient's native valve.
Figure 47:
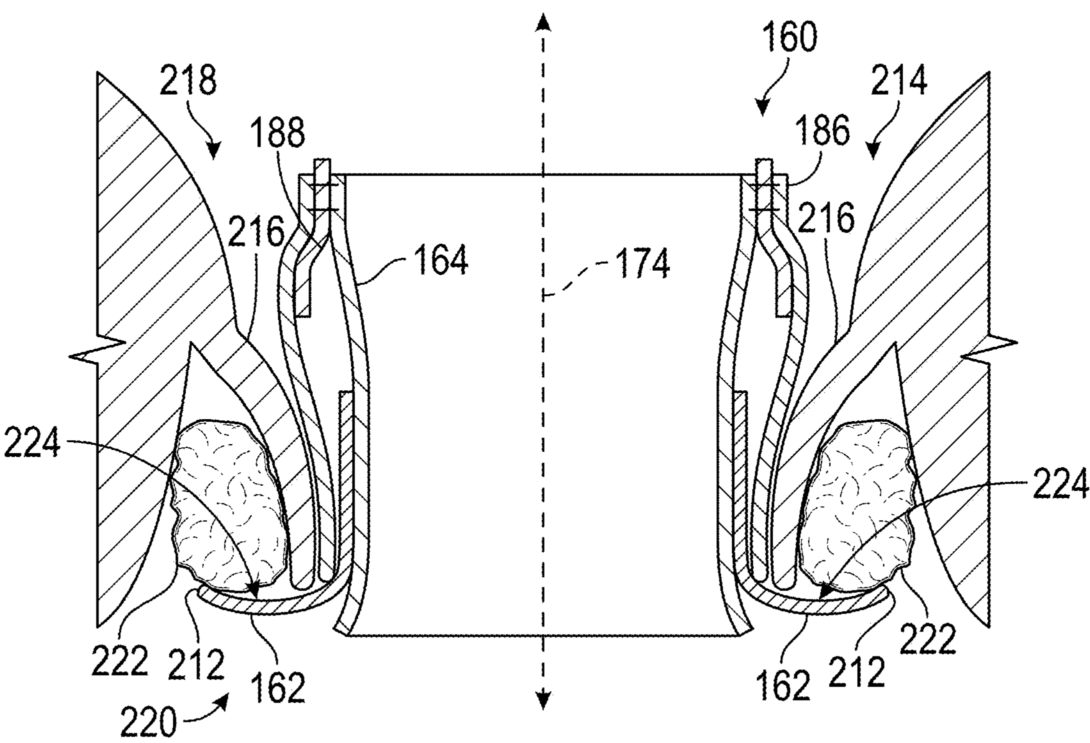
FIG. 47 illustrates a cross sectional schematic view of the prosthetic valve shown in FIG. 43 implanted within a patient's native valve.

FIGS. 46 and 47, for example, illustrate a deployment of the prosthetic valve 160 to a native valve 214. The native valve 214 may include native valve leaflets 216 positioned between an atrial side 218 of the native valve 214 and a ventricular side 220 of the native valve 214. The native valve 214 may have calcification 222, which may be positioned radially outward of one or more of the native valve leaflets 216 of the native valve 214 on the ventricular side 220 of the native valve 214. As shown, the position and size of the calcification 222 may impede the ability of vertically extending distal anchors to properly engage the native valve leaflets 216. Such a feature may result in a miscapture of one or more of the leaflets 216 by distal anchors. The calcification 222 may comprise annular calcification, such as mitral annular calcification, or other forms of calcification in embodiments.

FIG. 46 illustrates a capsule 110 of a delivery apparatus 100, similar to the capsule and delivery apparatus shown in FIG. 25, positioned proximate the native valve leaflets 216 and in position to deploy the prosthetic valve 160. FIG. 47 illustrates the prosthetic valve 160 having been deployed by the delivery apparatus 100, with the calcification 222 have been engaged with the one or more anchors 162. Certain features of the prosthetic valve 160 such as the prosthetic valve leaflets 172 have been excluded from view in FIG. 47. The anchors 162 extend horizontally from the valve frame 164 and relative to the central axis 174 such that the anchors 162 engage the calcification 222 to anchor the prosthetic valve 160 to the native valve 214. The one or more anchors 162 are positioned distal of the calcification 222 and extend radially outward from the valve frame 164. The one or more anchors 162 extend over a distal tip of a native valve leaflet 216 and horizontally from the distal tip of the native valve leaflet 216 to the tip 212 of the respective anchor 162. Additional anchors such as the atrial or proximal anchors 188 may be utilized for further anchoring to the native valve 214.

Each anchor 162 may include a proximal surface 224 that may be configured to engage the calcification 222. The proximal surface 224 may abut the calcification 222 to engage the calcification 222, as shown in FIG. 47 for example. The proximal surface 224 may comprise an engagement surface for abutting against the calcification 222 in embodiments. Such anchoring may replace the anchoring provided by distal anchors hooking around the native valve leaflets and abutting the outward facing surface of the native leaflets as shown in the leftmost side of FIG. 6 for example.

Figure 48:
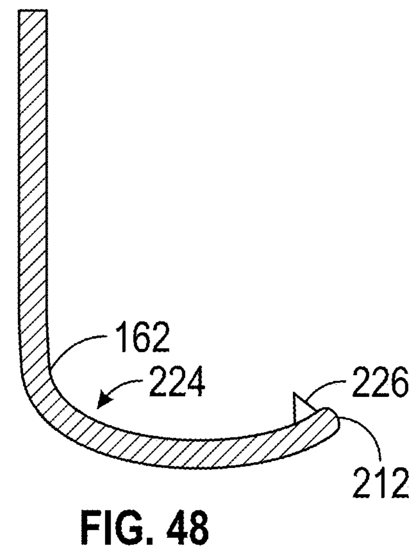
FIG. 48 illustrates a side schematic view of an anchor including a barb.

In embodiments, one or more of the anchors 162 may include one or more barbs 226 that may be configured to engage the calcification 222. FIG. 48 illustrates the one or more barbs 226, for example, may be positioned on the anchors 162, such as on a proximal surface 224 of the anchors 162. The one or more barbs 226 may extend proximally from the proximal surface 224 of the anchors 162. The barbs 226 may be positioned at the tips 212 of the anchors 162 to form a penetrating tip for the one or more of the anchors 162. Other positions may be utilized as desired.

Figure 49:
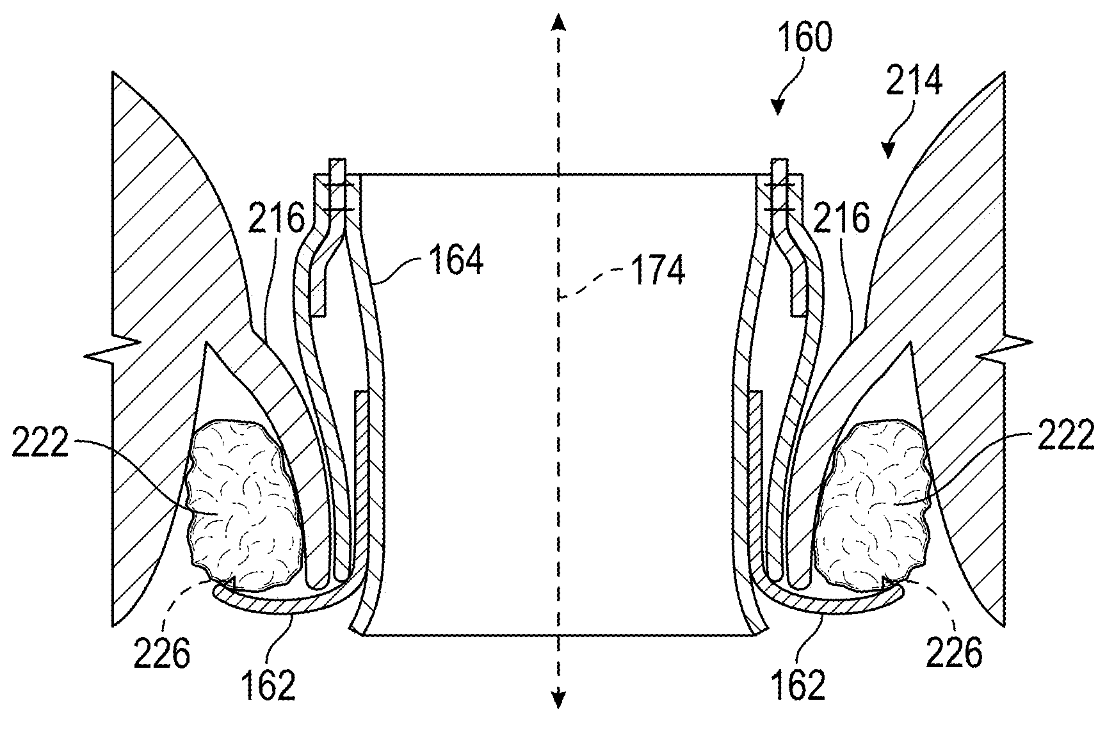
FIG. 49 illustrates a cross sectional schematic view of a prosthetic valve implanted within a patient's native valve according to an embodiment of the present disclosure.

FIG. 49, for example, illustrates the prosthetic valve 160 deployed to the native valve 214, with the barbs 226 engaging the calcification 222 to anchor the prosthetic valve 160 to the native valve 214. The barbs 226 engage the calcification 222 by penetrating the calcification 222 with the anchors including the barbs 226.

Figure 50:
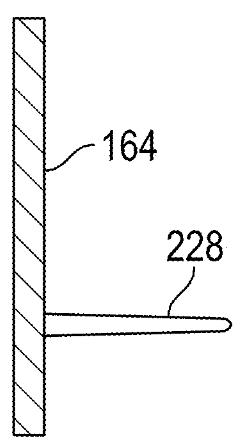
FIG. 50 illustrates a side schematic view of a valve frame including a barb.

In embodiments, one or more barbs configured to engage the calcification may extend from the frame of the prosthetic valve 160, for example, from the valve frame 164. FIG. 50 illustrates a side cross sectional view of a portion of the valve frame 164, including a barb 228. The barb 228 may extend radially outward from the valve frame 164 and may extend outward from an outer surface of a prosthetic valve that is configured to be positioned radially inward of the native valve leaflets of the native valve 214.

Figure 51:
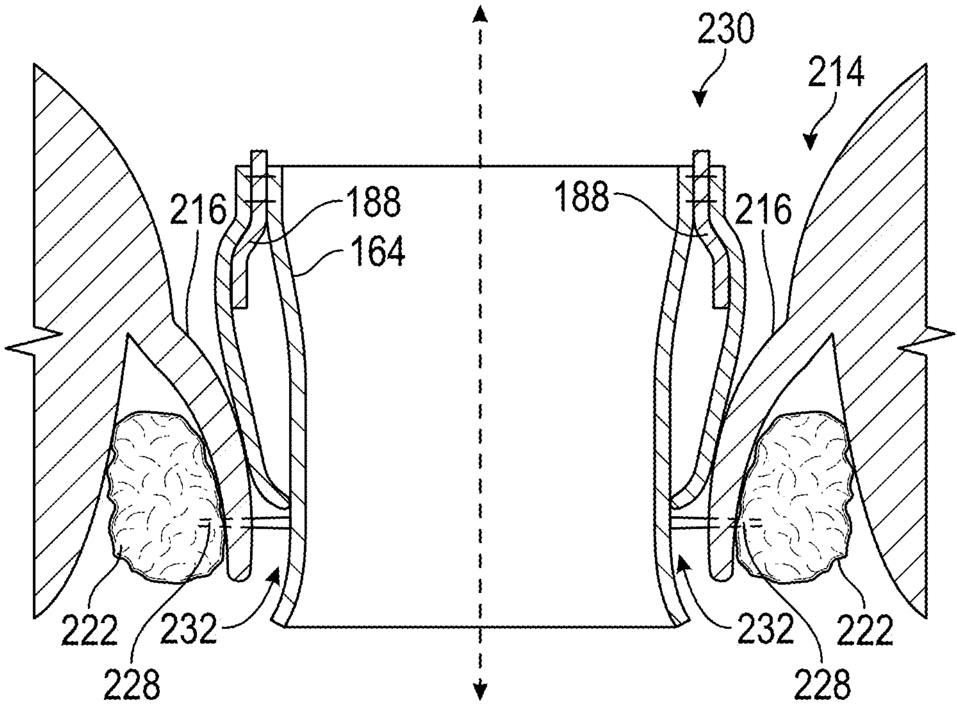
FIG. 51 illustrates a cross sectional schematic view of a prosthetic valve implanted within a patient's native valve according to an embodiment of the present disclosure.

FIG. 51 illustrates an example of such a configuration. The prosthetic valve 230 is deployed to the native valve 214 and the barbs 228 extend radially outward from the valve frame 164 and outward from an outer surface 232 of a prosthetic valve 230 that is configured to be positioned radially inward of the native valve leaflets 216 of the native valve 214. The outer surface 232 is positioned radially inward of the native valve leaflets 216 of the native valve 214.

The barbs 228 may be configured to pass through one or more of the native valve leaflets 216 of the native valve 214 to engage the calcification 222. The barbs 228 may have a length sufficient to pass through the native valve leaflets 216 and engage the calcification 222. The barbs 228 engage the calcification 222 by penetrating the calcification 222 with the anchors in the form of barbs 228.

In a configuration in which the barbs 228 are utilized as anchors, the distal anchors 162 may be excluded from such an embodiment. As such, the prosthetic valve 230 shown in FIG. 51 may exclude use of the distal anchors 162. In embodiments, a combination of the barbs 228, and the distal anchors 162 may be utilized, as well as other anchors as desired. Various combinations of anchors may be utilized as desired.

The prosthetic valves may be utilized for deployment with mitral or tricuspid valves, or in embodiments may be utilized in other implantation locations as desired. The prosthetic valves may utilize annular calcification such as mitral annular calcification for anchoring in embodiments, or other forms of calcification. The features of the anchors configured to engage calcification of the native valve to anchor the prosthetic valve to the native valve may be utilized with other embodiments herein, or may be utilized solely. The prosthetic valves may be implanted with similar methods as with the prosthetic valve 10 discussed herein, although other methods may be utilized as desired.

Various modifications of the embodiments disclosed herein may be provided. Combinations of features across embodiments may be provided as desired.

Figure 52:
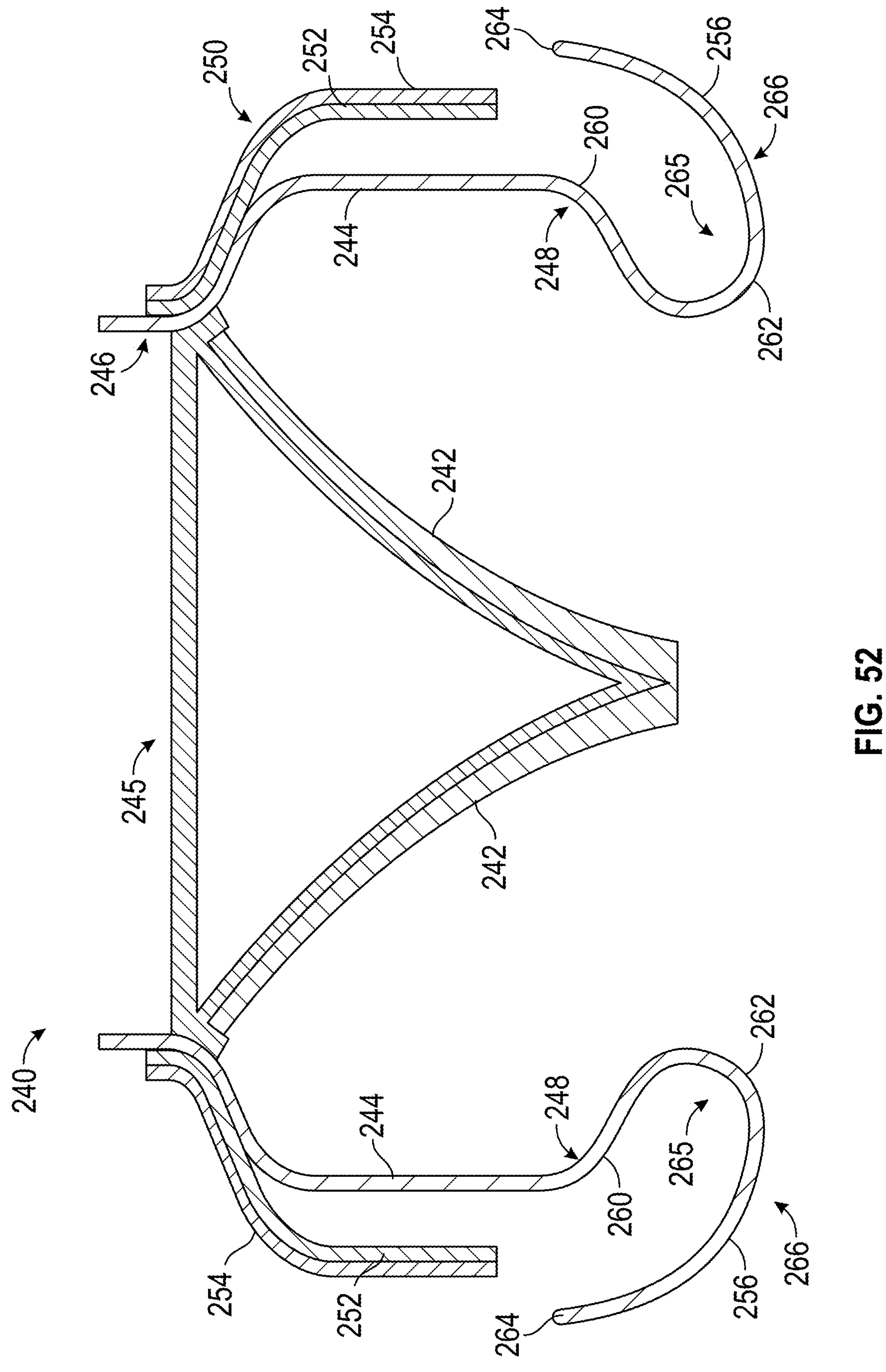
FIG. 52 illustrates a cross sectional schematic view of a prosthetic valve according to an embodiment of the present disclosure.

FIG. 52 illustrates a schematic cross sectional view of an embodiment of a prosthetic valve 240 configured to be deployed to a native valve. The prosthetic valve 240 may include a plurality of prosthetic valve leaflets 242, and may include a frame 244 supporting the plurality of prosthetic valve leaflets 242. In embodiments, the frame 244 may include a proximal portion 246 and a distal portion 248, and may surround a central channel 245 for fluid flow through the prosthetic valve 240. The proximal portion 246 in embodiments may comprise an inflow portion of the prosthetic valve 240 and the distal portion 248 may comprise an outflow portion of the prosthetic valve 240 in embodiments.

The prosthetic valve 240 may include a sealing body 250 that may include an outer frame 252 and a skirt 254. In embodiments, the configuration of the prosthetic valve 240 may be varied from the configuration shown in FIG. 52.

The prosthetic valve 240 may include one or more anchors 256 that may be utilized for anchoring the prosthetic valve to a desired implantation site. As shown in FIG. 52, the anchors 256 may be coupled to the distal portion 248 of the frame 244 and may extend radially outward from the frame 244. In embodiments, the anchors 256 may be coupled to another portion of the frame 244.

Each of the anchors 256 may include a proximal portion with a proximal end 260 that may couple to the distal portion 248 of the frame 244. The proximal portion may extend distally as shown in FIG. 52. In embodiments, the anchors 256 may include a bend portion 262 that may be adjacent to the proximal portion. The bend portion 262 may be configured to direct the respective anchor 256 proximally. The bend portion 262 may comprise a curve configured to direct a tip 264 of the anchor 256 proximally. The bend portion 262 may comprise a loop that extends radially inward in embodiments, as shown in FIG. 52, or may have another configuration as desired. The bend portion 262 may direct the anchor 256 to extend in an opposite direction. For example, as shown in FIG. 52, the bend portion 262 may direct the anchor 256 to extend at about 180 degrees from the proximal portion of the anchor 256.

In embodiments, the bend portion 262 may form a recess 265 for receiving a portion of a heart such as a native leaflet of a heart.

The anchors 256 may include an extension portion 266 that extends radially outward from the bend portion 262 and may extend radially outward to the tip 264 of the respective anchor 256.

In embodiments, the anchors 256 may comprise distal anchors positioned at a distal portion of the prosthetic valve 240. The anchors 256 may comprise ventricular anchors and may be configured to extend over a tip of a native leaflet of a native valve. For example, the anchors 256 may hook around the tip of the native leaflet with the native leaflet positioned within the recess 265 and the tip 264 of the anchor 256 positioned radially outward from the native leaflet.

In embodiments, the anchors 256 may be configured to deflect from an undeployed configuration to a deployed configuration. For example, in an undeployed configuration the anchors 256 may be elongated and may have a straightened configuration. In a deployed configuration the anchors 256 may deflect about the bend portion 262 to form the configuration shown in FIG. 52.

Figure 53A:
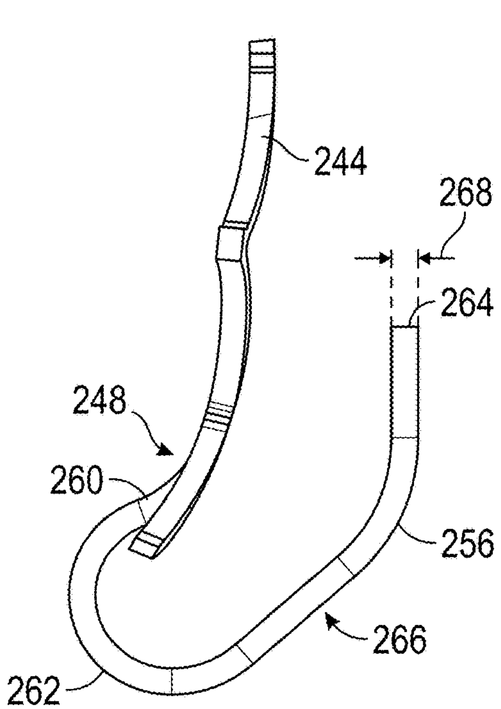
FIG. 53A illustrates a side view of a portion of a prosthetic valve.
Figure 53B:
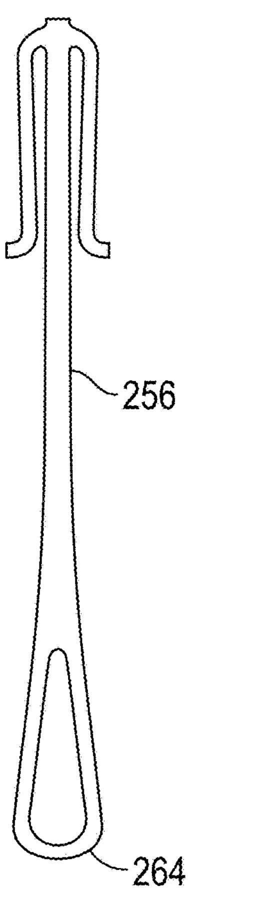
FIG. 53B illustrates a top view of an anchor shown in FIG. 53A.

FIG. 53A illustrates a side view of the anchor 256. The anchor 256 may include a thickness 268 that is uniform along a length of the anchor 256. FIG. 53B illustrates a top view of the anchor 256 in an undeployed or straightened configuration. FIG. 56C illustrates a side view of the anchor 256 in the undeployed or straightened configuration, with the thickness 268 of the anchor 256 shown to be uniform along the length and extent of the anchor 256.

Figure 53C:
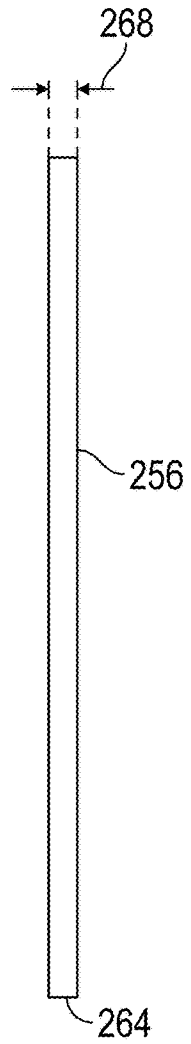
FIG. 53C illustrates a side view of the anchor shown in FIG. 53A.
Figures 54A, 54B, 54C:
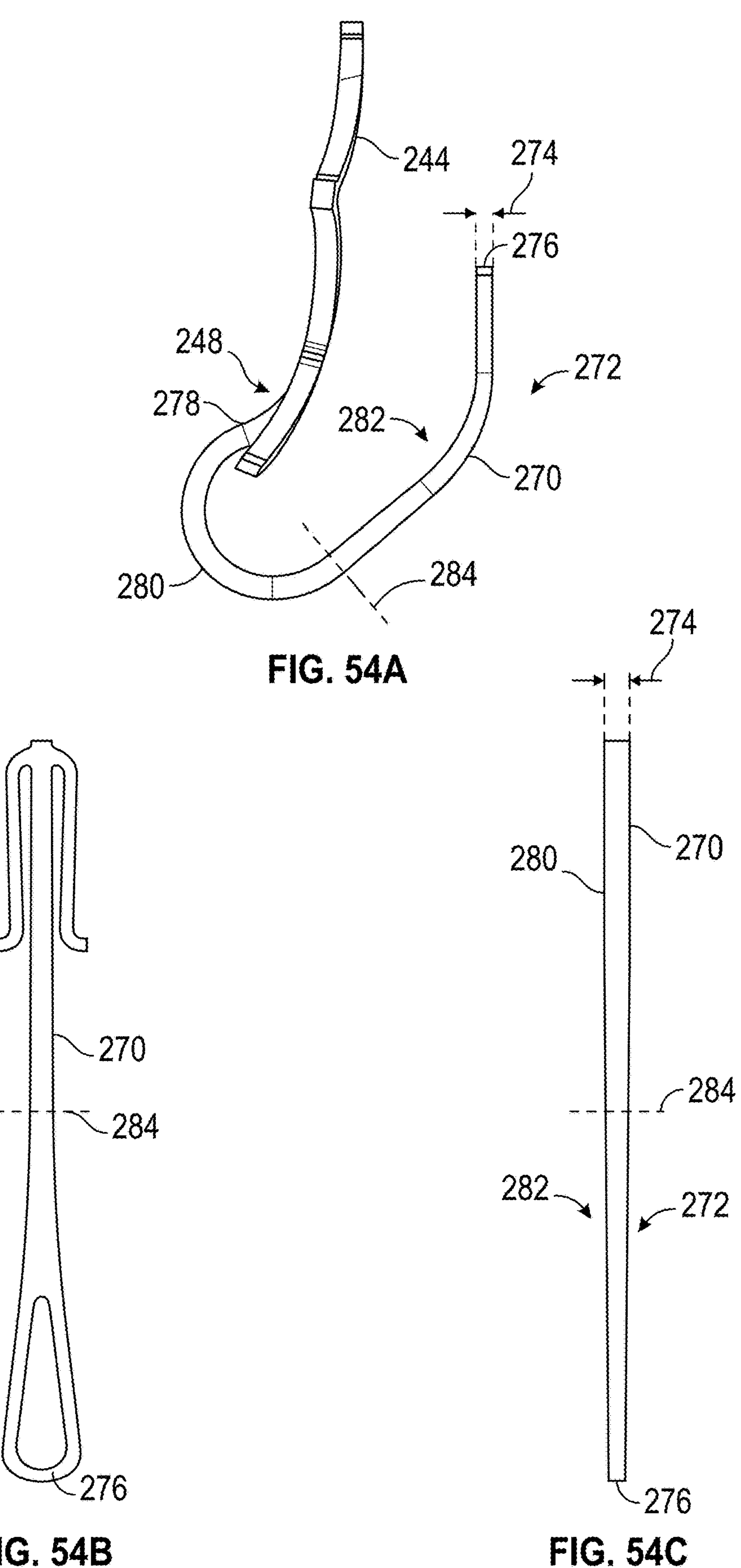
FIG. 54A illustrates a side view of a portion of a prosthetic valve according to an embodiment of the present disclosure.
FIG. 54B illustrates a top view of an anchor shown in FIG. 54A.
FIG. 54C illustrates a side view of the anchor shown in FIG. 54A.

In embodiments, one or more of the anchors may have a thickness that tapers downward in a direction towards the tip of the anchor. FIG. 54A, for example, illustrates a side view of an anchor 270 having a portion 272 with a thickness 274 that tapers downward in a direction towards the tip 276 of the anchor 270. The anchor 270 may otherwise be configured similarly as the anchor 256 shown in FIGS. 53A-C, including a proximal portion with a proximal end 278, a bend portion 280, and an extension portion 282 that may be otherwise configured similarly as the respective portions shown in FIG. 53A.

The anchor 270 may include a transition point 284 on the extension portion 282 at which the tapered thickness starts in a direction towards the tip 276. The thickness of the extension portion 282 accordingly may taper downward towards the tip 276 of the anchor 270, and may extend downward to the tip 276 of the anchor 270 as shown in FIG. 54A. FIG. 54C, for example, illustrates a side view of the elongated anchor 270 with the transition point 284 marked and the downward tapering of the thickness to the tip 276 shown. FIG. 54B illustrates a top view of the anchor 270 shown in FIG. 54C. A width of the anchor 270 may be uniform or may vary as desired.

In embodiments, the size of the portion of the anchor with the tapering thickness may vary. FIG. 55A, for example, illustrates an embodiment in which a bend portion 285 of the anchor 286 includes a thickness that tapers downward in a direction towards the tip 288 of the anchor 286. The transition point 290, for example, may be positioned at a proximal end of the bend portion 285, and the tapering may start proximal of the bend portion 285 and may continue through a loop formed by the bend portion 285. In embodiments, the tapered thickness may extend through the extension portion 292 and may extend to the tip 288 of the anchor 286. FIG. 55C, for example, illustrates a side view of the elongated anchor 286 with the transition point 290 marked and the downward tapering of the thickness to the tip 288 shown. FIG. 55B illustrates a top view of the anchor 286 shown in FIG. 55C. A width of the anchor 286 may be uniform or may vary as desired.

In embodiments, the portion of the anchor may have a thickness tapering downward in a direction towards the tip of the anchor to provide a dampening feature for the anchor. For example, as shown in FIG. 53A, the anchor 256 may be stiff along its length due to the uniform thickness 268 of the anchor 256. A tapered thickness, as shown in FIGS. 54A and 55A may allow for an increased flexibility of the respective anchor and a dampening of a force applied to the anchor. The tapering accordingly may produce fatigue resistance for the anchor and the prosthetic valve upon loads (which may be radial load or side loads) being applied to the anchor or the prosthetic valve. The loads may be produced by ventricular wall motion or other forces applied to the anchor or the prosthetic valve. The tapering may allow for fatigue strains to dissipate along a length of the anchor.

In embodiments, the amount of tapering may vary. For example, a variation in thickness of the anchor may be between 20% and 95% in embodiments, although other ranges may be provided. A variation in thickness may be 50% in embodiments.

The tapering may be a linear reduction in thickness, as shown in FIGS. 54C and 55C for example, or may be a nonlinear reduction. In embodiments, a reduction in thickness may comprise an undulation in the anchor, such as a rachis feature. In embodiments, only a portion of the anchor may be tapered as desired, or an entirety of an anchor may have a reduced thickness.

In embodiments, the prosthetic valve 240 may comprise a valve configured to be deployed to a native mitral valve or native tricuspid valve, among other implantation sites as desired. In an embodiment in which the prosthetic valve is deployed to a native mitral valve or tricuspid valve, the anchors may have a tapered thickness to dampen ventricular forces.

The features of the prosthetic valve 240, and the anchors of the prosthetic valve may be utilized solely or in combination with any other embodiment disclosed herein. The prosthetic valve 240 may be deployed to the implantation site utilizing deployment methods disclosed herein.

Figure 56:
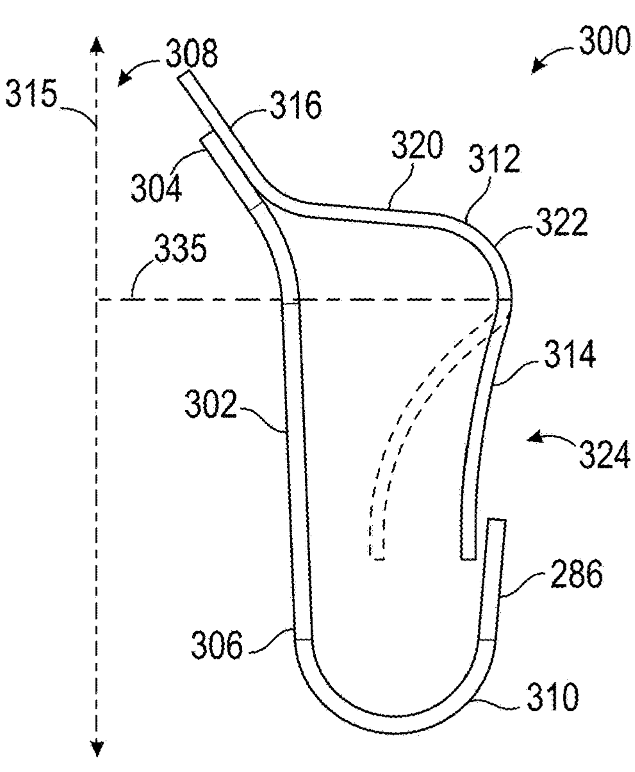
FIG. 56 illustrates a side cross sectional view of a portion of a prosthetic valve according to an embodiment of the present disclosure.

FIG. 56 illustrates a cross sectional schematic view of a half of a prosthetic valve 300 (the other half may comprise a mirror image thereof). The prosthetic valve 300 may be configured to be deployed to a native valve. The prosthetic valve 300 may include a plurality of prosthetic valve leaflets (not shown) and an inner frame 302 that may support the plurality of prosthetic valve leaflets. The inner frame 302 may include a proximal portion 304 and a distal portion 306. The inner frame 302 may be configured similarly as the frame 244 shown in FIG. 52 for example. The inner frame 302 for example, may surround a flow channel 308 for the prosthetic valve 300. The prosthetic valve 300 may include distal anchors 310 that may be configured similarly as the anchors 256 shown in FIG. 52, or may have another configuration as desired. The prosthetic valve 300 may extend around a central axis 315.

The prosthetic valve 300 may include a sealing body 312 that may be positioned radially outward of the inner frame 302. The sealing body 312 may include an outer frame 314 that may be positioned radially outward of the inner frame 302. In embodiments, the sealing body 312 may include a skirt (not shown) that may be configured similarly as skirts disclosed herein.

Figure 57:
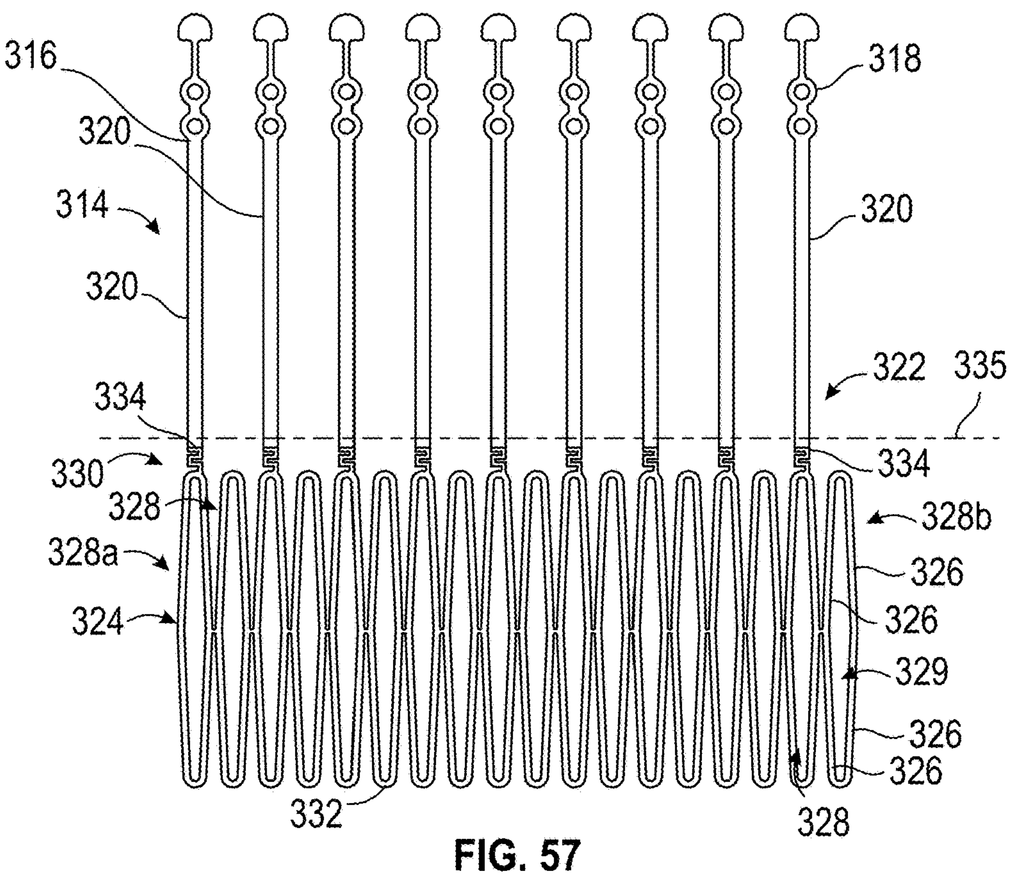
FIG. 57 illustrates a plan view of a frame of the prosthetic valve shown in FIG. 56 according to an embodiment of the present disclosure.

FIG. 57 illustrates a plan view of the outer frame 314 shown in FIG. 56, with the outer frame 314 shown flattened in FIG. 57. Referring to FIGS. 56 and 57, the outer frame 314 may include a proximal portion 316 that may be coupled to the proximal portion 304 of the inner frame 302. The proximal portion 316 for example, may be configured to be joined to the proximal portion 304 of the inner frame 302 via welding or sutures or another method as desired. The proximal portion 316 may include coupling bodies 318 that may be configured to couple to a portion of a delivery apparatus during a deployment procedure if desired.

In embodiments, a plurality of elongate strut arms 320 may extend from the proximal portion 316 of the outer frame 314 radially outward. The elongate strut arms 320 are shown in FIG. 57 for example, and may have a straightened shape. Referring to FIG. 56, the elongate strut arms 320 may extend radially outward from the central axis 315, and may extend radially outward in a plane of the central axis 315 as shown in FIG. 56. The plane of the central axis 315 may extend vertically and may extend outward from the central axis 315 similar to spokes extending radially outward from a central axis.

A distal portion of the elongate strut arms 320 may curve to extend axially and distally. For example, as shown in FIG. 56, a curved portion 322 may be formed that may curve distally. The curved portion 322 may orient a distal portion 324 of the outer frame 314 to extend axially distal.

Referring to FIG. 57, the distal portion 324 of the outer frame 314 may include a plurality of struts 326. The struts 326 may form a plurality of strut cells 328. The strut cells 328 may form a ring around the inner frame 302, with the strut cell 328*a* coupled to the strut cell 328*b* with the distal portion 324 wrapped around the inner frame 302 from the flattened configuration shown in FIG. 57.

The plurality of strut cells 328 may be joined to each other to form the ring about the inner frame 302, or may have another configuration as desired. Each strut cell 328 may include four sides bounding an opening 329 (as shown with strut cell 328*b*, for example), or may have another configuration as desired. Each strut cell 328, for example, may have a diamond shape as shown in FIG. 57, or may have another shape as desired.

The elongate strut arms 320 may each extend from the proximal portion 316 of the outer frame 314 to the plurality of strut cells 328 at the distal portion 324 of the outer frame 314. The plurality of strut cells 328 may include a proximal portion 330 that couples to a distal portion of the elongate strut arms 320 and the plurality of strut cells 328 may extend to a distal end 332 of the outer frame 314.

In embodiments, the outer frame 314 may include one or more deflection features 334 that may be configured to allow the plurality of strut cells 328 to deflect relative to the proximal portion 316 of the outer frame 314. The deflection feature 334 may be positioned as desired on the outer frame 314 and may have a variety of configurations. For example, as shown in FIG. 57, in embodiments, a deflection feature 334 may be positioned on each of the elongate strut arms 320. The deflection feature 334 may be positioned at a distal portion of the elongate strut arms and may be positioned at a coupling point between the elongate strut arm 320 and the proximal portion 330 of the strut cells 328.

The deflection feature 334 may be positioned to allow the portion of the outer frame 314 distal of line 335 shown in FIGS. 56 and 57 to deflect as desired. In embodiments, the deflection feature 334 may have another position as desired.

The deflection feature may comprise a portion of the elongate strut arms 320 that is more flexible that other portions of the elongate strut arms 320. The deflection feature accordingly may comprise a reduced strength portion of the elongate strut arms 320 that allows for deflection at the position of the deflection feature. In embodiments, the deflection feature may be included upon the elongate strut arms 320, or may be positioned on at least one of the plurality of struts of the outer frame 314 as desired. In embodiments, a deflection feature, for example, may be positioned on the struts of the strut cells 328. In embodiments, a deflection feature may be positioned on a combination of elongate strut arms 320 and the struts of the strut cells 328.

The deflection feature may comprise an undulation in one or more of the elongate strut arms 320. Referring to FIG. 57, for example, the undulation may extend circumferentially and the number of cycles of the undulation may be one or more cycles as desired. The undulation may comprise a rachis feature of the struts of the outer frame 314.

The length of the undulations may be set as desired, with FIG. 57 illustrating a relatively short length of the undulations. The length of the undulations may be set to determine an amount of flexibility provided by the deflection feature, with a shorter length corresponding to less flexibility and a longer length corresponding to greater flexibility. Various other configurations may be utilized as desired.

The deflection feature may allow the strut cells 328 to deflect to provide a non-circular shape of the ring formed by the strut cells 328. The deflection may have a variety of forms. For example, referring to FIG. 56, the strut cells 328 may be configured to deflect radially inward as represented by the dashed lines shown in FIG. 56. In embodiments, the strut cells 328 may be configured to deflect to form an oval shape or a "D" shape due to the deflection allowed by the deflection feature. Various other shapes of the ring formed by the strut cells 328 may be provided.

The deflection feature may allow the strut cells 328 to deflect to contour to a shape of an annulus of the native valve. For example, if the native valve has an oval shape or a "D" shape then the strut cells 328 may deflect to contour to such a shape. If the native valve annulus has calcification then the strut cells 328 may deflect to contour to such a shape produced by the calcification. The deflection feature may reduce the possibility of an LVOT obstruction in embodiments, and may enhance the sealing allowed by the outer frame 314 with the implantation site upon deployment.

The deflection feature may allow the strut cells 328 to deflect to reduce the possibility of paravalvular leakage between the sealing body 312 and the heart valve annulus in embodiments.

Figures 58, 59:
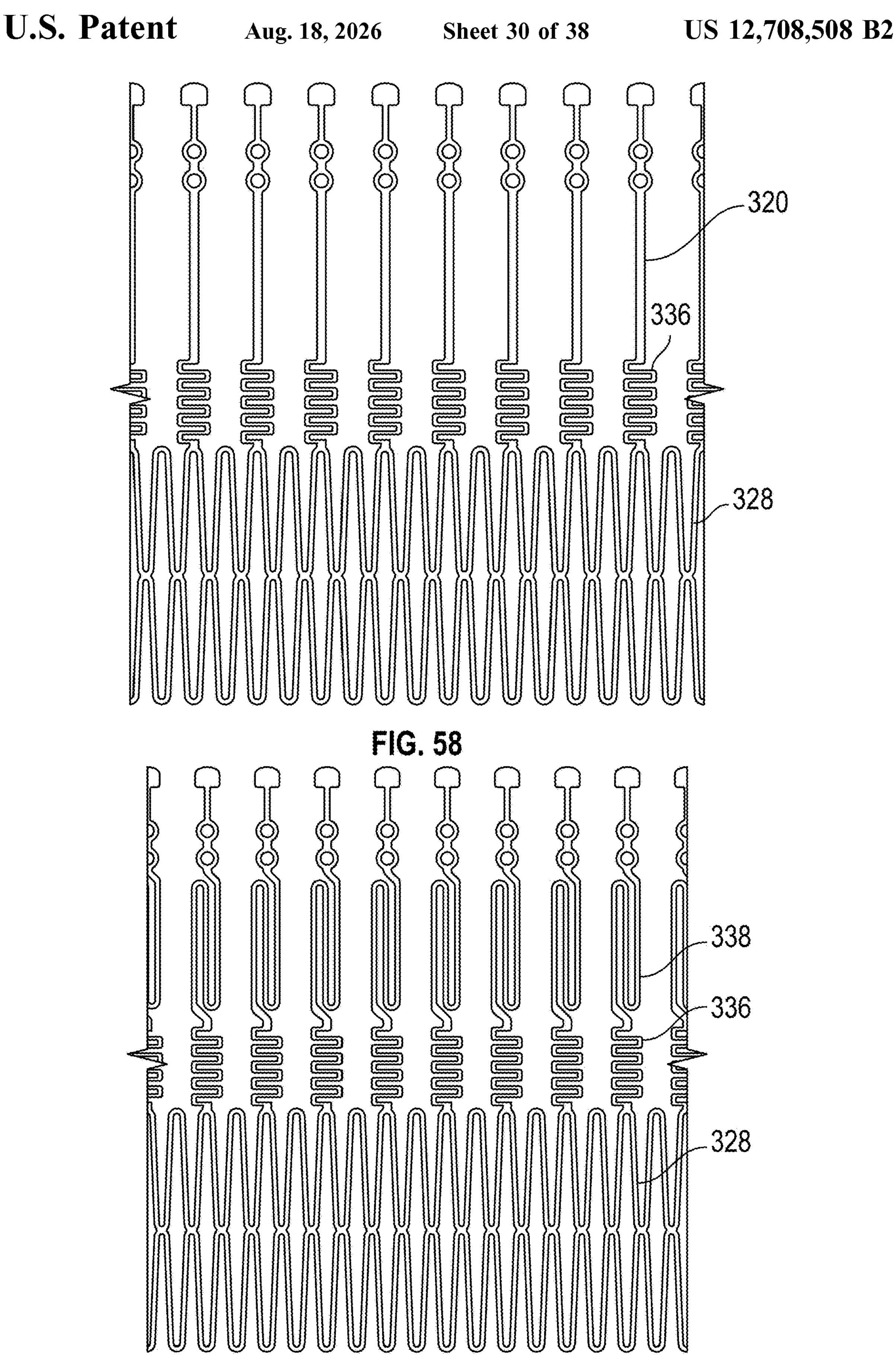
FIG. 58 illustrates a plan view of a frame according to an embodiment of the present disclosure.
FIG. 59 illustrates a plan view of a frame according to an embodiment of the present disclosure.

The configuration of the deflection feature may vary in embodiments. FIG. 58, for example, illustrates an embodiment in which the deflection feature 336 includes undulations having a greater length than shown in FIG. 57, and having greater spacing between the lengths of the undulations. Such a feature may provide for increased flexibility than provided by the deflection feature 334 shown in FIG. 57.

FIG. 59 illustrates an embodiment in which a deflection feature 336 with undulations extending circumferentially and a deflection feature 338 with undulations extending radially may be provided. The undulations that extend radially may have lengths that extend longer that the undulations of the deflection feature 336, and accordingly may have a greater flexibility than the undulations of the deflection feature 336. In embodiments, an elongate strut arm, or other strut of the outer frame 314, may include a combination of a first undulation extending circumferentially and a second undulation extending radially, among other combinations as desired. Further, combinations of undulations having varied lengths may be provided as desired.

Figure 60:
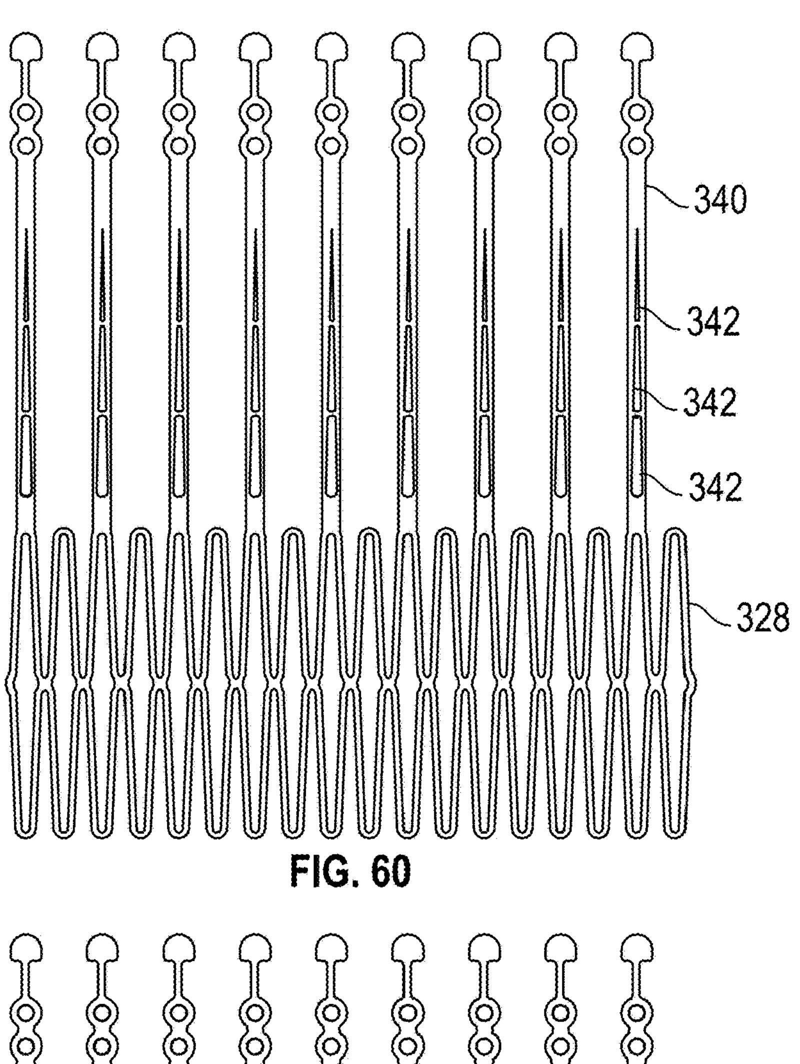
FIG. 60 illustrates a plan view of a frame according to an embodiment of the present disclosure.

In embodiments, the deflection feature may include one or more openings in an elongate strut arm. FIG. 60, for example, illustrates an elongate strut arm 340 including a plurality of openings 342. The openings 342 may remove material from the elongate strut arm 340 to accordingly increase a flexibility of the elongate strut arm 340. The openings 342 may have an elongate shape that may extend along a length of the elongate strut arm 340 in embodiments, as shown in FIG. 60, or may have another configuration as desired.

Figure 61:
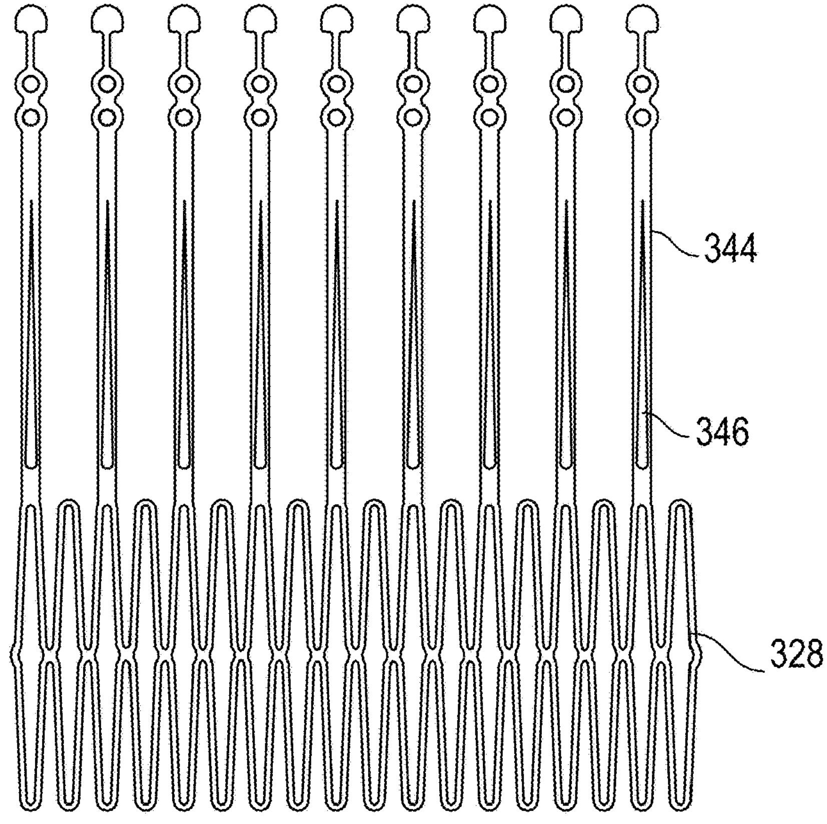
FIG. 61 illustrates a plan view of a frame according to an embodiment of the present disclosure.

FIG. 61 illustrates an elongate strut arm 344 having a single opening 346, with an elongate shape that extends along a length of the elongate strut arm 344.

In embodiments, combinations of deflection features may be provided. For example, combinations of undulations and openings, among other forms of deflection features may be provided as desired. In embodiments, at least one strut of the outer frame 314 may have an undulation or an opening configured to increase a flexibility of the frame, as well as combinations of an undulation and an opening, among other forms of deflection features.

The outer frame 314 in embodiments may be configured for sealing with a portion of the native valve, or may have another configuration in embodiments as desired. In embodiments, a skirt may be provided on the outer frame 314 for forming a seal with a portion of the native valve.

In embodiments, the prosthetic valve 300 may comprise a valve configured to be deployed to a native mitral valve or native tricuspid valve, among other implantation sites as desired. The features of the prosthetic valve 300 may be utilized solely or in combination with any other embodiment disclosed herein. The prosthetic valve 300 may be deployed to the implantation site utilizing deployment methods disclosed herein.

Figure 62A:
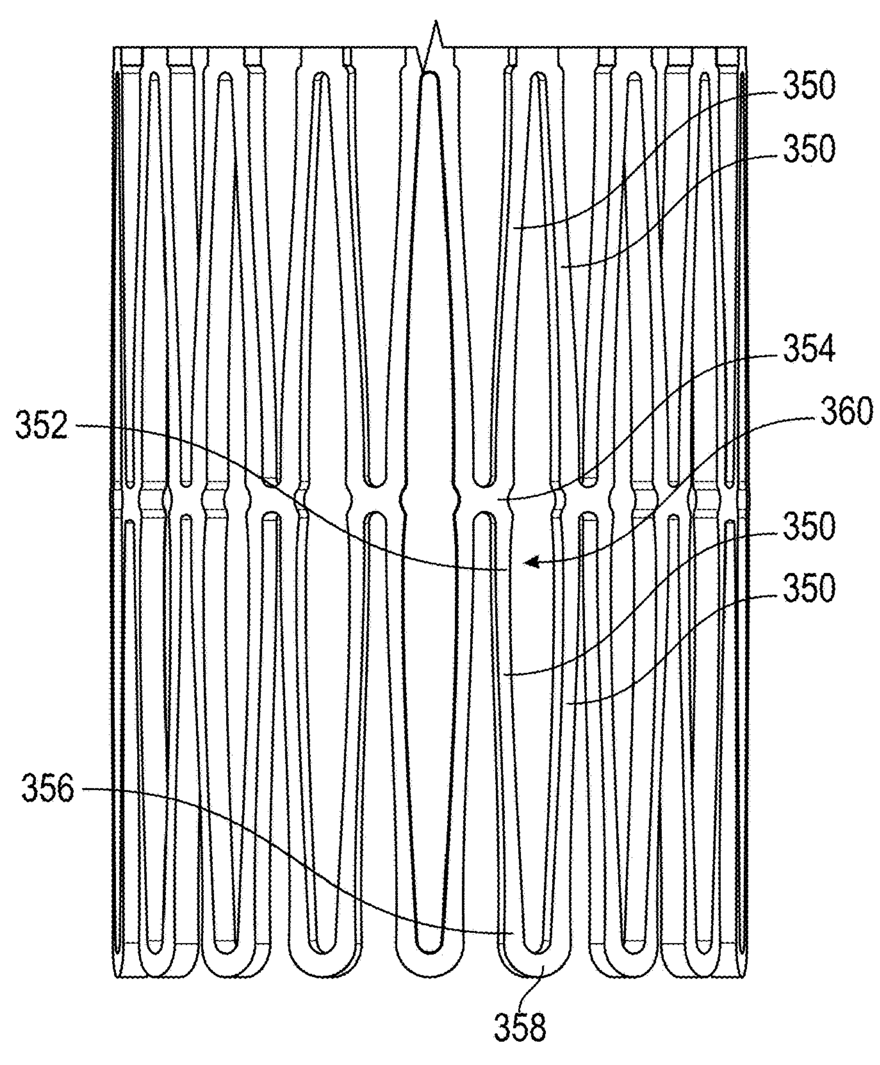
FIG. 62A illustrates a side view of a frame in an undeployed configuration.
Figure 62B:
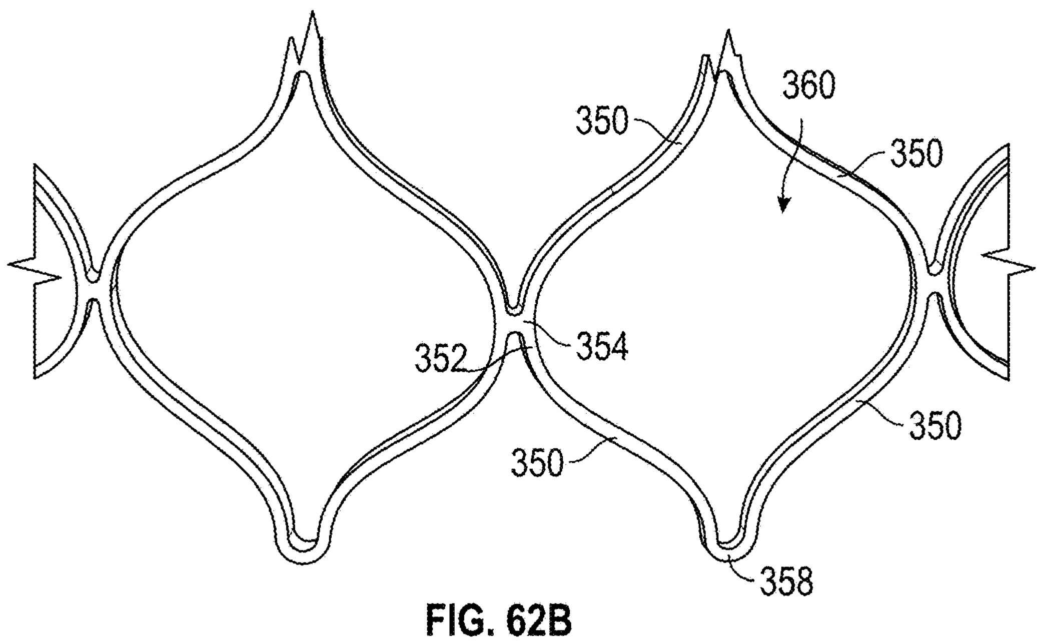
FIG. 62B illustrates a side view of a portion of the frame shown in FIG. 62A in an expanded configuration.

FIG. 62A illustrates a frame of a prosthetic valve including a plurality of struts 350. Each strut 350 may be straight and may extend from a first end 352 coupled to a juncture 354 to a second end 356 coupled to a juncture 358. The struts 350 may surround an opening 360 and may bound the opening 360 to form a strut cell. FIG. 62B illustrates the frame in an expanded or deployed configuration, with the struts 350 being pulled away from each other and a size of the opening 360 having increased.

Figure 62C:
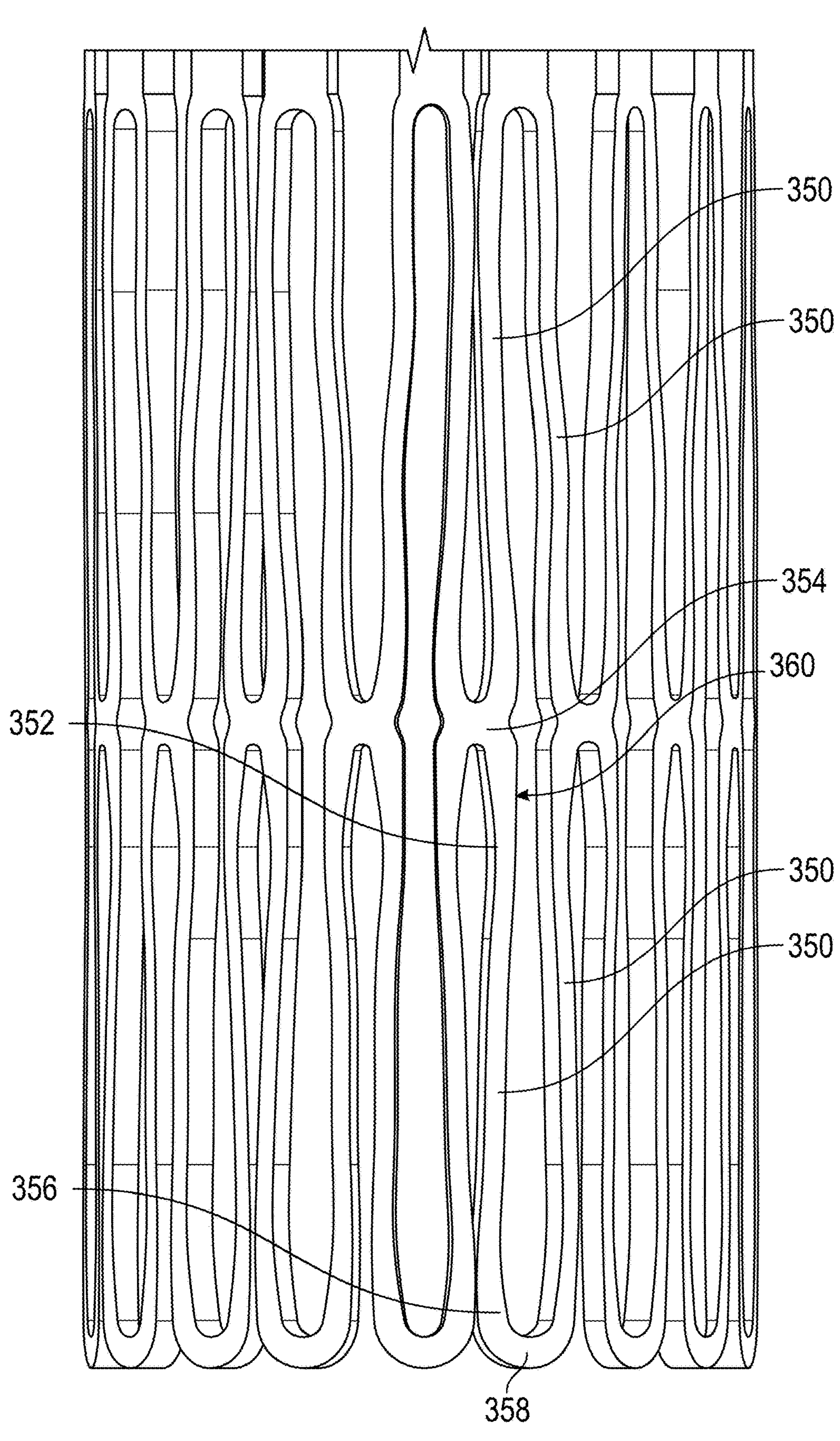
FIG. 62C illustrates a side view of the frame shown in FIG. 62A in a compressed configuration.

FIG. 62C illustrates the frame in a crimped configuration or undeployed configuration, with the struts 350 having been drawn towards each other and compressed together. With each strut 350 being straight, a strain may be provided at the ends 352, 356 of each strut 350. For example, with a radial compression applied to the struts 350 in the configuration shown in FIG. 62A to reach the crimped configuration or undeployed configuration shown in FIG. 62C, the ends 352, 356 of the struts 350 may bend and experience strain.

Figures 63A, 63B:
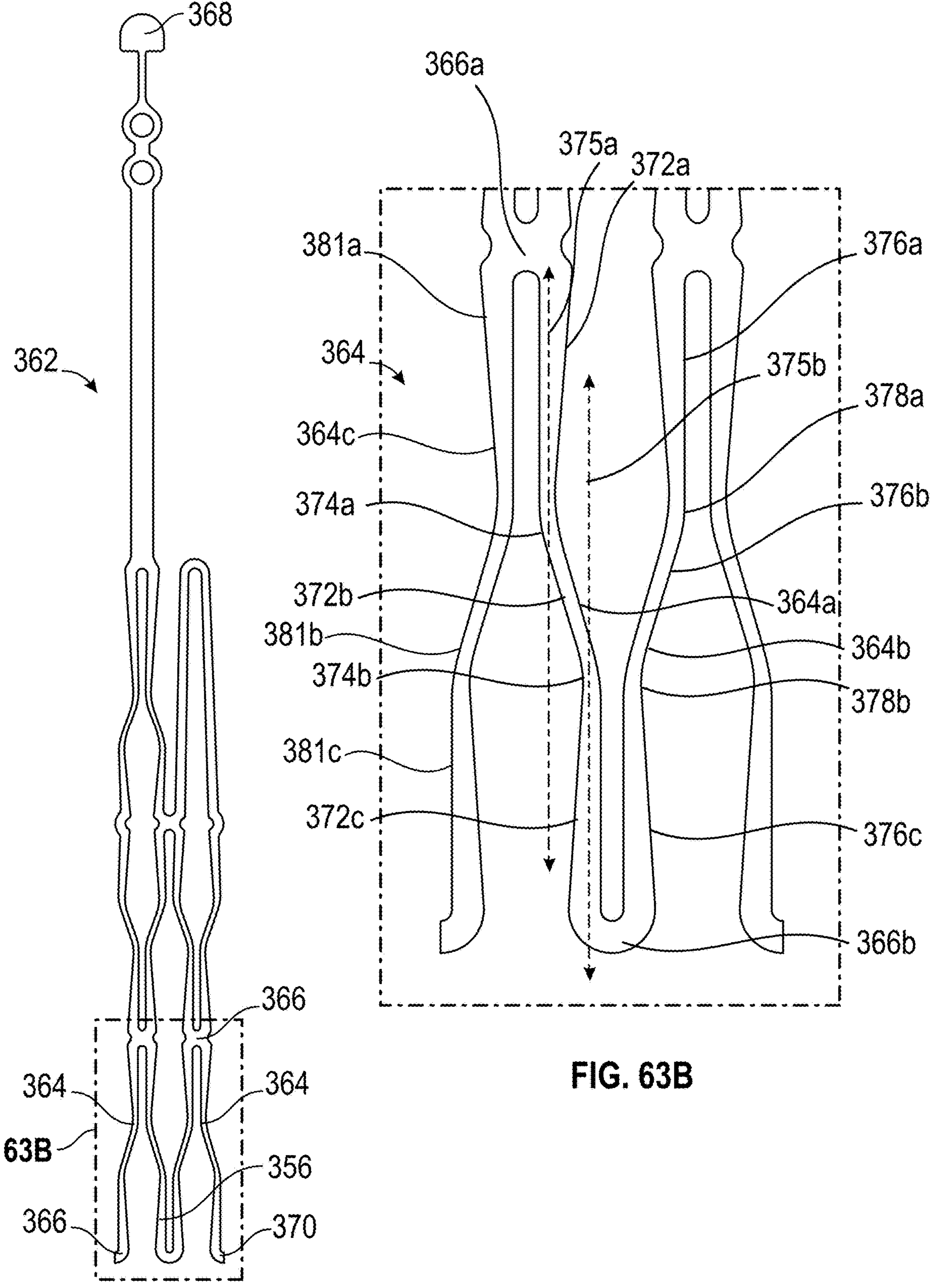
FIG. 63A illustrates a plan view of a portion of a frame according to an embodiment of the present disclosure.
FIG. 63B illustrates a view of a portion of the frame marked by 63B in FIG. 63A.

FIG. 63A illustrates a plan view of a portion of a frame 362 with struts that may reduce the adverse results of a straight strut as shown in FIG. 62A for example. FIG. 63A illustrates an embodiment of the frame 362 including a plurality of struts 364 joined at junctures 366. The frame 362 may include a proximal end 368 and a distal end 370, and the struts 364 may extend in a direction from the proximal end 368 towards the distal end 370.

FIG. 63B illustrates a close up view of a portion of the frame 362 (as marked by area 63B in FIG. 63A). The plurality of struts 364 may include a strut 364*a* that may include a plurality of segments 372*a*, 372*b*, and 372*c*. The segments may comprise a first segment 372*a*, a second segment 372*b*, and a third segment 372*c*. The first segment 372*a* may extend along a first axis 375*a*. The second segment 372*b* may extend along a second axis 375*b*. The strut 364*a* may include a first kink 374*a* that may join the first segment 372*a* to the second segment 372*b* at an angle. The strut 364*a* may include a second kink 374*b* that may join the second segment 372*b* to the third segment 364*c* at an angle. The first axis 375*a* may be offset from the second axis 375*b*.

The second segment 372*b* may extend at an angle relative to the first segment 372*a* that causes the second segment 372*b* to extend diagonally with respect to the first segment 372*a*. An angle between the first segment 372*a* and the second segment 372*b* may be an obtuse angle. The obtuse angle may cause the second segment 372*b* to extend both circumferentially and axially with respect to the first segment 372*a*. The circumferential extent of the second segment 372*b* may offset the third segment 372*c* circumferentially from the first segment 372*a*.

The third segment 372*c* may extend at an angle relative to the second segment 372*b*. The angle between the third segment 372*c* and the second segment 372*b* may be an obtuse angle and may be in an opposite direction as the angle between the first segment 372*a* and the second segment 372*b*. The obtuse angle may allow the third segment 372*c* to extend axially, similar to the first segment 372*a*, yet with the second axis 375*b* offset from the first axis 375*a*.

Figure 64:
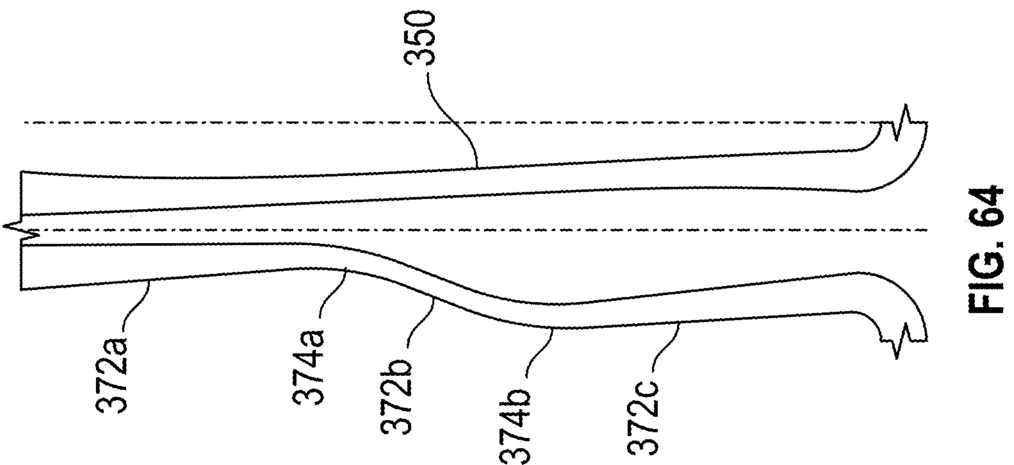
FIG. 64 illustrates a side view of a strut of FIG. 63A adjacent to a strut of FIG. 62A.

The first kink 374*a* and the second kink 374*b* accordingly may displace the length of the first segment 372*a* from the length of the second segment 372*b* and the displacement may be circumferential as shown in FIG. 63B. As such, a radial compression applied to the strut 364*a* in the configuration shown in FIG. 63B to reach a crimped configuration or undeployed configuration may result in less strain for the strut 364*a* than with a straight strut as shown in FIG. 62A for example. A comparison of a shape of a strut having the first kink 374*a* and the second kink 374*b* as compared with a straight strut 350 is shown in FIG. 64 for example.

Referring to FIG. 63B, in embodiments, the first segment 372*a* of the strut may comprise a first end segment of the strut that may couple to a first juncture 366*a* of the frame 362. The third segment 372*c* of the strut may comprise a second end segment that may couple to a second juncture 366*b* of the frame 362. The remainder of the strut between the ends may be unconnected to any other portion of the frame 362.

In embodiments, the first axis 375*a* may extend parallel with the second axis 375*b*. In embodiments, the second axis 375*b* may extend at an angle relative to the first axis 375*a* yet remain offset from the first axis 375*a*. The second segment 372*b* may extend along an axis that extends at an angle with respect to the first axis 375*a* and the second axis 375*b*.

In embodiments, the prosthetic valve utilizing the frame 362 may extend around a central axis (similar to the central axis 315 shown in FIG. 56). The first axis 375*a* and the second axis 375*b* may both extend parallel with the central axis 315 in embodiments. The second segment 372*b* may extend at an angle with respect to the central axis.

The frame 362 may include other struts configured similarly as the strut 364*a* in embodiments. For example, as shown in FIG. 63B, the frame 362 may include a strut 364*b* positioned adjacent to the strut 364*a* and including a first segment 376*a*, a second segment 376*b*, and a third segment 376*c*. The first segment 376*a* may extend along a third axis and the third segment 376*c* may extend along a fourth axis. A first kink 378*a* may join the first segment 376*a* to the second segment 376*b* at an angle such that the second segment 376*b* extends towards the strut 364*a*. The second kink 378*b* may join the second segment 376*b* to the third segment 376*c* at an angle. The fourth axis may be offset from the third axis.

In embodiments, the strut 364*b* may comprise an inversion of the strut 364*a* positioned circumferentially adjacent to the strut 364*a*. The third segment 372*c* of the strut 364*a* may be joined to the third segment 376*c* of the strut 364*b* at the juncture 366*b*.

Figure 65A:
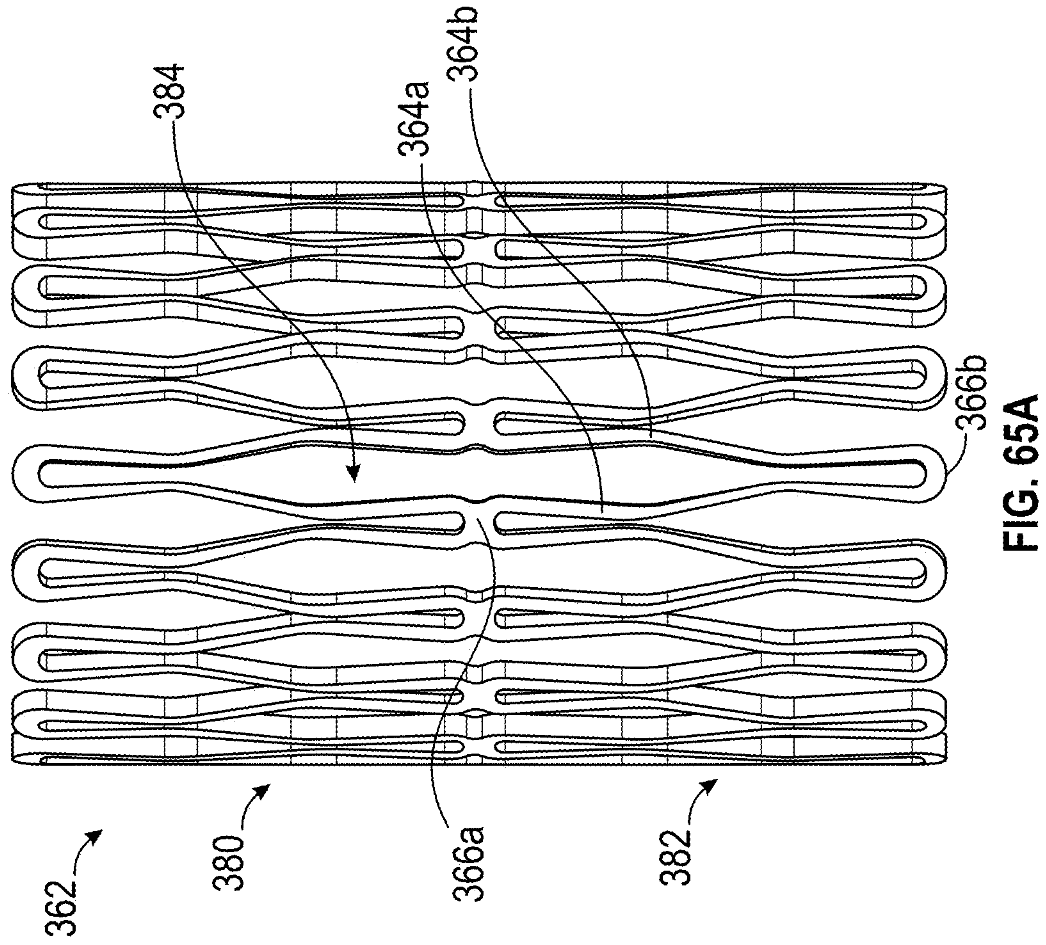
FIG. 65A illustrates a side view of a frame including struts as shown in FIG. 63A.

In embodiments, the frame 362 may include a repeating pattern of the first strut 364*a* adjacent to the second strut 364*b* that repeats circumferentially about the frame 362. For example, as shown in FIG. 65A, the pattern may repeat circumferentially to form a cylindrical frame 362 that may extend around a central axis of the prosthetic valve. As such, referring back to FIG. 63B, a third strut 364*c* that may be a repetition of the second strut 364*b* may be positioned circumferentially adjacent to the first strut 364*a*. The third strut 364*c* may be positioned on the other side of the first strut 364*a* than the second strut 364*b*.

The third strut 364*c*, being a repetition of the second strut 364*b*, may include a first segment 381*a*, a second segment

381*b*, and a third segment 381*c*. The first segment 381*a* may extend along a fifth axis and the third segment 381*c* may extend along a sixth axis. A first kink may join the first segment 381*a* to the second segment 381*b* at an angle such that the second segment 381*b* extends away from the strut 364*a*. The second kink may join the second segment 381*b* to the third segment 381*c* at an angle. The fifth axis may be offset from the sixth axis. The first segment 381*a* of the third strut 364*c* may couple to the first segment 372*a* of the first strut 364*a* at the juncture 366*a*.

Referring to FIG. 65A, in embodiments, the frame 362 may include a proximal portion 380 and a distal portion 382. The distal portion 382 may include the circumferentially repeating pattern of the first strut 364*a* and the second strut 364*b*. The proximal portion 380, in embodiments, may include struts configured similarly as the first strut 364*a* or the second strut 364*b*. In embodiments, the proximal portion 380 may include struts comprising inversions of the first struts 364*a* and the second strut 364*b*. The struts together may form strut cells bounding openings 384.

The frame 362 may be configured as a cylindrical body in embodiments and may surround a plurality of prosthetic valve leaflets. The prosthetic valve leaflets may be configured similarly as embodiments of prosthetic valve leaflets disclosed herein. The frame 362 in embodiments may have a different shape than a cylindrical shape as desired.

The frame 362 may comprise an inner frame configured to support a plurality of prosthetic valve leaflets, or in embodiments, may comprise an outer frame configured to surround an inner frame supporting a plurality of prosthetic valve leaflets. In embodiments, both an inner frame and an outer frame may include one or more struts configured similarly as the strut 364*a*, or may include a pattern of the struts 364*a*, 364*b*. In embodiments, the frame 362 may comprise a single frame that is utilized with the prosthetic valve.

Figure 65B:
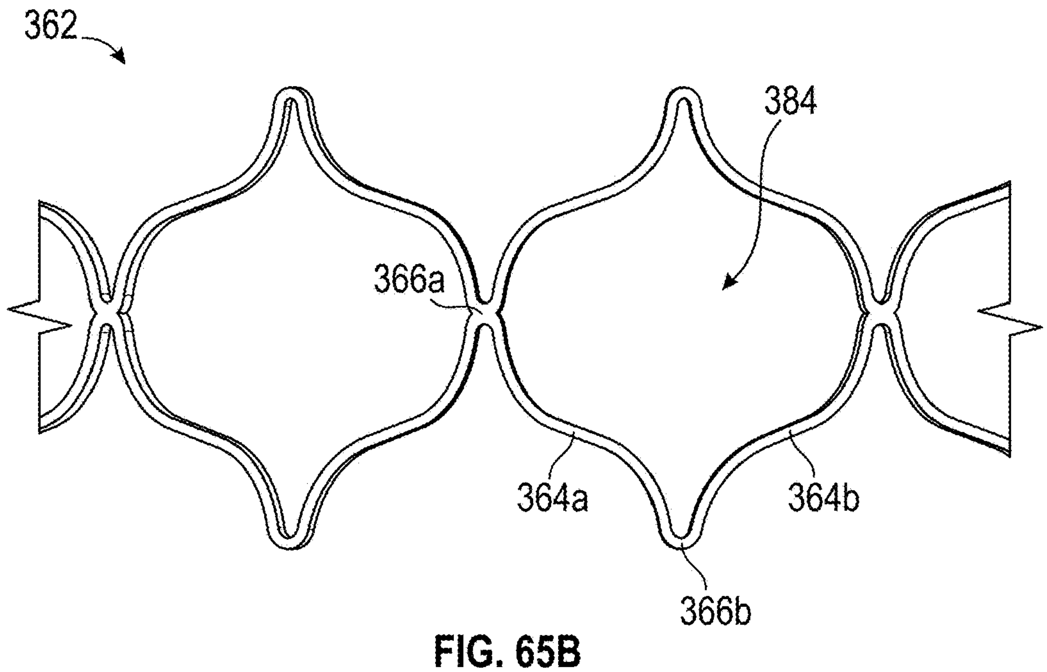
FIG. 65B illustrates a side view of a portion of a frame as shown in FIG. 65A expanded.

The configuration of the struts 364*a*, 364*b* may allow for improved radial compression of the frame 362 and reduced strain applied to the struts 364*a*, 364*b*. FIG. 65A, for example, illustrates the frame 362 in an uncompressed configuration. FIG. 65B illustrates a portion of the frame 362 in an expanded configuration. The frame 362 may be radially expanded and the struts 364*a*, 364*b* may be moved circumferentially away from each other. The size of the opening 384 has increased.

Figure 65C:
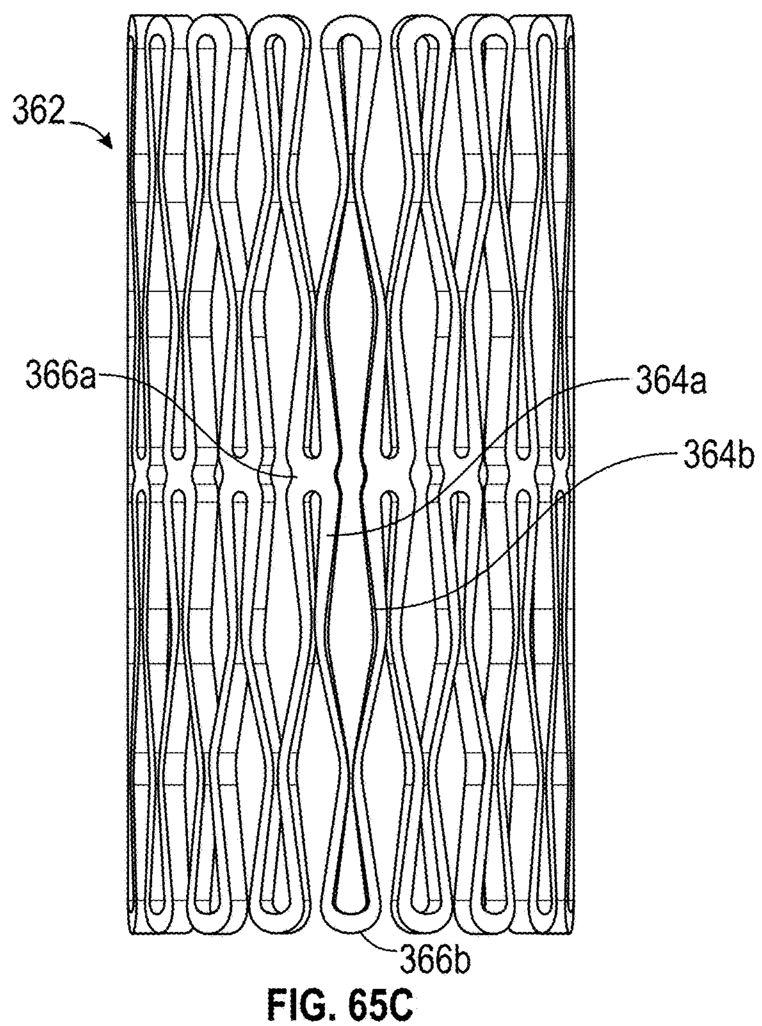
FIG. 65C illustrates a side view of the frame shown in FIG. 65A compressed.

FIG. 65C illustrates the frame 362 in a compressed state. The frame 362 has been radially compressed inward. The strut 364*a* is drawn to the strut 364*b* upon the radial compression of the frame 362. Strain in the ends of the struts 364*a*, 364*b* may be reduced from a configuration of struts as shown in FIG. 62C for example. In embodiments, portions of the struts 364*a*, 364*b* may contact each other. The respective adjacent kinks (e.g., the second kink 374*b* of the first strut 364*a*, and the second kink 378*b* of the second strut 364*b*) of the struts may contact each other upon radial compression of the frame 362 to further relieve strain upon the struts 364*a*, 364*b*. The degree of strain provided may be reduced due to the contact between the kinks. Further, the width of the struts may be reduced from an embodiment as shown in FIG. 62A for example.

Further, upon expansion, the angles between adjacent struts (for example, the angle between struts 364*a*, 364*b* at the junction 366*b*) may remain smaller than in an embodiment as shown in FIG. 62A for example. Such a feature may further reduce strain upon the struts.

In embodiments, the prosthetic valve utilizing the frame and the struts may comprise a valve configured to be deployed to a native mitral valve or native tricuspid valve, among other implantation sites as desired. The features of the prosthetic valve may be utilized solely or in combination with any other embodiment disclosed herein. The prosthetic valve may be deployed to the implantation site utilizing deployment methods disclosed herein.

Figure 66:
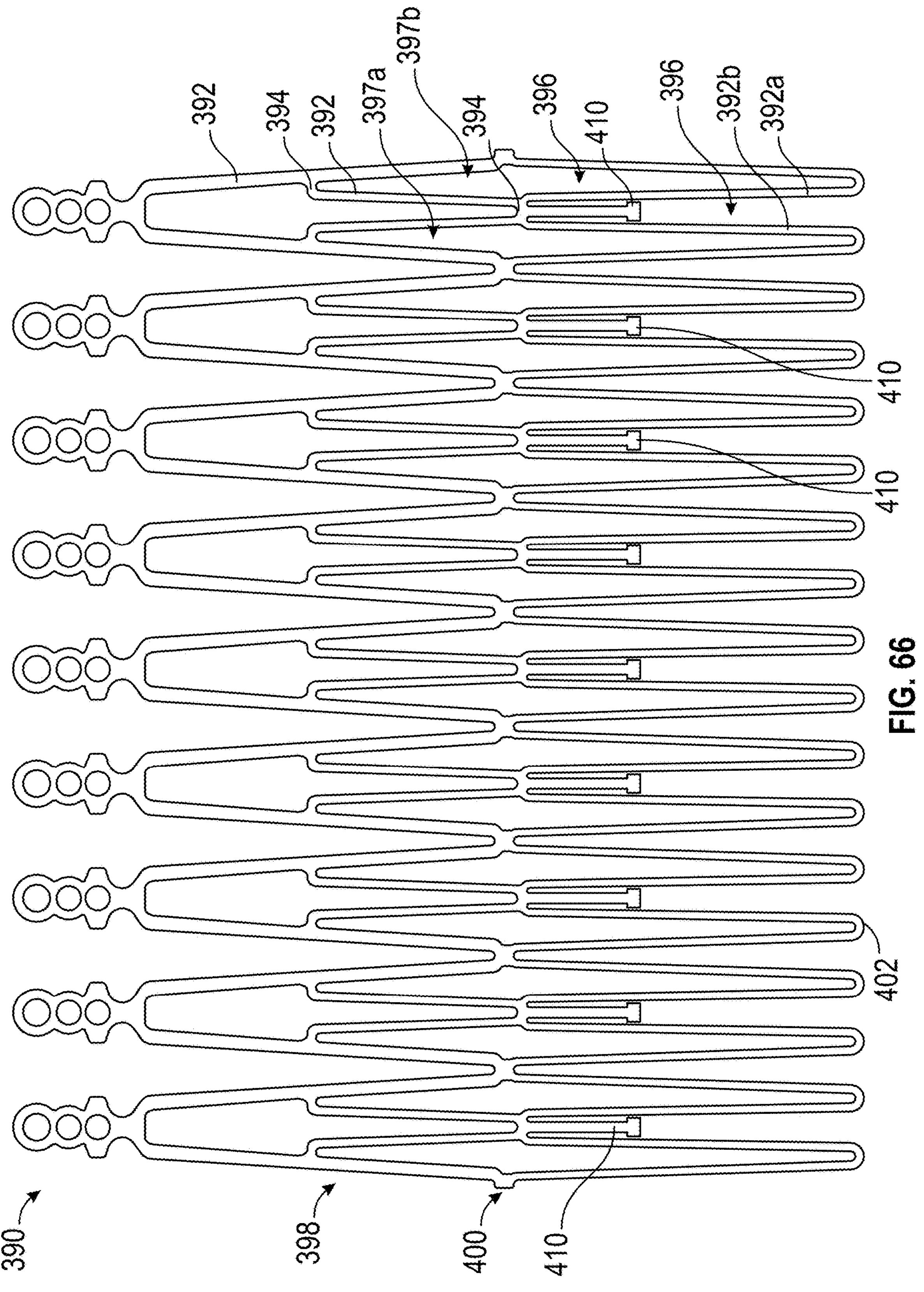
FIG. 66 illustrates a plan view of a frame according to an embodiment of the present disclosure.
Figure 67:
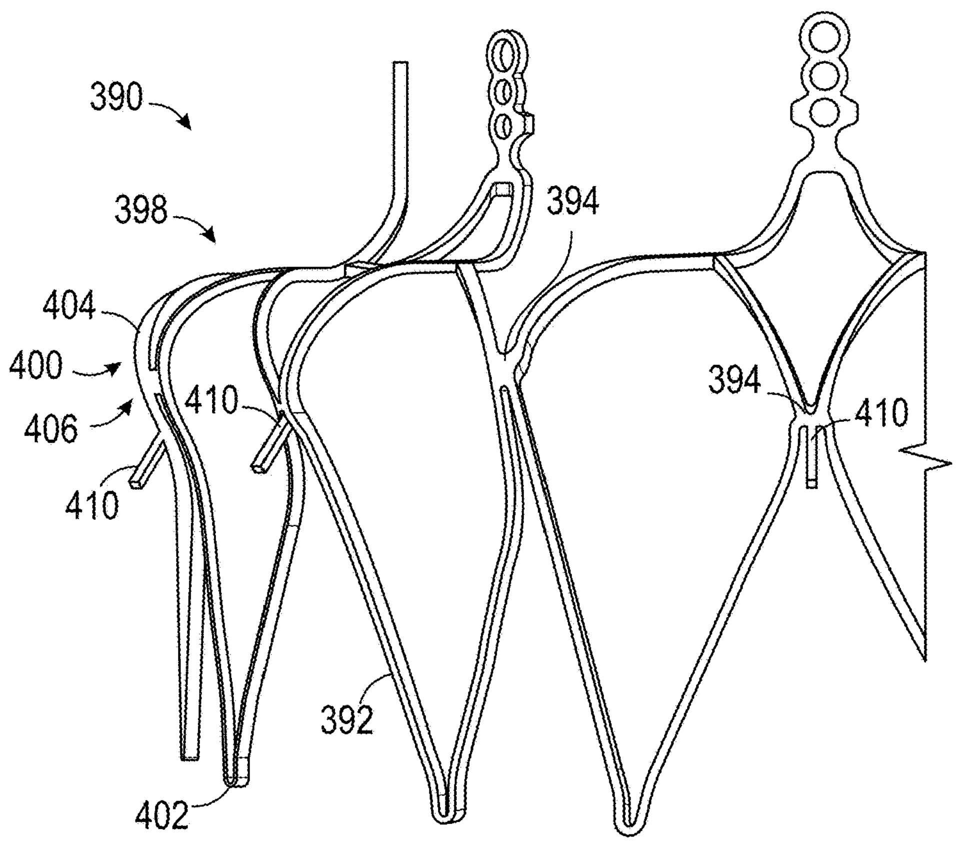
FIG. 67 illustrates a side view of a portion of the frame shown in FIG. 66.
Figure 68:
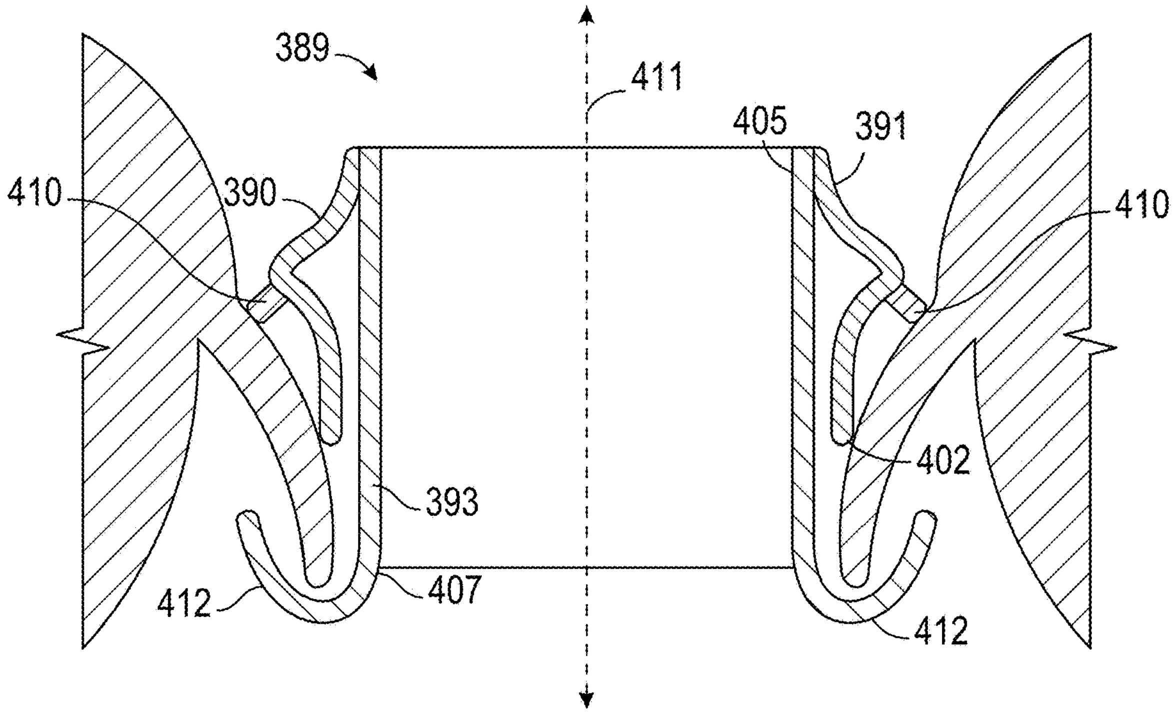
FIG. 68 illustrates a cross sectional schematic view of a prosthetic valve utilizing the frame shown in FIG. 66.

FIG. 66 illustrates a plan view of a flattened outer frame 390 that may be utilized with a prosthetic valve 389 (marked in FIG. 68). FIG. 67 illustrates a side view of a portion of the outer frame 390. FIG. 68 illustrates a schematic cross sectional view of the prosthetic valve 389. Referring to FIGS. 66-68, the prosthetic valve 389 may include an inner frame 393 that may be configured to support a plurality of prosthetic valve leaflets. The prosthetic valve leaflets may be configured similarly as other prosthetic valve leaflets disclosed herein. The inner frame 393 may be configured similarly as other inner frames disclosed herein, including a plurality of struts connected at junctures. The inner frame 393 may include a proximal portion 405 and a distal portion 407.

The outer frame 390 may comprise a portion of a sealing body 391 that may be utilized to form a seal with a portion of a heart valve. The sealing body 391 may be positioned radially outward of the inner frame 393. The sealing body 391 may include a skirt coupled to the outer frame 390 or in embodiments a skirt may be excluded. The sealing body 391 and outer frame 390 may extend around the inner frame 393 in embodiments.

The outer frame 390 may include a plurality of struts 392 connected at junctures 394 and may include openings 396 between struts 392. In embodiments, the struts 392 may form strut cells, which may be configured similarly as other configurations of strut cells disclosed herein.

The outer frame 390 may include a proximal portion 398 and a distal portion 400. Referring to FIG. 67, the outer frame 390 may be configured such that the proximal portion 398 extends radially outward from the inner frame 393. The proximal portion 398 of the outer frame 390 may be configured to couple to a proximal portion 405 of an inner frame 393, as shown in FIG. 68 for example.

As shown in FIG. 67, the distal portion 400 of the outer frame 390 may curve axially from the proximal portion 398 and may extend axially to a distal end 402 of the outer frame 390. In embodiments, the distal portion 400 may include a curved portion 404 that may curve axially from the proximal portion 398. The curved portion 404 may be configured to curve radially inward to form a shoulder 406 as shown in FIG. 67, for example. The shoulder 406 may comprise a protruding portion of the outer frame 390 that may be configured to impede distal movement of the outer frame 390 and the prosthetic valve 389. The shoulder 406 may be configured to contact a portion of a heart valve annulus on a side of the annulus to impede distal movement of the outer frame 390 and the prosthetic valve 389. The shoulder 406 may be positioned on an atrial side of a heart valve for example.

In embodiments, a plurality of anchors 410 may extend radially outward from the distal portion 400 of the outer frame 390 and may be configured to impede distal movement of the outer frame 390. Referring to FIG. 66, the anchors 410 may be coupled to the junctures 394 of the outer frame 390, and in particular may be coupled to junctures 394 between the distalmost struts 392*a, b* and the distalmost strut cells 397*a, b*. The anchors 410 may be positioned between the struts 392*a, b* and may be positioned within the opening 396*a* between the distalmost struts 392*a, b*. The anchors 410 may be integral with the outer frame 390 in embodiments or may be otherwise coupled to the outer frame 390. Each anchor 410 may comprise an arm extending from the outer frame 390 to a tip of the arm.

Referring to FIG. 67, the anchors 410 may be deflected radially outward from the outer frame 390. The anchors 410 may extend radially outward from the outer frame 390 and particularly may extend radially outward from the curved portion 404 of the outer frame 390. The anchors 410 may be positioned at the shoulder 406 of the outer frame 390 and distal of the largest radial extent of the shoulder 406. The anchors 410 in embodiments may protrude from the outer frame 390 at an angle with respect to a central axis 411 of the prosthetic valve 389 marked in FIG. 68. The angle may be in a distal direction in embodiments.

The anchors 410 may be spaced from each other circumferentially, with equal spacing or with other spacing in embodiments as desired.

Referring to FIG. 68, the anchors 410 may impede distal movement of the outer frame 390 by contacting a portion of a heart. The portion may comprise a portion of a heart valve annulus and may comprise an atrial portion of a heart valve annulus in embodiments. The portion may comprise a portion of heart valve leaflets in embodiments. The anchors 410 may provide an axial force that reduces the possibility of distal movement. Such force may be distinguished from a radial force that may be applied, although in embodiments an axial and a radial force may be applied by the anchors 410. In embodiments, the anchoring by the anchors 410 may be independent of a radial force. The anchors 410 may serve to reduce the possibility of distal migration of the prosthetic valve 389, which may be ventricular migration in embodiments. The position of the anchors 410 may be supra annular or intra annular in embodiments.

In embodiments, the prosthetic valve 389 may include additional anchors. For example, in embodiments, the anchors 410 may comprise proximal anchors and distal anchors 412 may be utilized. The distal anchors 412 may be configured similarly as other embodiments of distal anchors 412 disclosed herein, and may be configured to extend over a tip of a native leaflet of a native valve in embodiments. In embodiments, other forms of distal anchors and/or additional proximal anchors may be utilized as desired. In embodiments, the anchors 410 may comprise atrial anchors configured to be positioned on an atrial side of a native valve and the distal anchors 412 may comprise ventricular anchors. Other configurations of anchors may be utilized in embodiments as desired.

Various modifications of the anchors and frames disclosed herein may be utilized as desired. In embodiments, the configuration of anchors may be utilized with a single frame that supports the prosthetic valve leaflets. Other configurations may be utilized as desired.

In embodiments, the prosthetic valve 389 may comprise a valve configured to be deployed to a native mitral valve or native tricuspid valve, among other implantation sites as desired. The features of the prosthetic valve may be utilized solely or in combination with any other embodiment disclosed herein. The prosthetic valve may be deployed to the implantation site utilizing deployment methods disclosed herein.

The implants disclosed herein may include prosthetic heart valves or other forms of implants, such as stents or filters, or diagnostic devices, among others. The implants may be expandable implants configured to move from a compressed or undeployed state to an expanded or deployed state. The implants may be compressible implants configured to be compressed inward to have a reduced outer profile and to move the implant to the compressed or undeployed state.

Various forms of delivery apparatuses may be utilized with the embodiments disclosed herein. The delivery apparatuses as disclosed herein may be utilized for aortic, mitral, tricuspid, and pulmonary replacement and repair as well. The delivery apparatuses may comprise delivery apparatuses for delivery of other forms of implants, such as stents or filters, or diagnostic devices, among others.

The implants and the systems disclosed herein may be used in transcatheter aortic valve implantation (TAVI) or replacement of other native heart valves (e.g., mitral, tricuspid, or pulmonary). The delivery apparatuses and the systems disclosed herein may be utilized for transarterial access, including transfemoral access, to a patient's heart. The delivery apparatuses and systems may be utilized in transcatheter percutaneous procedures, including transarterial procedures, which may be transfemoral or transjugular. Transapical procedures, among others, may also be utilized. Other procedures may be utilized as desired.

Features of embodiments may be modified, substituted, excluded, or combined across embodiments as desired.

In addition, the methods herein are not limited to the methods specifically described, and may include methods of utilizing the systems and apparatuses disclosed herein. The steps of the methods may be modified, excluded, or added to, with systems, apparatuses, and methods disclosed herein.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of systems, apparatuses, and methods as disclosed herein, which is defined solely by the claims. Accordingly, the systems, apparatuses, and methods are not limited to that precisely as shown and described.

Certain embodiments of systems, apparatuses, and methods are described herein, including the best mode known to the inventors for carrying out the same. Of course, variations on these described embodiments will become apparent to those of ordinary skill in the art upon reading the foregoing description. The inventor expects skilled artisans to employ such variations as appropriate, and the inventors intend for the systems, apparatuses, and methods to be practiced otherwise than specifically described herein. Accordingly, the systems, apparatuses, and methods include all modifications and equivalents of the subject matter recited in the claims appended hereto as permitted by applicable law. Moreover, any combination of the above-described embodiments in all possible variations thereof is encompassed by the systems, apparatuses, and methods unless otherwise indicated herein or otherwise clearly contradicted by context.

Groupings of alternative embodiments, elements, or steps of the systems, apparatuses, and methods are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses an approximation that may vary, yet is capable of performing the desired operation or process discussed herein.

The terms "a," "an," "the" and similar referents used in the context of describing the systems, apparatuses, and methods (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the systems, apparatuses, and methods and does not pose a limitation on the scope of the systems, apparatuses, and methods otherwise claimed. No language in the present specification should be construed as indicating any non-claimed element essential to the practice of the systems, apparatuses, and methods.

All patents, patent publications, and other publications referenced and identified in the present specification are individually and expressly incorporated herein by reference in their entirety for the purpose of describing and disclosing, for example, the compositions and methodologies described in such publications that might be used in connection with the systems, apparatuses, and methods. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A prosthetic valve for deployment in a native valve, the prosthetic valve comprising:

an inner frame having a proximal portion and a distal portion;

a plurality of prosthetic valve leaflets extending radially inwardly from the inner frame;

one or more anchors coupled to the distal portion of the inner frame, each anchor curving in a proximal direction and having a tip, each anchor shaped to hook around a native leaflet of the native valve; and a sealing body positioned radially outwardly of the inner frame, the sealing body including an outer frame and a skirt, the sealing body sized to contact an annulus of a patient's heart, the outer frame having a distal portion comprising a plurality of struts separated by spaces, the spaces positioned for allowing the tip of the respective anchor to pass through the respective space in a radially inward direction upon the respective anchor failing to hook around the native leaflet of the native valve;

wherein the one or more anchors are configured such that the tip of the respective anchor is positioned radially inward of adjacent struts of the plurality of struts when the respective anchor fails to grasp one or more of the native leaflets.

2. The prosthetic valve of claim 1, wherein the distal portion of the inner frame is spaced inwardly from the outer frame with a gap therebetween, and each of the one or more anchors is configured to extend radially outwardly from the inner frame and across the gap.

3. The prosthetic valve of claim 1, wherein the skirt further comprises one or more receiving portions comprising one or more of pockets or apertures.

4. The prosthetic valve of claim 3, wherein the skirt includes a proximal portion and a distal portion, and the distal portion of the skirt includes the one or more of pockets or apertures.

5. The prosthetic valve of claim 1, wherein the outer frame includes a proximal portion coupled to the proximal portion of the inner frame.

6. The prosthetic valve of claim 1, wherein each of the one or more anchors is configured to move radially outwardly from an undeployed configuration to a deployed configuration.

7. The prosthetic valve of claim 1, wherein the sealing body is shaped to envelop the one or more anchors.

8. The prosthetic valve of claim 1, wherein the sealing body has an outer diameter that is the same or greater than an outer diameter of the one or more anchors.

9. The prosthetic valve of claim 1, wherein the distal portion of the outer frame is configured to deflect radially inwards.

10. The prosthetic valve of claim 1, wherein the outer frame further comprises coupling bodies configured to couple the prosthetic valve to a delivery system.

11. A prosthetic valve for deployment in a native valve, the prosthetic valve comprising:

an inner frame supporting a plurality of prosthetic valve leaflets;

one or more ventricular anchors coupled to the inner frame, each of the one or more ventricular anchors, when in an expanded configuration, extend distally and then curve in a proximal direction; and a sealing body positioned radially outwardly of the plurality of prosthetic valve leaflets and shaped to contact a portion of a patient's heart;

wherein the one or more ventricular anchors are configured to capture native leaflets between the one or more ventricular anchors and the sealing body for securing the prosthetic valve in the patient's heart and wherein the sealing body includes a ventricular portion including a plurality of struts separated by one or more openings for allowing the one or more ventricular anchors to pass through the sealing body in a radial inward direction when the native leaflet is not captured between the one or more ventricular anchors and the sealing body;

wherein respective anchors of the one or more ventricular anchors are configured to be located radially inwardly of respective openings upon failing to capture the native leaflet.

12. The prosthetic valve of claim 11, wherein the sealing body further comprises a skirt having one or more of pockets or apertures.

13. The prosthetic valve of claim 11, wherein the sealing body comprises an outer metallic frame that surrounds the inner frame, the outer metallic frame having the plurality of struts.

14. The prosthetic valve of claim 13, wherein the outer metallic frame includes a proximal portion and a distal portion, with the proximal portion extending radially outwardly from the plurality of prosthetic valve leaflets and the distal portion being spaced from the plurality of prosthetic valve leaflets with a gap.

15. The prosthetic valve of claim 11, wherein each of the one or more ventricular anchors is configured to move radially outward from an undeployed configuration to a deployed configuration.

16. A prosthetic valve for deployment in a native valve, the prosthetic valve comprising:

an inner frame having a tubular shape and forming a lumen;

a plurality of prosthetic valve leaflets positioned within the lumen of the inner frame for providing one way flow through the prosthetic valve;

one or more anchors coupled to an outlet end of the inner frame; and a sealing body comprising an outer frame positioned radially outwardly of the inner frame for contacting an annulus of a heart, the outer frame having a ventricular portion having a plurality of struts separated by spaces;

wherein the one or more anchors are capable of trapping native leaflets against an outer surface of the sealing body and wherein, in the absence of a native leaflet, each of the one or more anchors is configured to move inwardly through respective spaces when respective anchors fail to capture the native leaflet;

wherein the one or more anchors, upon failing to capture one or more of the native leaflets of the native valve, are configured to be positioned radially inward of a respective space defined by the sealing body.

17. The prosthetic valve of claim 16, wherein the outer frame is an outer metallic frame.

18. The prosthetic valve of claim 16, wherein each of the one or more anchors is configured to extend distally and then curve in a proximal direction to a tip of the respective one of the one or more anchors.

19. The prosthetic valve of claim 18, wherein at least some of the tips of the respective one or more anchors are capable of at least partially passing through the sealing body in a radially inward direction.

20. The prosthetic valve of claim 16, wherein the sealing body is adapted to envelop the one or more anchors.

21. A prosthetic valve for deployment in a native heart valve, the prosthetic valve comprising:

a valve frame;

a plurality of prosthetic valve leaflets supported within the valve frame, the plurality of prosthetic valve leaflets configured to allow blood to flow in a downstream direction and inhibit blood flow in an upstream direction;

a plurality of anchors coupled to a distal portion of the valve frame, each anchor configured to curve in a proximal direction when the valve frame is in an expanded configuration and having a tip, each anchor configured to hook around a native leaflet of the native heart valve;

an outer frame positioned radially outward of the valve frame; and a skirt comprising a first portion and a second portion, the first portion positioned radially inward of the outer frame, and the second portion at least partially positioned radially outward of the outer frame, the second portion configured to receive and at least partially envelop at least the tip of at least one anchor of the plurality of anchors that fails to capture the native leaflet;

wherein the tip of a respective anchor is configured to pass through a gap of the outer frame and to be positioned radially inward of the outer frame when the respective anchor fails to hook a respective native leaflet.

* * * * *